United States Patent [19]

Reid et al.

[11] Patent Number: 5,417,986

[45] Date of Patent: May 23, 1995

[54] VACCINES AGAINST DISEASES CAUSED BY ENTEROPATHOGENIC ORGANISMS USING ANTIGENS ENCAPSULATED WITHIN BIODEGRADABLE-BIOCOMPATIBLE MICROSPHERES

[75] Inventors: Robert H. Reid, Kensington; Edgar C. Boedeker, Chevy Chase, both of Md.; John E. van Hamont, Shape, Belgium; Jean A. Setterstrom, Takoma Park, Md.

[73] Assignee: The United States of America as represented by the Secretary of the Army, Washington, D.C.

[21] Appl. No.: 867,301

[22] Filed: Apr. 10, 1992

Related U.S. Application Data

[63] Continuation-in-part of Ser. No. 805,721, Nov. 21, 1991, abandoned, which is a continuation-in-part of Ser. No. 690,485, Apr. 24, 1991, abandoned, which is a continuation-in-part of Ser. No. 521,945, May 11, 1990, abandoned, which is a continuation-in-part of Ser. No. 493,597, Mar. 15, 1990, abandoned, which is a continuation-in-part of Ser. No. 590,308, Mar. 16, 1984.

[51] Int. Cl.⁶ .......................... A61K 9/50; A61K 9/66; A61K 9/26
[52] U.S. Cl. .................... 424/499; 424/426; 424/455; 424/486; 424/488; 424/489; 424/444; 424/433; 424/470; 424/491; 424/422
[58] Field of Search ................. 424/499, 422, 85, 417, 424/450, 458, 469, 88, 89, 92, 863, 965

[56] References Cited

U.S. PATENT DOCUMENTS

| | | | |
|---|---|---|---|
| 4,863,735 | 9/1989 | Kohn et al. | 424/422 |
| 4,897,268 | 1/1990 | Tice et al. | 424/422 |

*Primary Examiner*—Raymond J. Henley, III
*Assistant Examiner*—T. J. Criares
*Attorney, Agent, or Firm*—Anthony T. Lane; Earl T. Reichert; Werten F. W. Bellamy

[57] ABSTRACT

This invention is directed to oral parenteral and intestinal vaccines and their use against diseases caused by enteropathogenic organisms using antigens encapsulated within biodegradable-biocompatible microspheres.

14 Claims, 70 Drawing Sheets

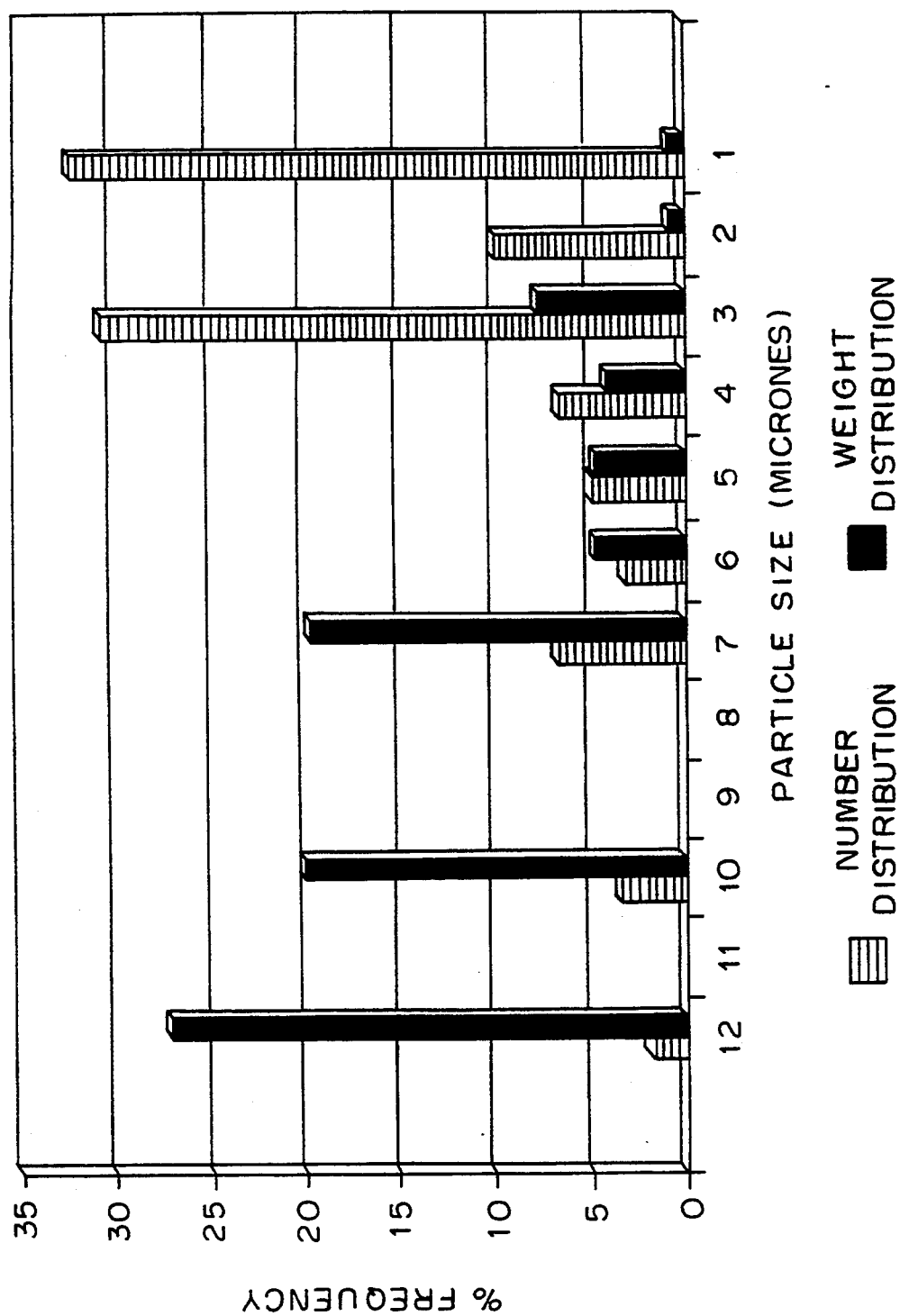

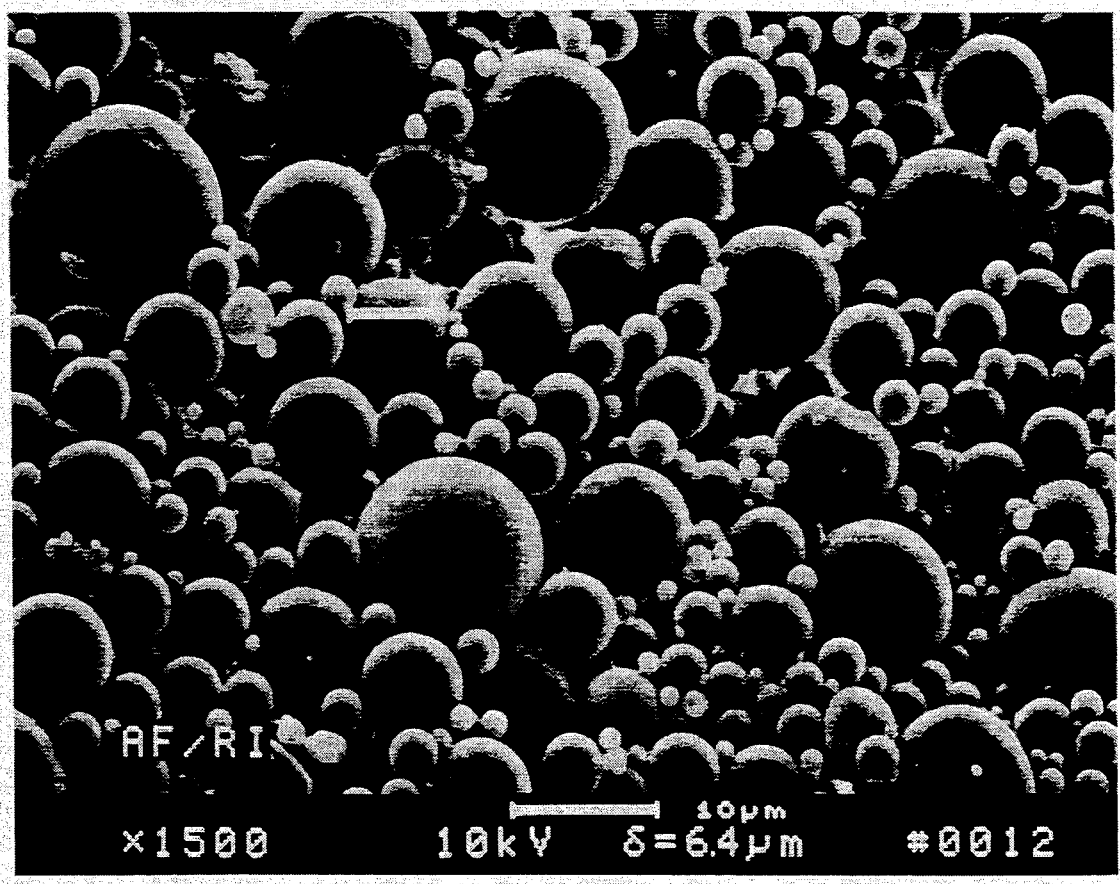

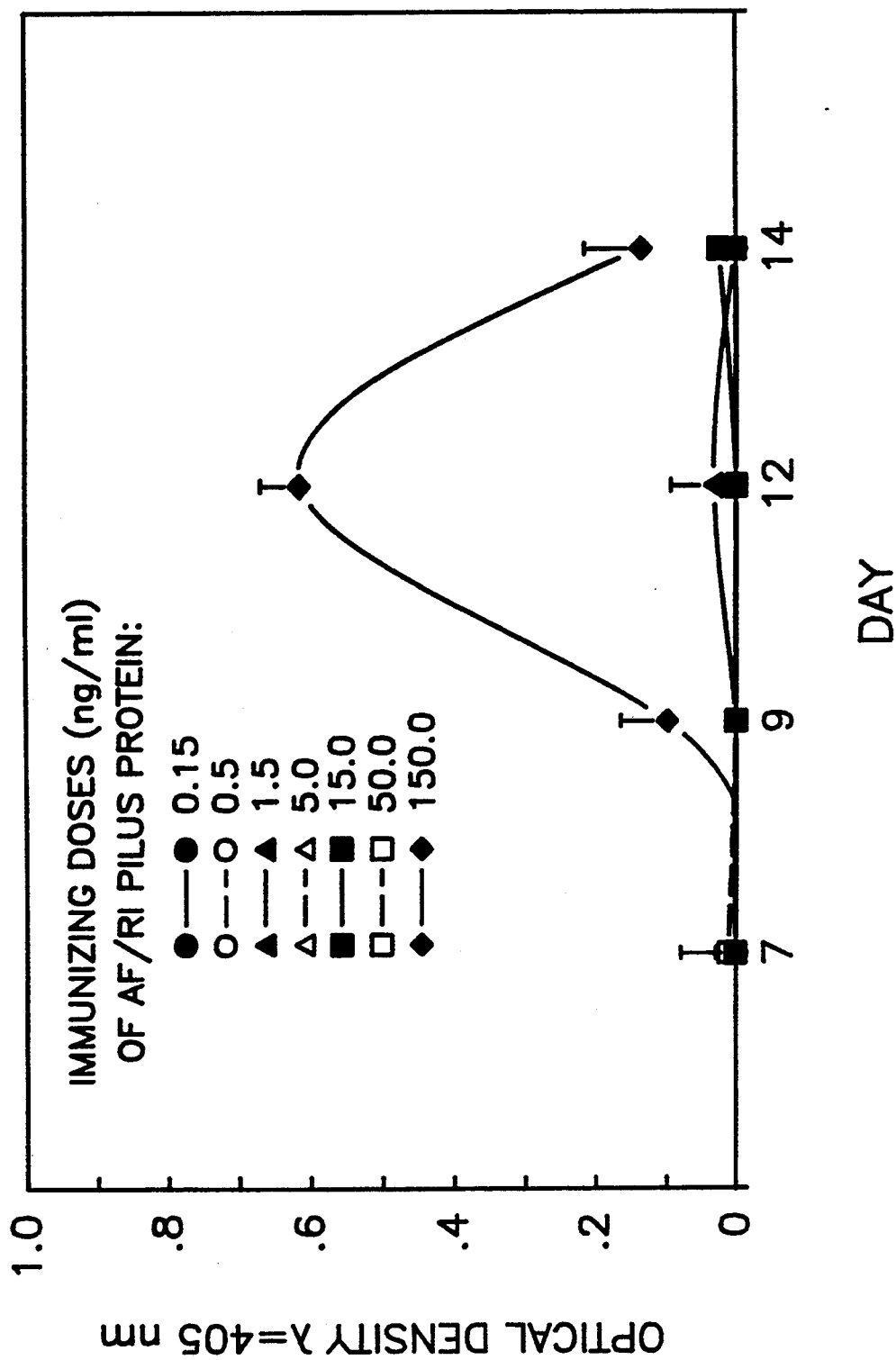

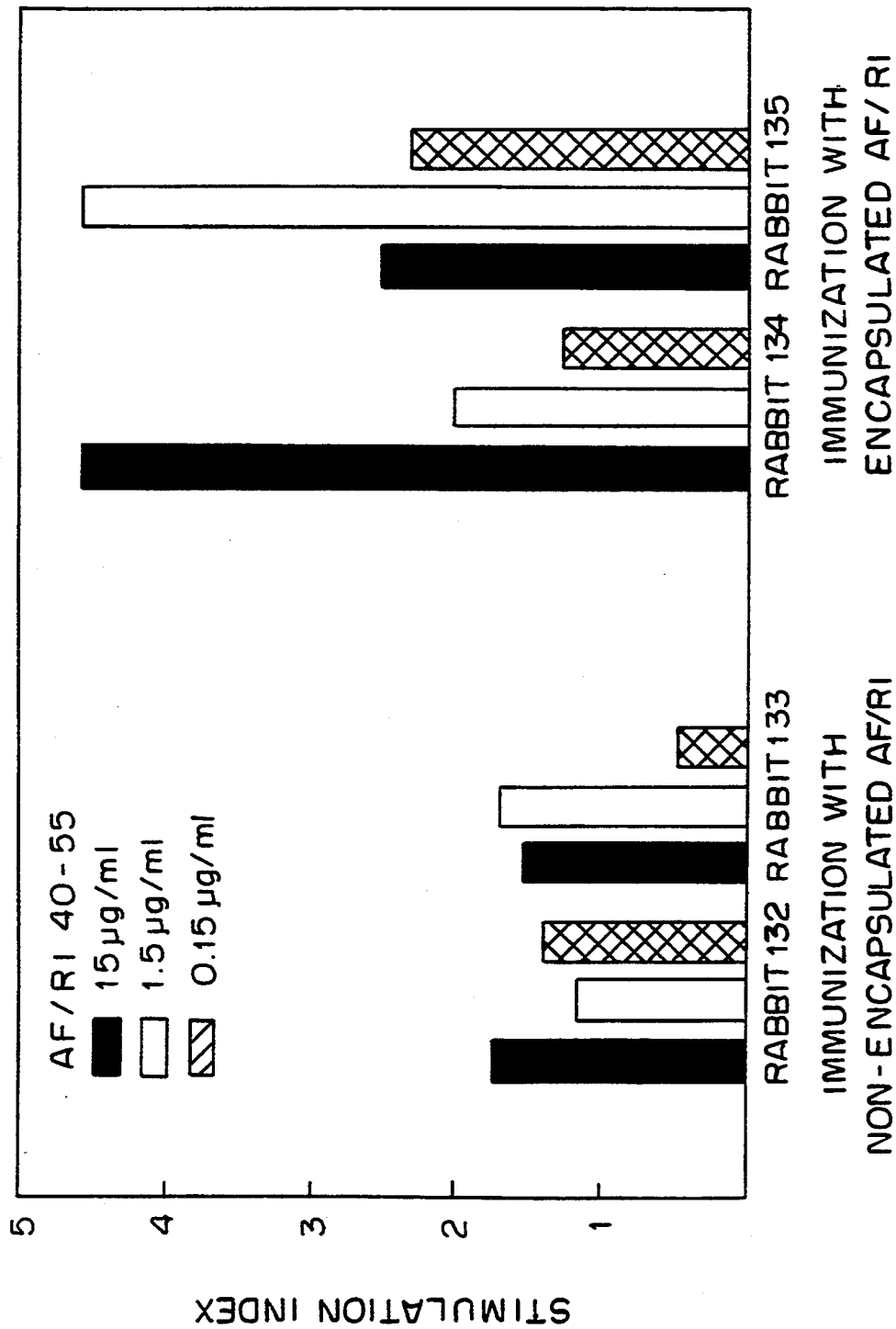

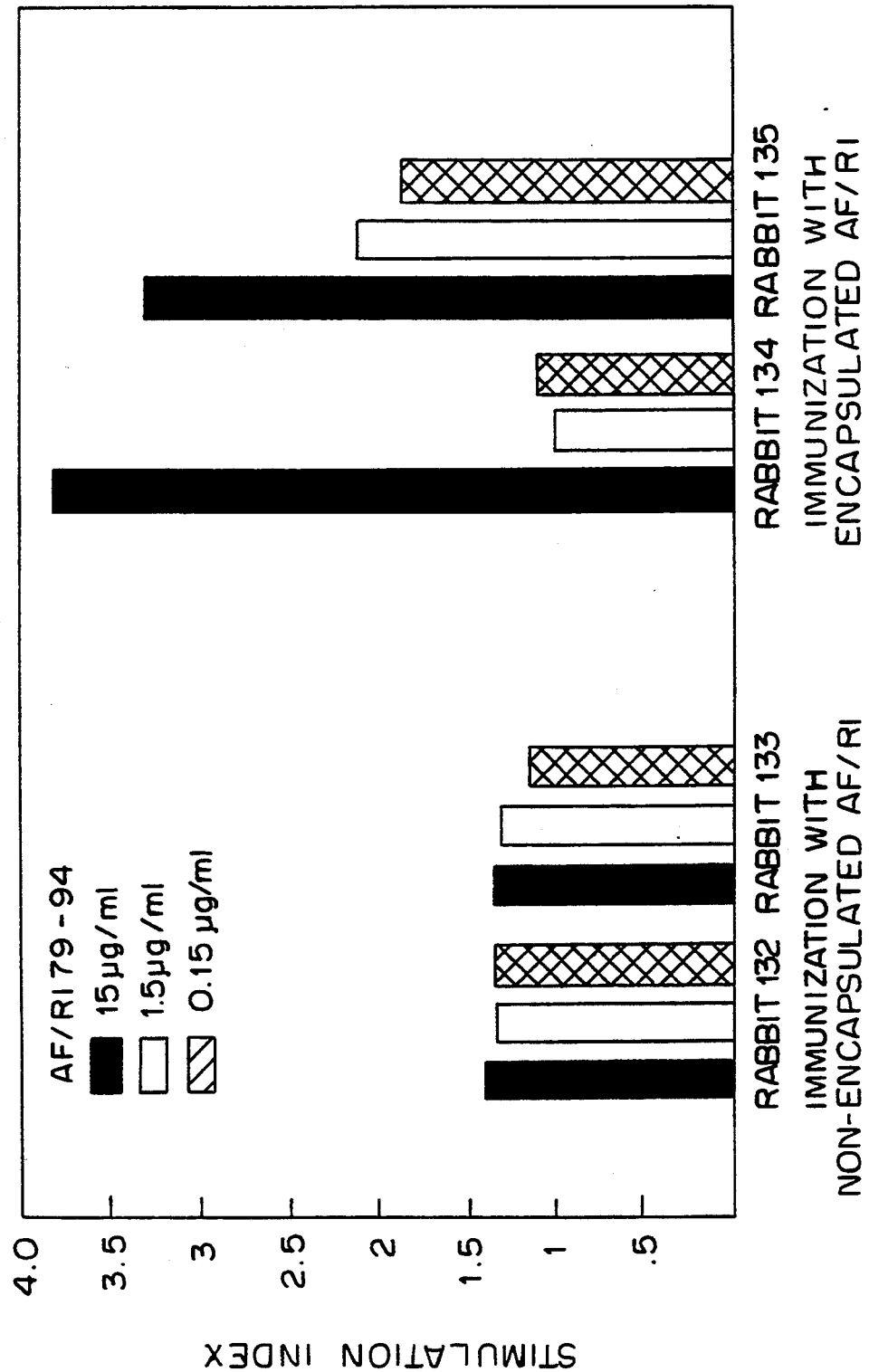

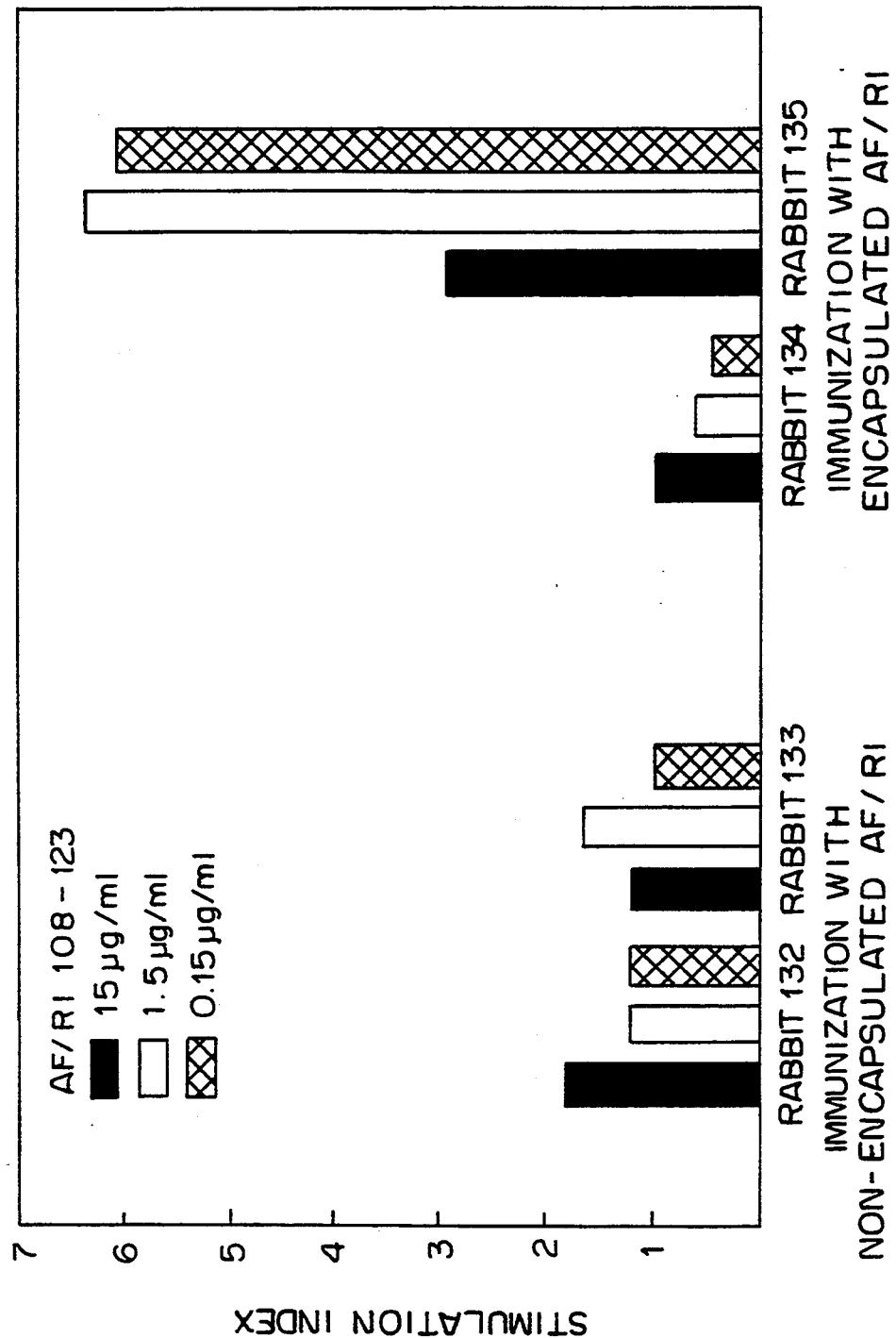

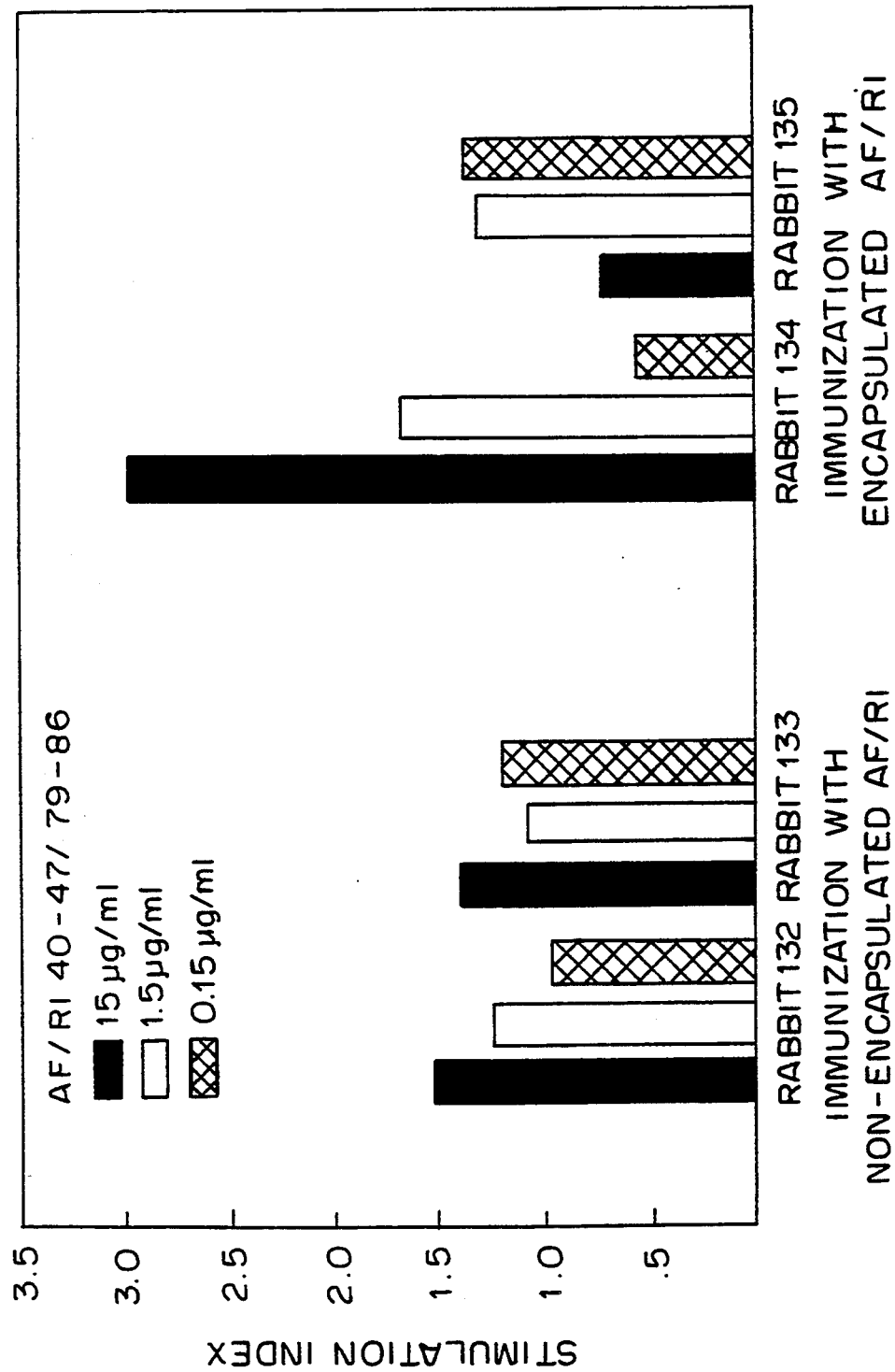

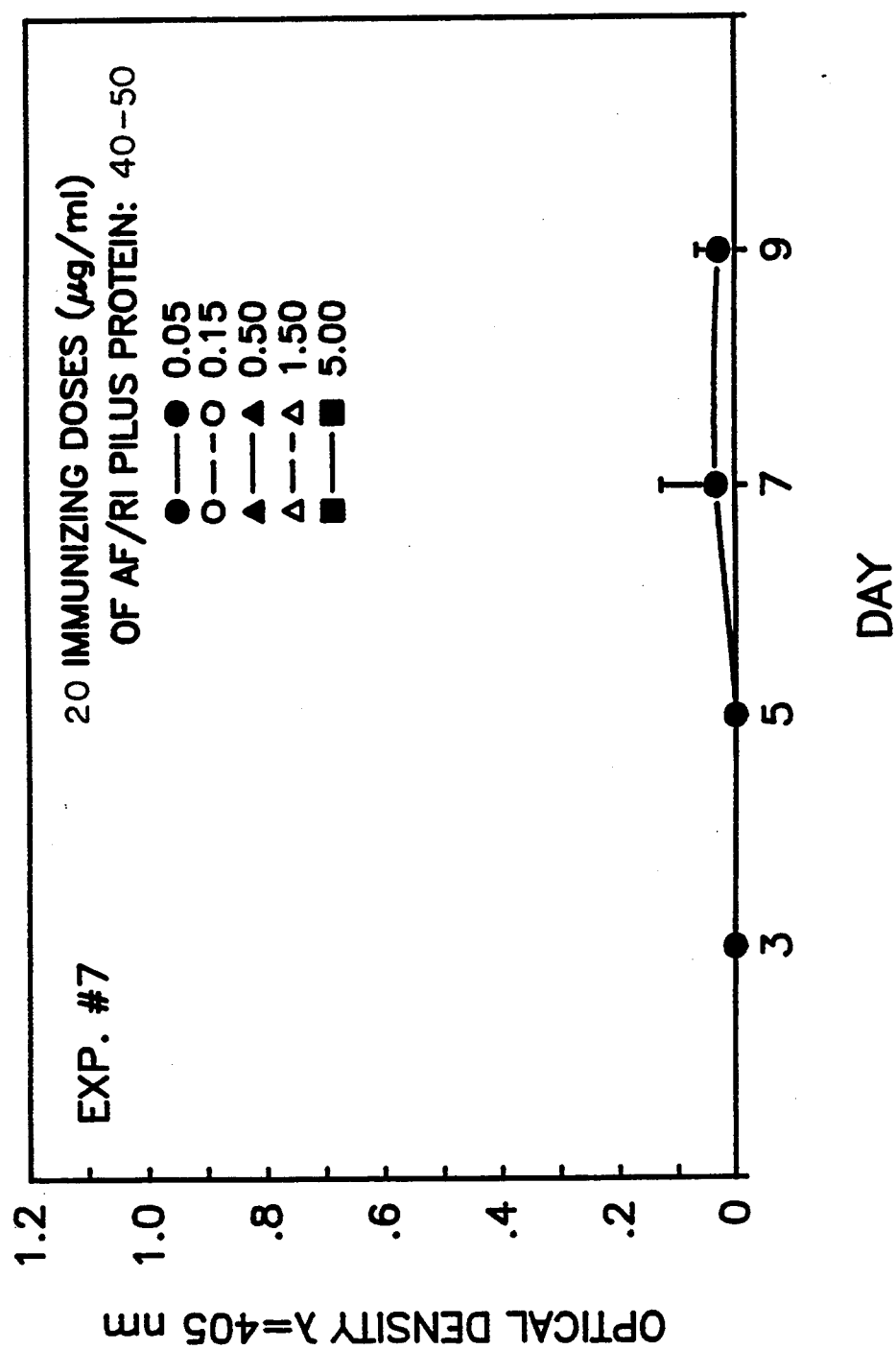

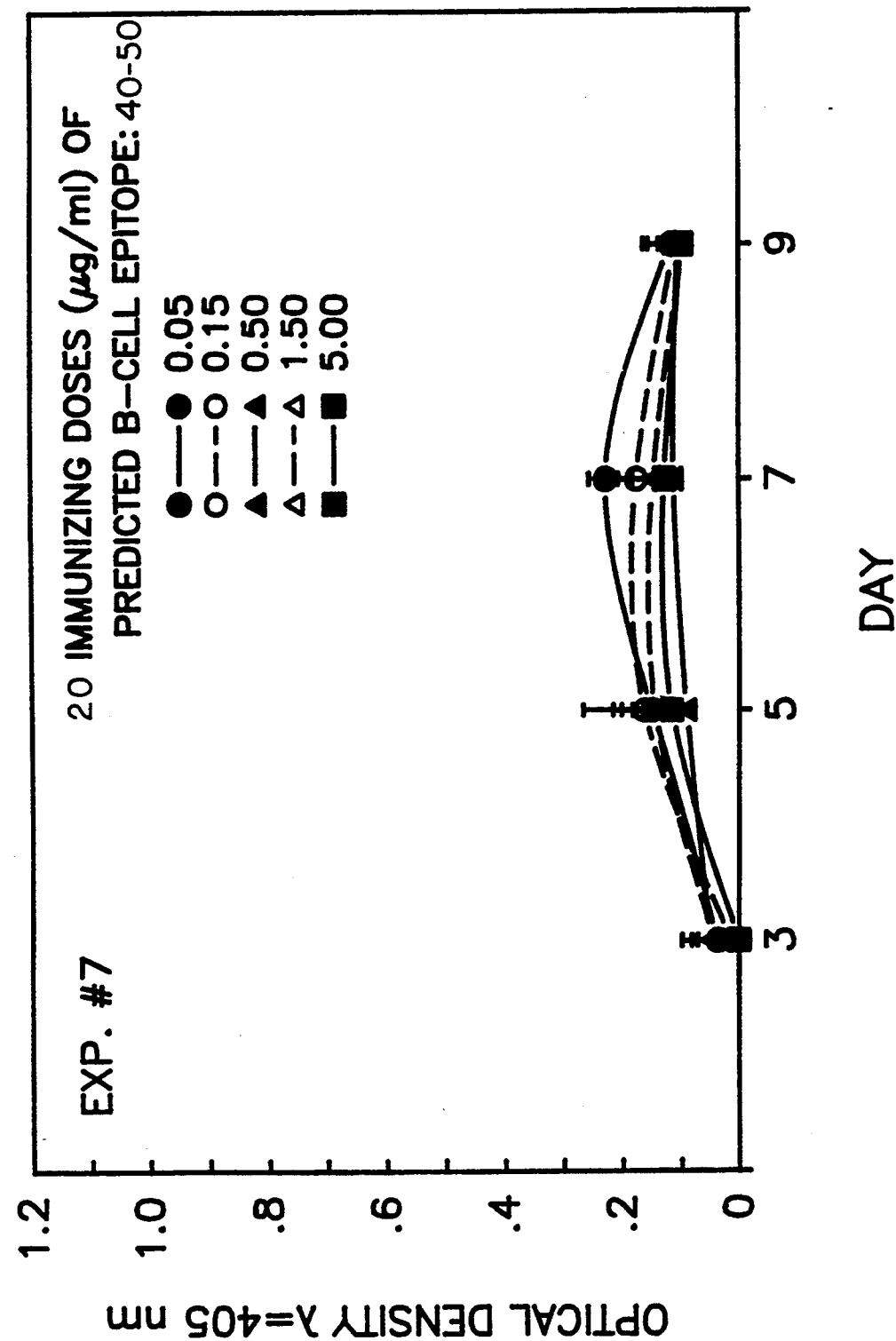

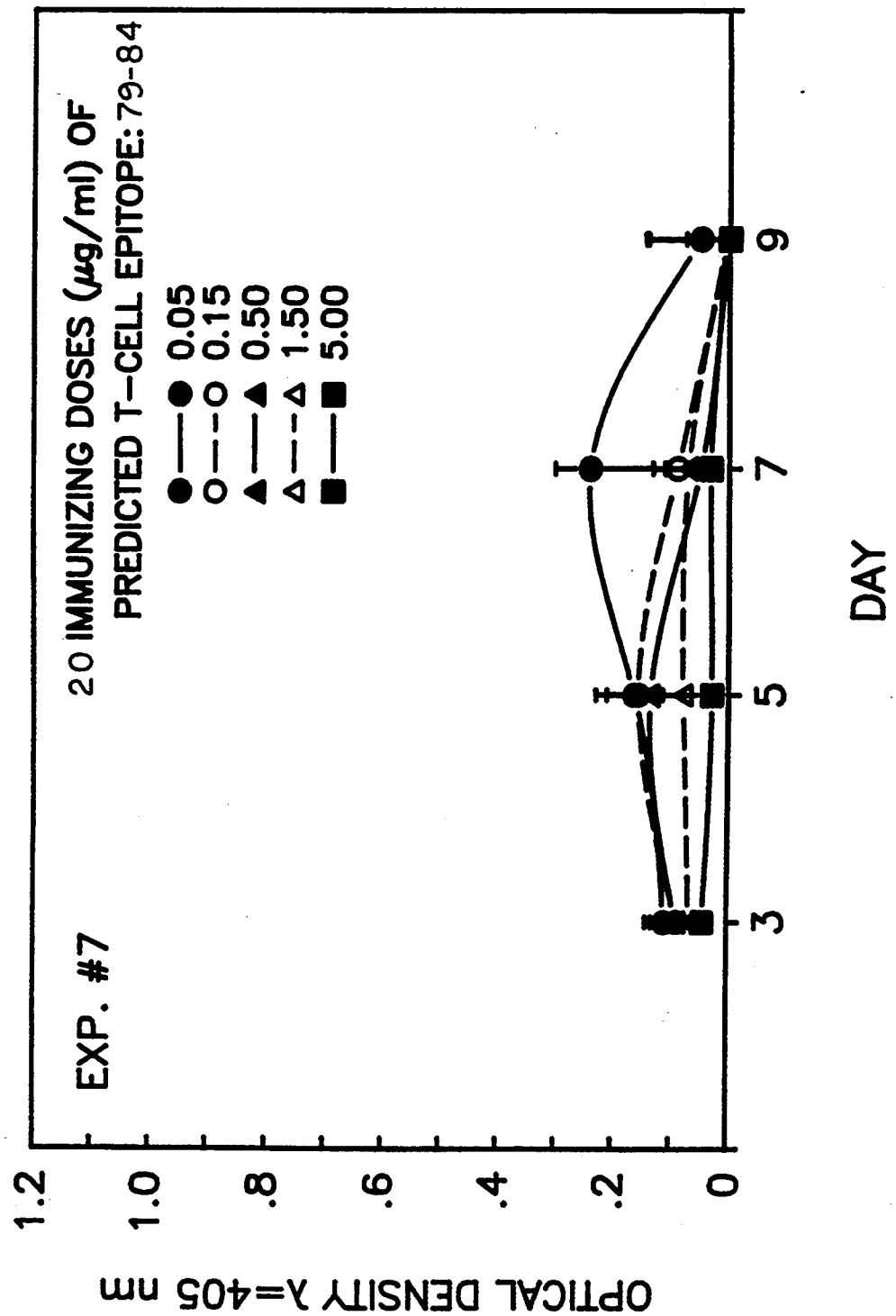

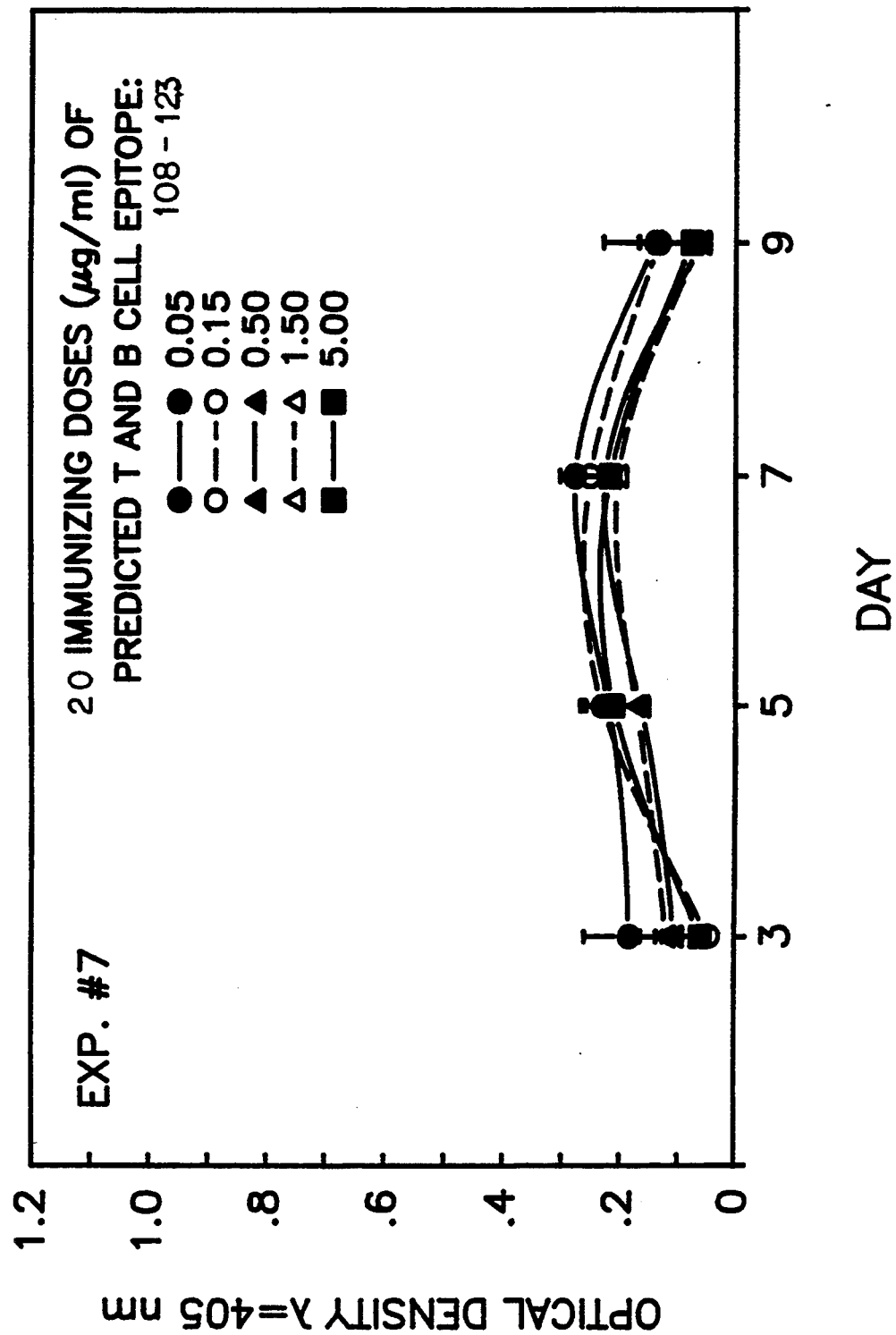

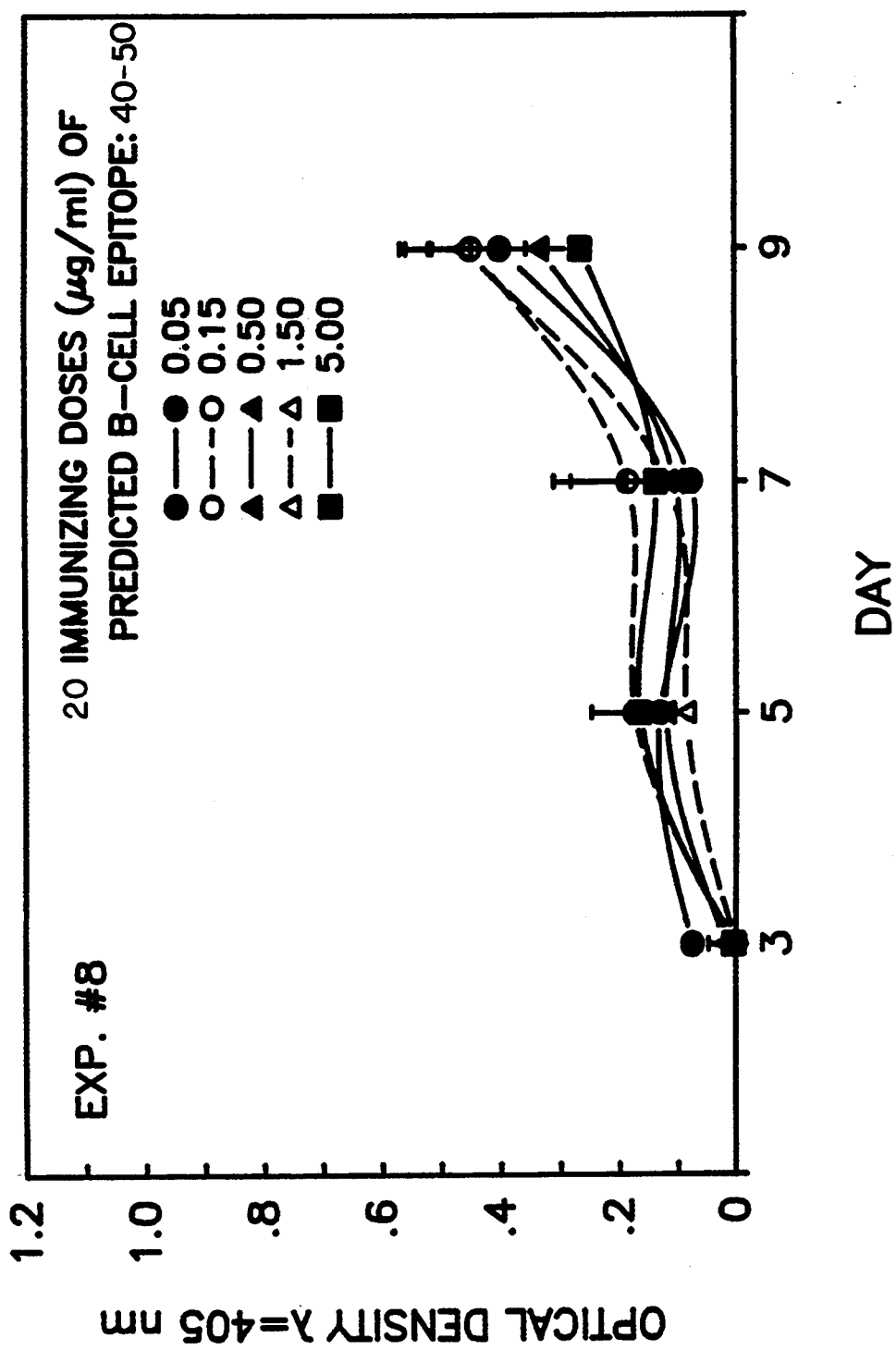

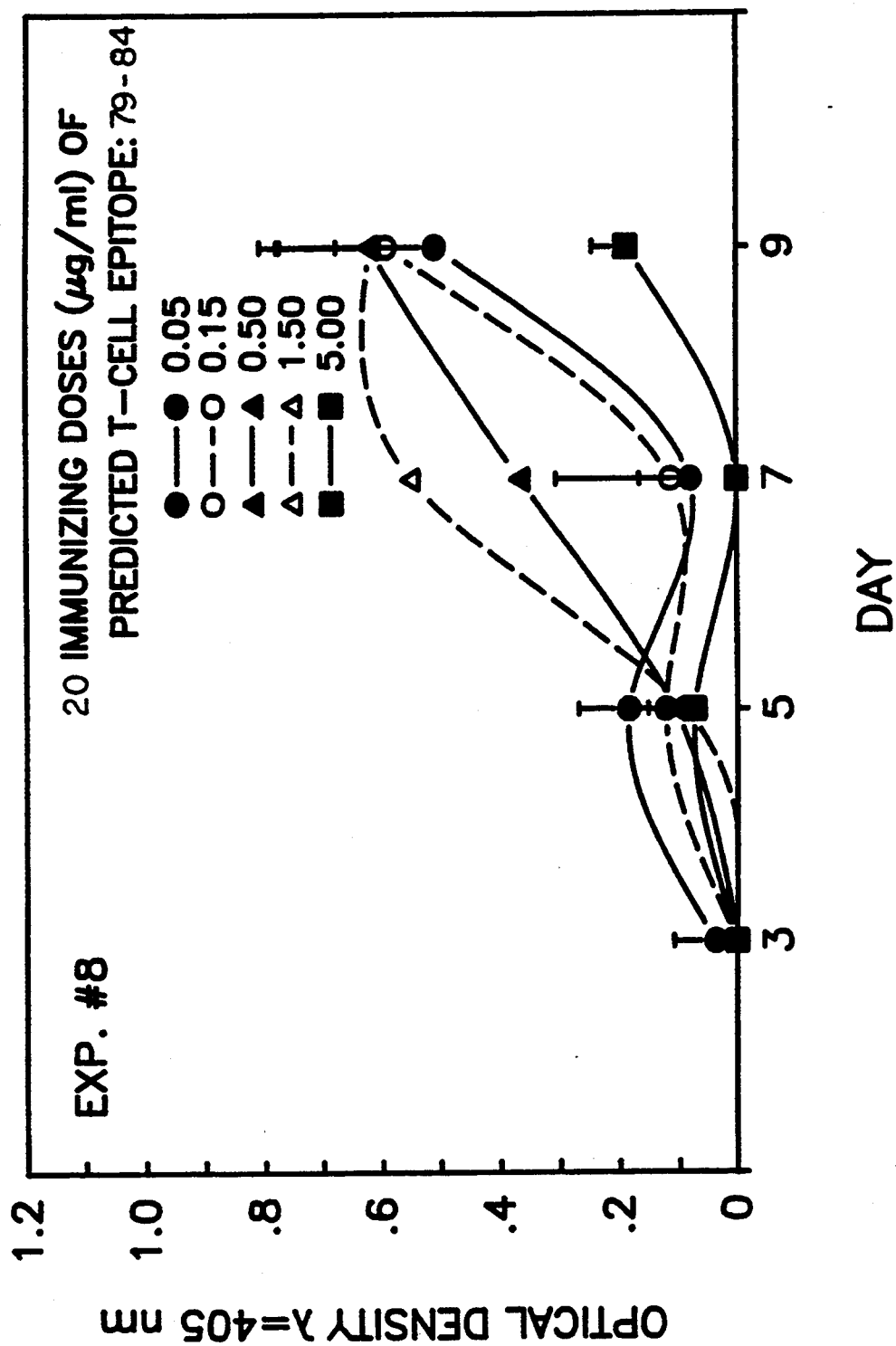

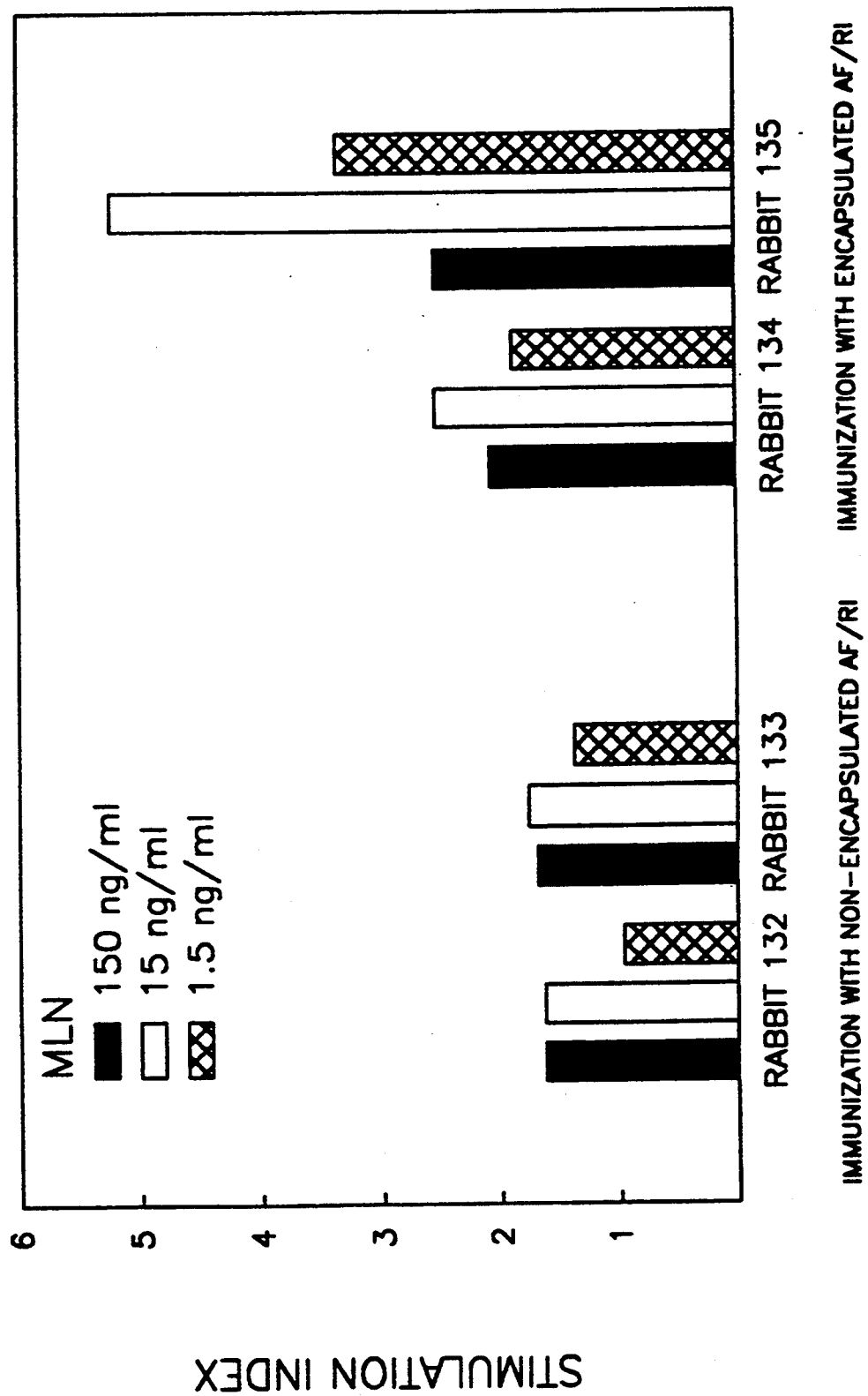

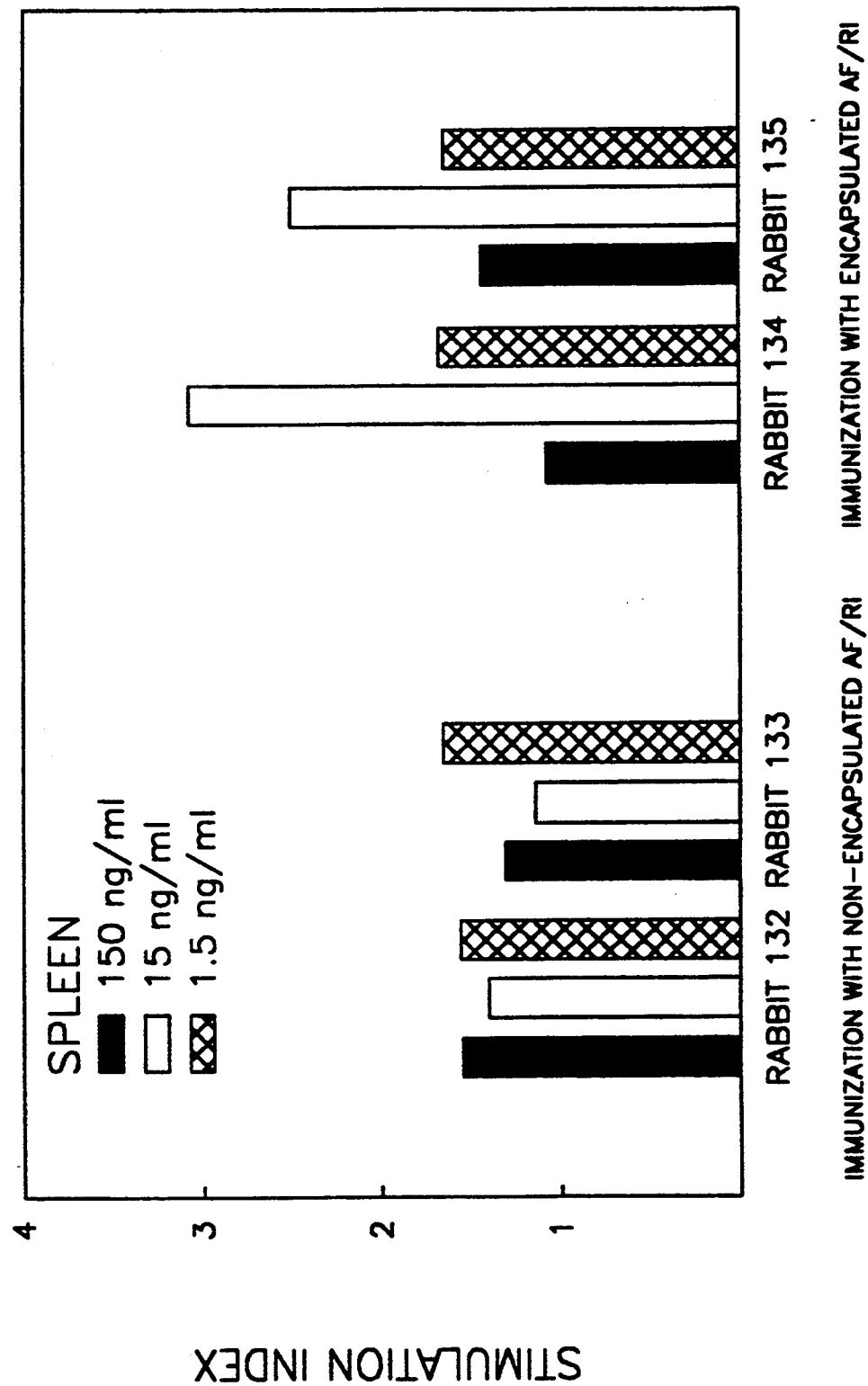

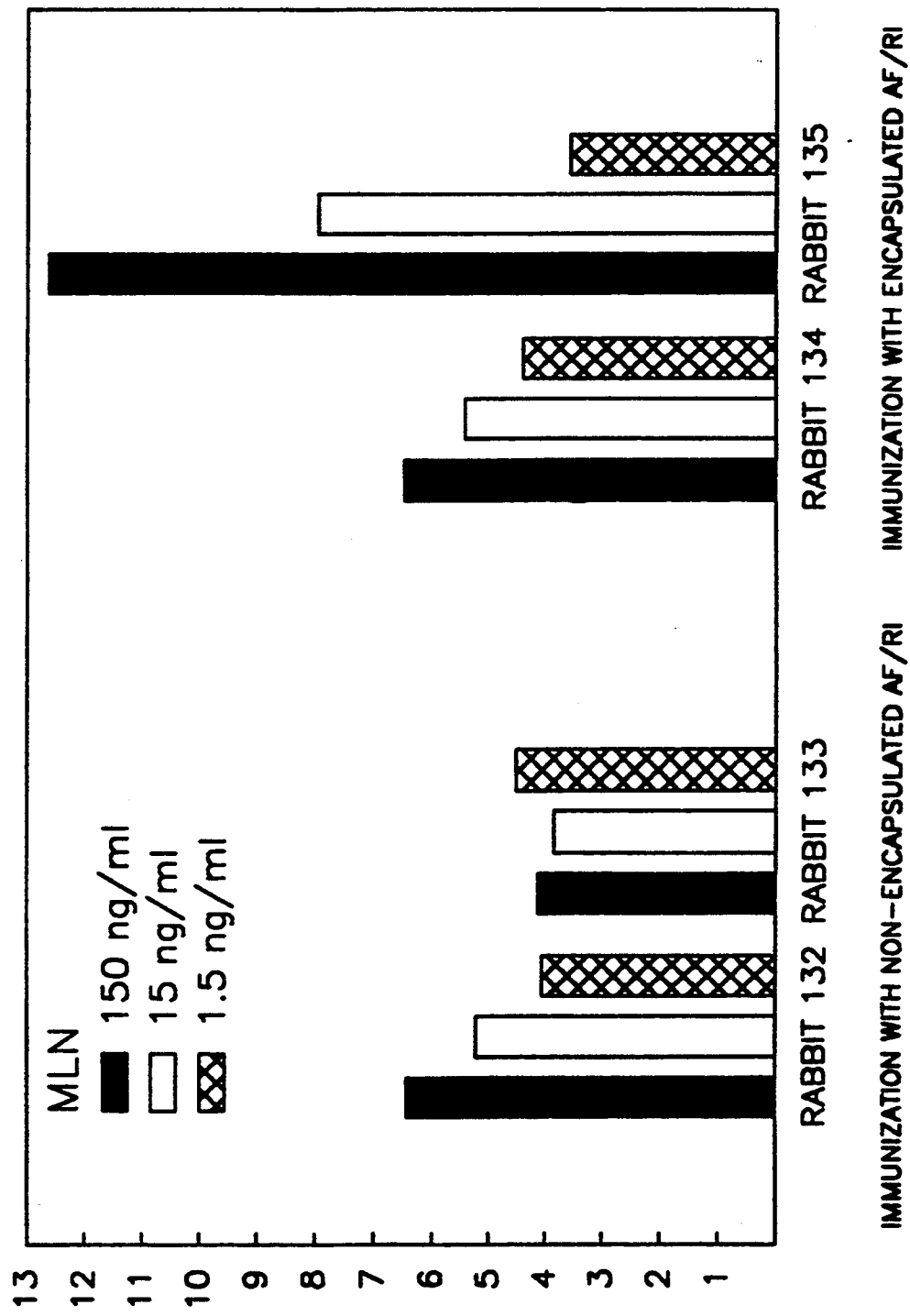

Lane 2  LADTPQLTDVLN<u>S</u>TVQMP  (62-79)

Lane 3  SYRVMTQVHTN<u>D</u>ATKKVIV  (42-60)

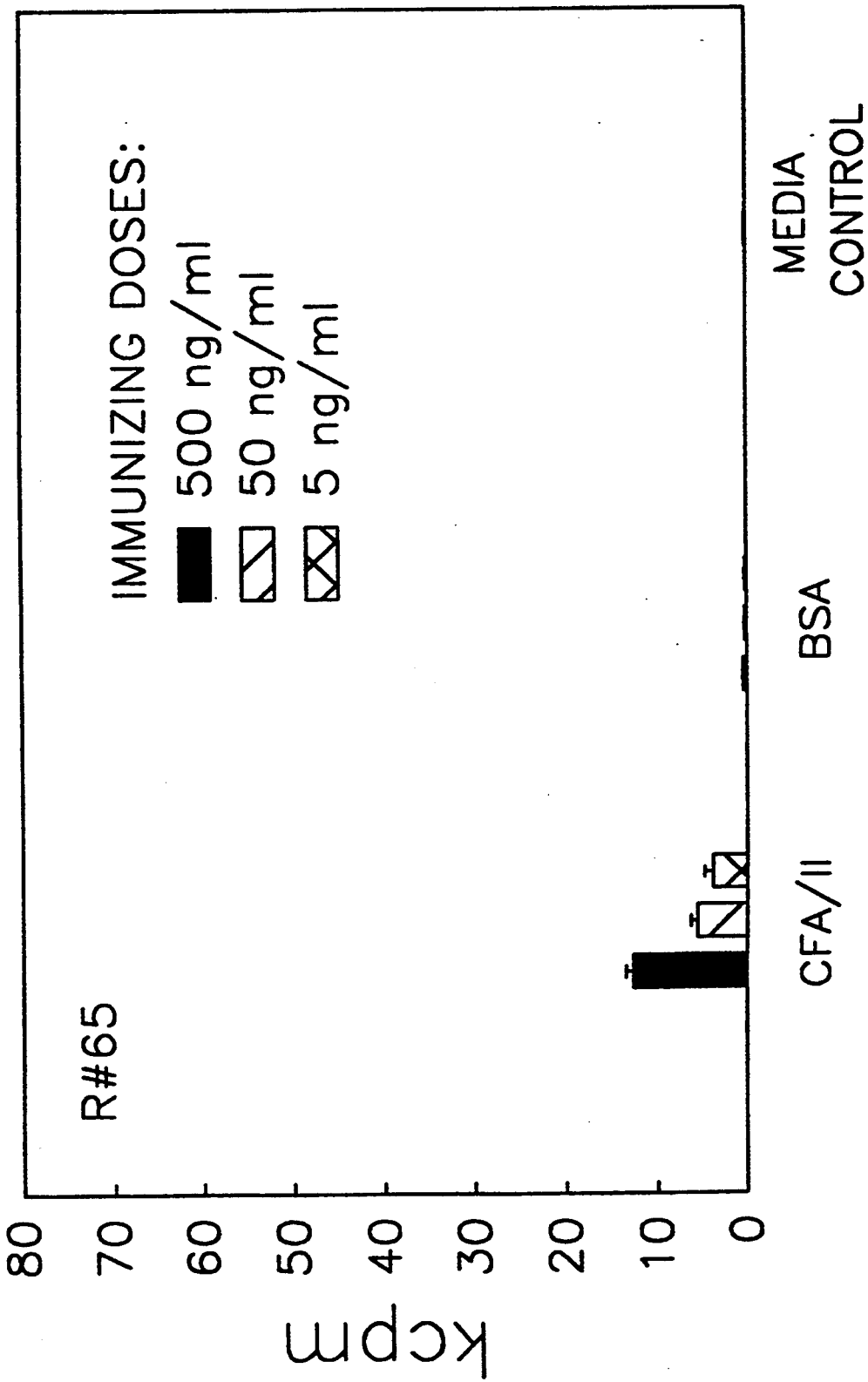

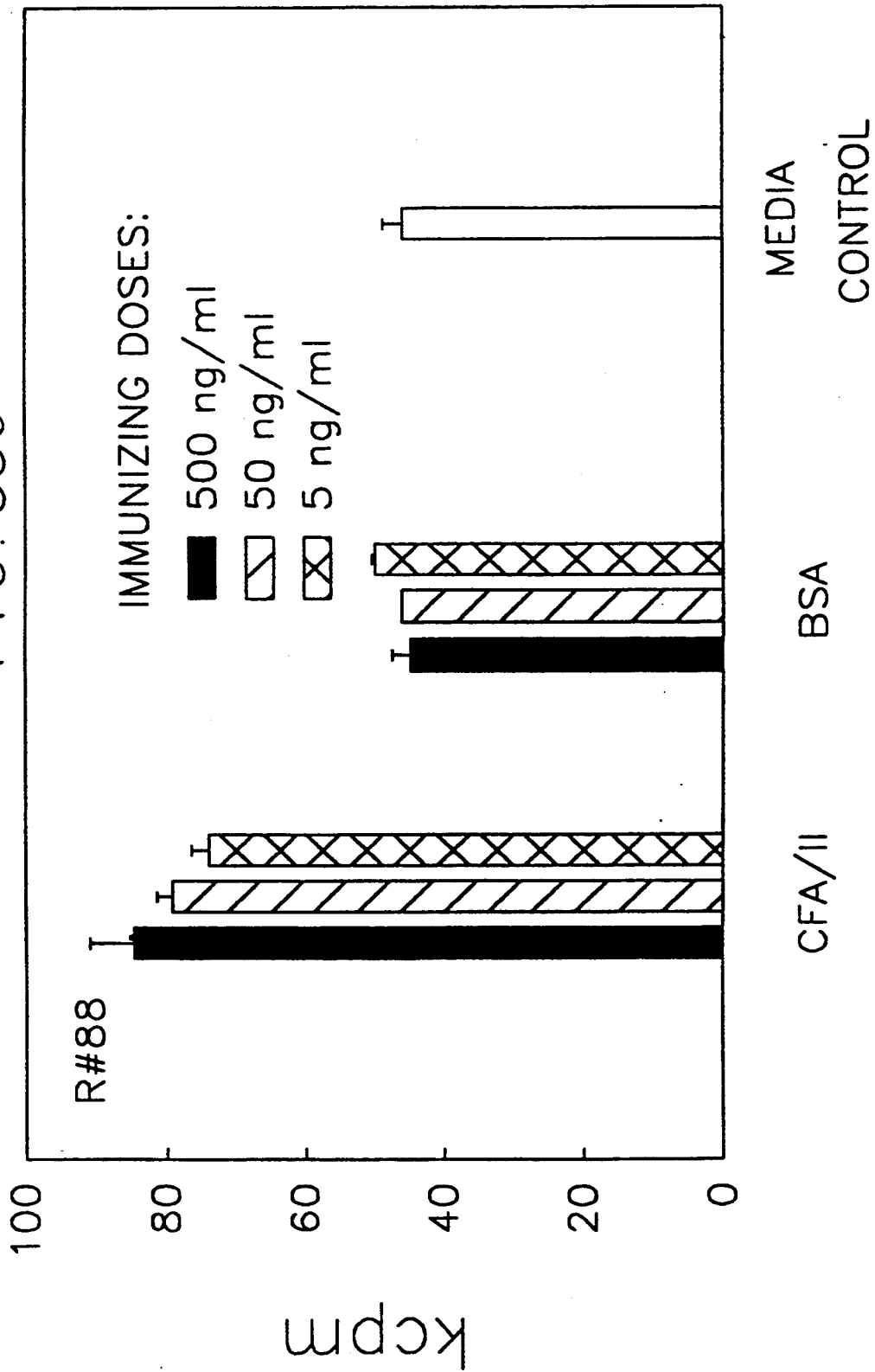

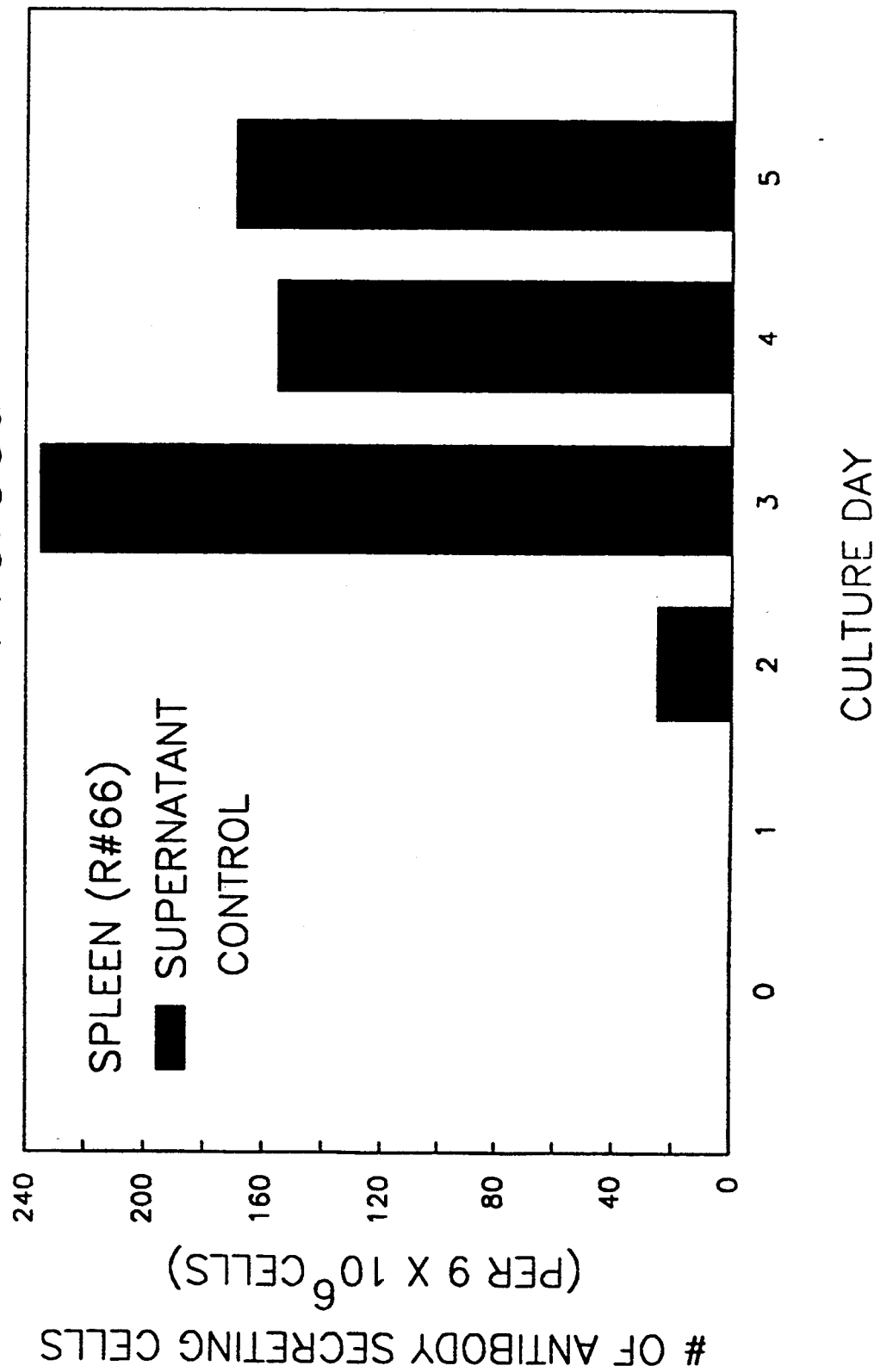

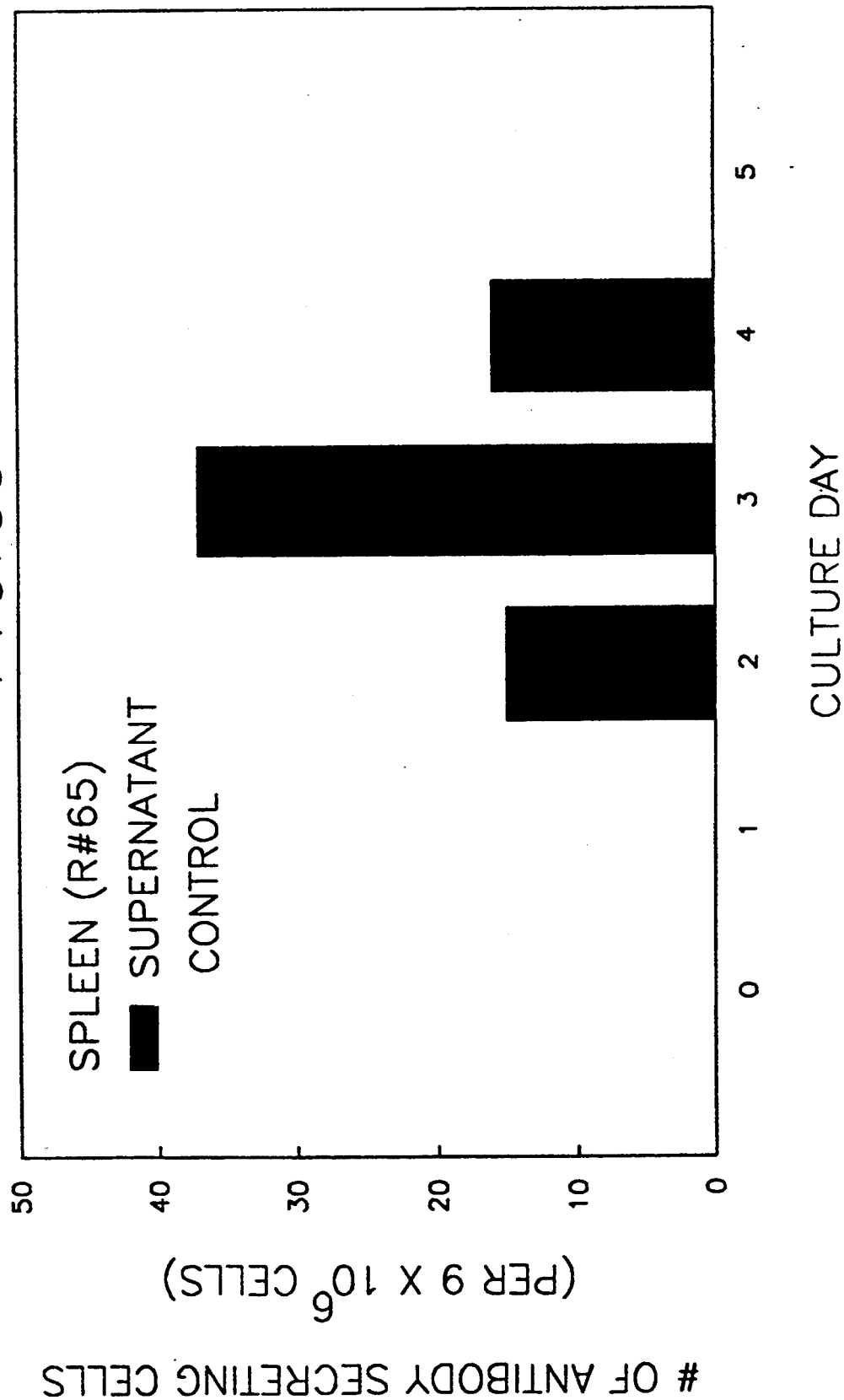

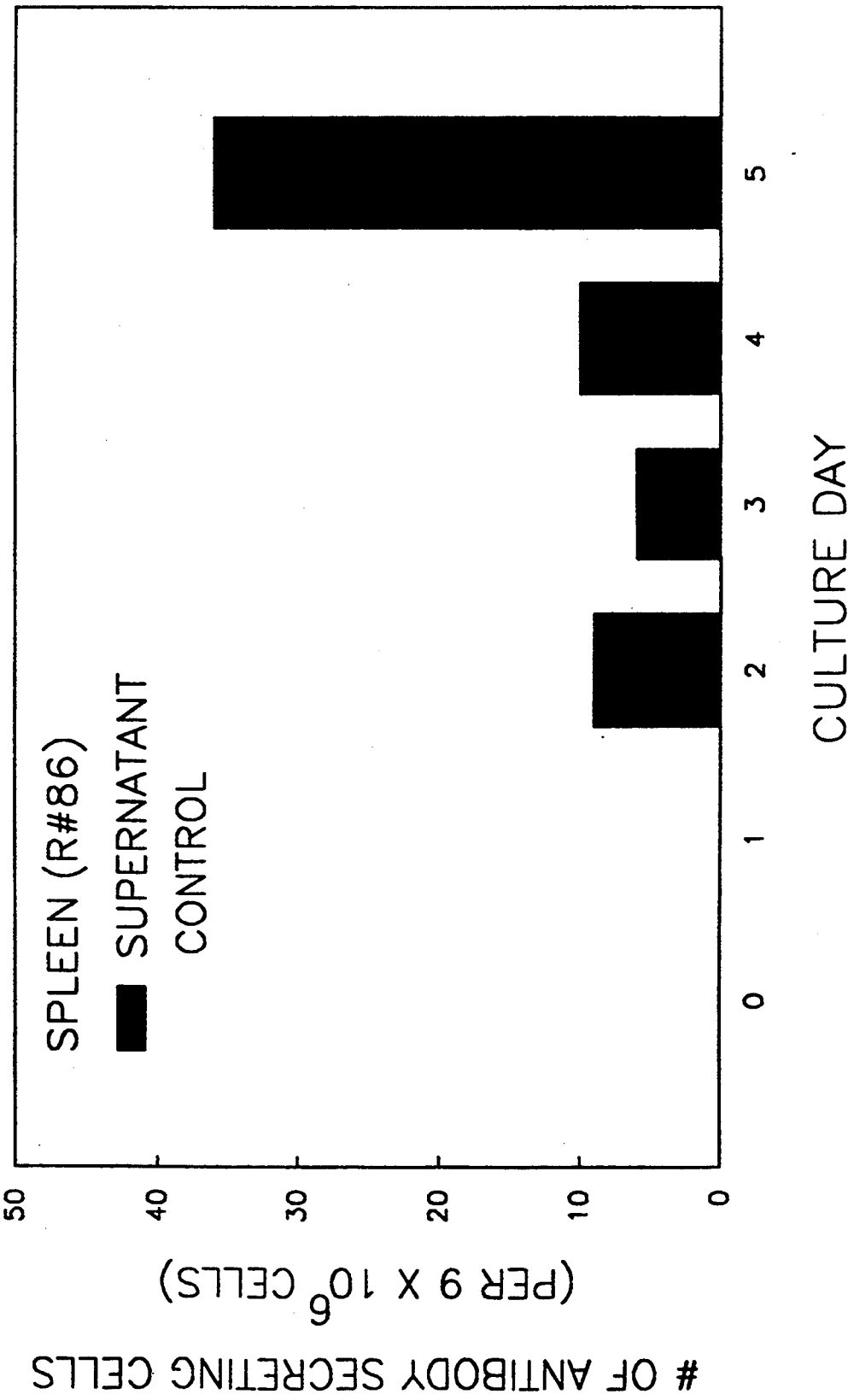

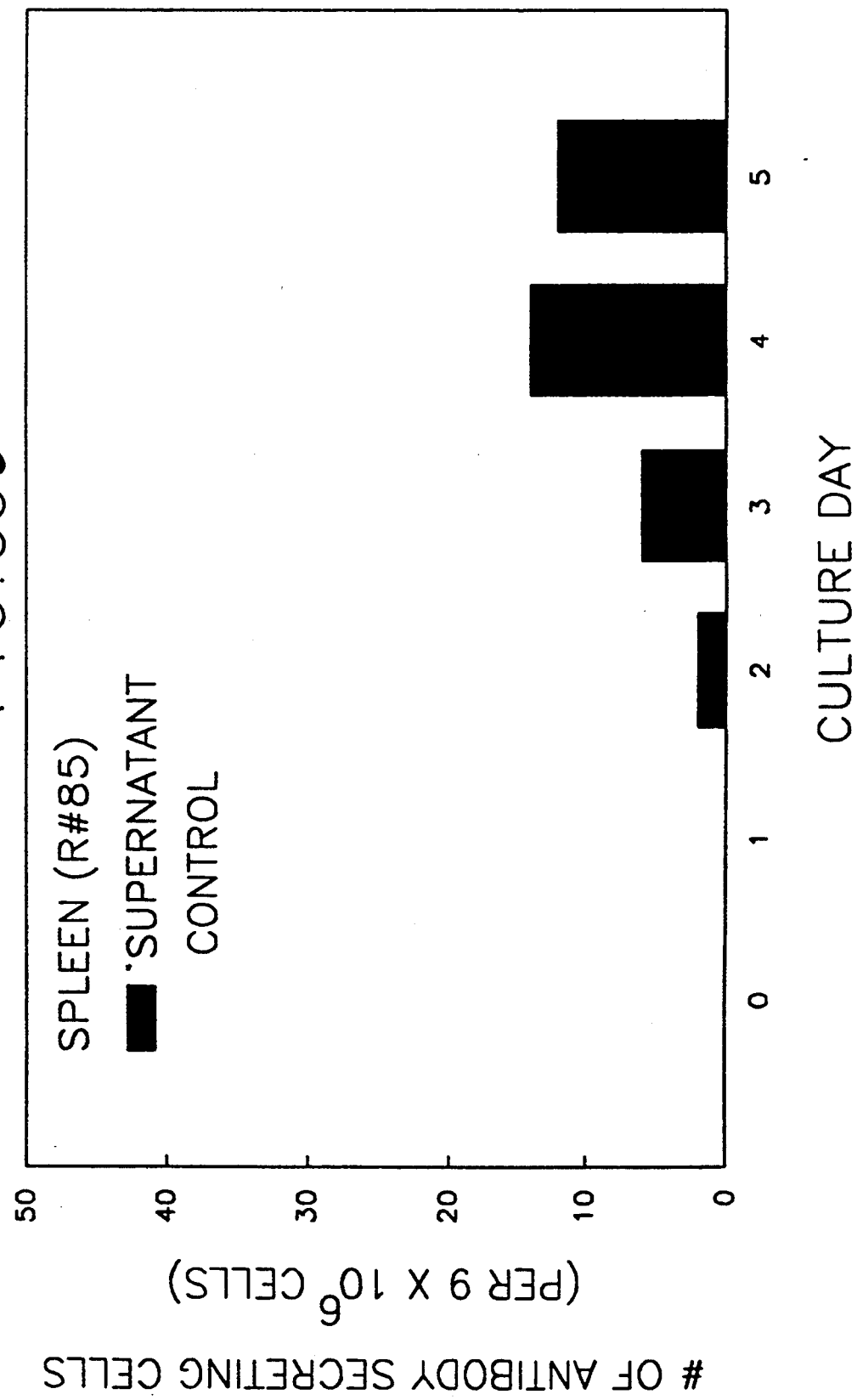

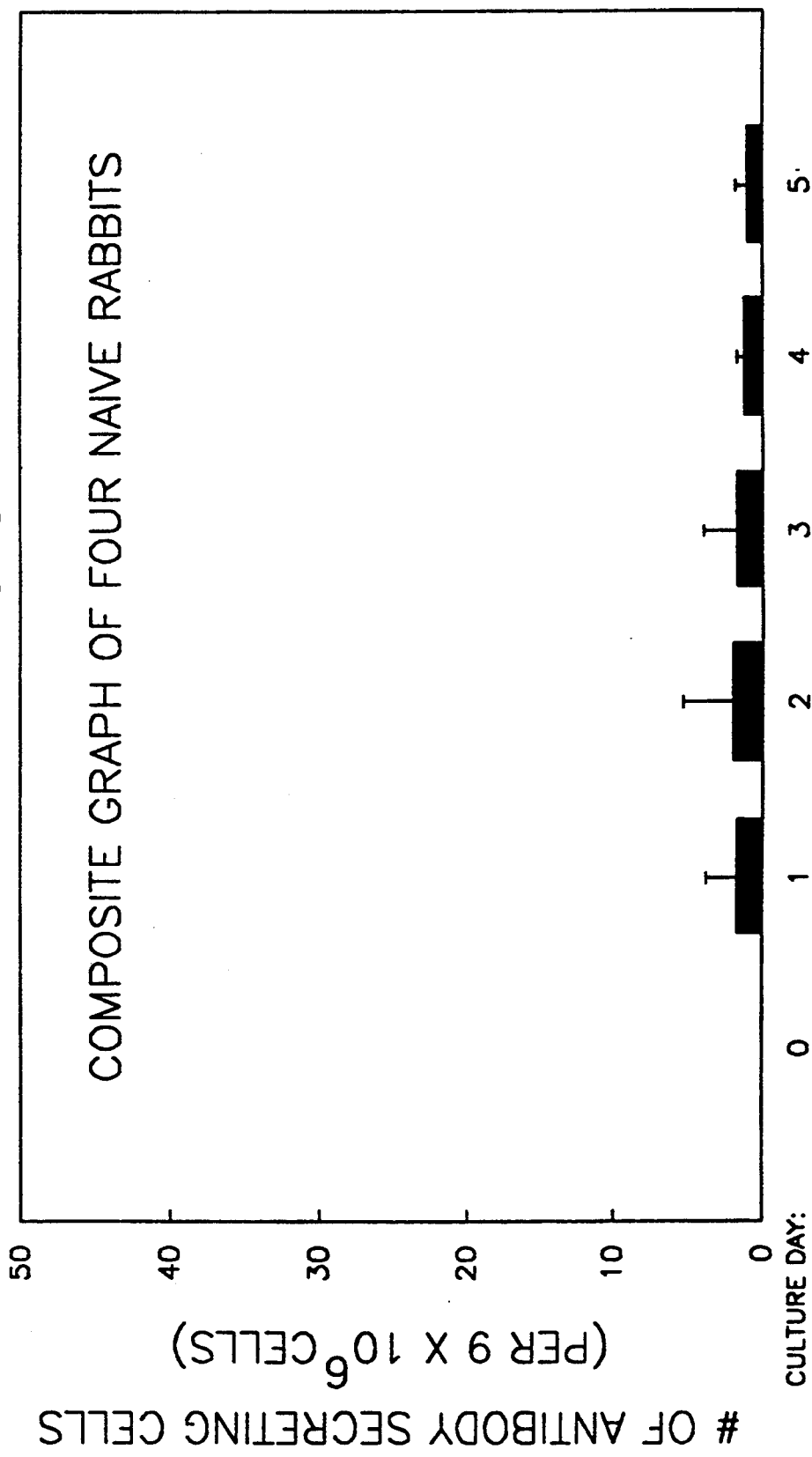

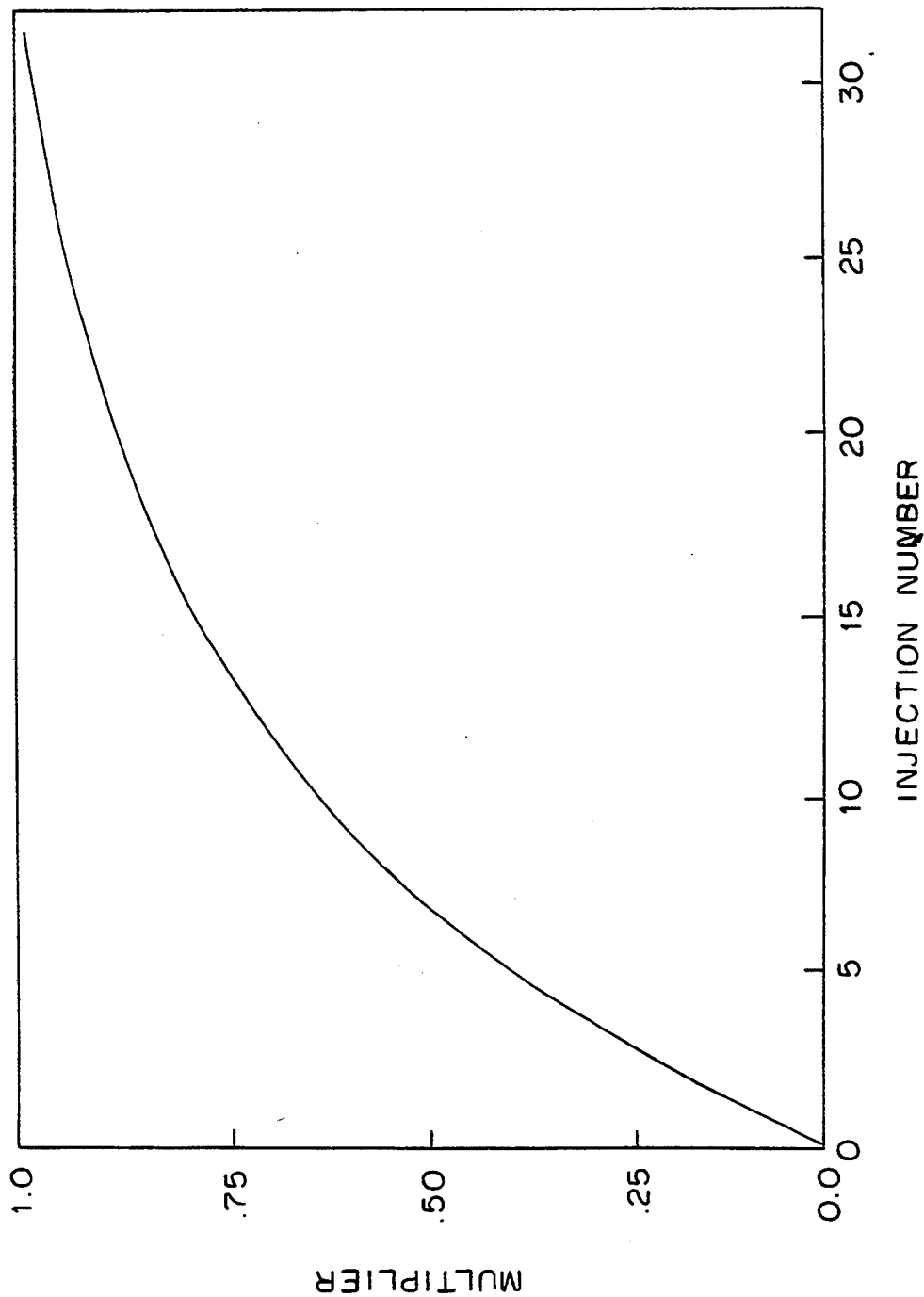

VACCINES AGAINST DISEASES CAUSED BY ENTEROPATHOGENIC ORGANISMS USING ANTIGENS ENCAPSULATED WITHIN BIODEGRADABLE-BIOCOMPATIBLE MICROSPHERES

I. GOVERNMENT INTEREST

The invention described herein may be manufactured, licensed and used by or for governmental purposes without the payment of any royalties to us thereon.

II. CROSS REFERENCE

This application is a continuation-in-part of U.S. patent application Ser. No. 07/805,721, filed Nov. 21, 1991, now abandoned, which in turn is a continuation-in-part of U.S. patent application Ser. No. 07/690,485, filed Apr. 24, 1991, now abandoned, which in turn is a continuation-in-part of U.S. patent application Ser. No. 07/521,945, filed May 11, 1990, now abandoned, which in turn is a continuation-in-part of U.S. patent application Ser. No. 07/493,597, filed Mar. 15, 1990, now abandoned, which in turn is a continuation-in-part of U.S. patent application Ser. No. 06/590,308, filed Mar. 16, 1984.

III. FIELD OF THE INVENTION

This invention relates to parenteral and oral-intestinal vaccines against diseases caused by enteropathogenic organisms using antigens encapsulated within biodegradable-biocompatible microspheres (matrix).

PHASE I

IV. BACKGROUND OF THE INVENTION

Most infectious agents have their first contact with the host at a mucosal surface; therefore, mucosal protective immune mechanisms are of primary importance in preventing these agents from colonizing or penetrating the mucosal surface. Numerous studies have demonstrated that a protective mucosal immune response can best be initiated by introduction of the antigen at the mucosal surface, and parenteral immunization is not an effective method to induce mucosal immunity. Antigen taken up by the gut-associated lymphoid tissue (GALT), primarily by the Peyer's patches in mice, stimulates T helper cell ($T_H$) to assist in IgA B cell responses or stimulates T suppressor cells ($T_S$) to mediate the unresponsiveness of oral tolerance. Particulate antigen appears to shift the response towards the ($T_H$) whereas soluble antigens favor a response by the ($T_S$). Although studies have demonstrated that oral immunization does induce an intestinal mucosal immune response, large doses of antigen are usually required to achieve sufficient local concentrations in the Peyer's patches. Unprotected protein antigens may be degraded or may complex with secretory IgA in the intestinal lumen.

One possible approach to overcoming these problems is to homogeneously disperse the antigen of interest within the polymeric matrix of appropriately sized biodegradable, biocompatible microspheres that are specifically taken up by GALT. Eldridge et. al. have used a murine model to show that orally-administered 1-10 micrometer microspheres consisting of polymerized lactide and glycolide, (the same materials used in resorbable sutures), were readily taken up into Peyer's patches, and the 1-5 micrometer size were rapidly phagocytized by macrophages. Microspheres that were 5-10 micrometers (microns) remained in the Peyer's patch for up to 35 days, whereas those less than 5 micrometer disseminated to the mesenteric lymph node (MLN) and spleen within migrating MAC-1+ cells. Moreover, the levels of specific serum and secretory antibody to staphylococcal enterotoxin B toxoid and inactivated influenza A virus were enhanced and remained elevated longer in animals which were immunized orally with microencapsulated antigen as compared to animals which recieved equal doses of non-encapsulated antigen. These data indicate that microencapsulation of an antigen given orally may enhance the mucosal immune response against enteric pathogens. AF/R1 pili mediate the species-specific binding of E. coli RDEC-1 with mucosal glycoproteins in the small intestine of rabbits and are therefore an important virulence factor. Although AF/R1 pili are not essential for E. coli RDEC-1 to produce enteropathogenic disease, expression of AF/R1 promotes a more severe disease. Anti-AF/R1 antibodies have been shown to inhibit the attachment of RDEC-1 to the intestinal mucosa and prevent RDEC-1 disease in rabbits. The amino acid sequence of the AF/R1 pilin subunit has recently been determined, but specific antigenic determinants within AF/R1 have not been identified.

Recent advances in the understanding of B cell and T cell epitopes have improved the ability to select probably linear epitopes from the amino acid sequence using theoretical criteria. B cell epitopes are often composed of a string of hydrophilic amino acids with a high flexibility index and a high probability of turns within the peptide structure. Prediction of T cell epitopes are based on the Rothbard method which identifies common sequence patterns that are common to known T cell epitopes or the method of Berzofsky and others which uses a correlation between algorithms predicting amphipathic helices and T cell epitopes.

In the current study we have used these theortical criteria to predict probable T or B cell epitopes from the amino acid sequence of AF/R1. Four different 16 amino acid peptides that include the predicted epitopes have been synthesized: AF/R1 40-55 as a B cell epitope, 79-94 as a T cell epitope, 108-123 as a T and B cell epitope, and AF/R1 40-47/79-86 as a hybrid of the first eight amino acids from the predicted B cell epitope and the T cell epitope. We have used these peptides as well as the native protein to stimulate the in vitro proliferation of lymphocytes taken from the Peyer's patch, MLN, and spleen of rabbits which have recieved intraduodenal priming with microencapsulated or nonencapsulatled AF/R1. Our results demonstrate the microencapsulation of AF/R1 potentiates the cellular immune response at the level of the Peyer's patch, thus enhancing in vitro lymphocyte proliferation to both the native protein and its linear peptide antigens. CFA/I pili, rigid thread-like structures which are composed of repeating pilin subunits of 147 amino acid found on serogroups 015, 025, 078, and 0128 of enterotoxigenic E. coli (ETEC) [1-4, 18]. CFA/I promotes mannose resistant attachment to human brush borders [5]; therefore, a vaccine that established immunity against this protein may prevent the attachment to host tissues and subsequent disease. In addition, because the CFA/I subunit shares N-terminal amino acid sequence homology with CS1, CFA/II (CS2) and CFA/IV (CS4) [4], a subunit vaccine which contained epitopes from this area of the molecule may protect against infection with various ETEC.

Until recently, experiments to identify these epitopes were time consuming and costly; however, technology is now available which allows one to simultaneously identify all the T cell and B cell epitopes in the protein of interest. Multiple Peptide synthesis (Pepscan) is a technique for the simultaneous synthesis of hundreds of peptides on polyethylene rods [6]. We have used this method to synthesize all the 140 possible overlapping actapeptides of the CFA/I protein. The peptides, still on the rods, can be used directly in ELISA assays to map B call epitopes [6, 12-14]. We have also synthesized all the 138 possible overlapping decapeptides of the CFA/I protein. For analysis of T cell epitopes, these peptides can be cleaved from the rods and used in proliferation assays [15]. Thus this technology allows efficient mapping and localization of both B cell and T cell epitopes to a resolution of a single amino acid [16]. These studies were designed to identify antigenic epitopes of ETEC which may be employed in the construction of an effective subunit vaccine.

CFA/I pili consist of repeating pilin protein subunits found on several serogroups of enterotoxigenic E. coli (ETEC) which promote attachment to human intestinal mucosa. We wished to identify areas within the CFA/I molecule that contain imunodominant T cell eptiopes that are capable of stimulating the cell-mediated portion of the immune response in primates as well as immunodominant B cell epitopes. To do this, we (a) resolved the discrepancy in the literature on the complete amino acid sequence of CFA/I, (b) immunized three Rhesus monkeys with multiple i.m. injections of purified CFA/I subunit in Freund's adjuvant, (c) synthesized 138 overlapping decapeptides which represented the entire CFA/I protein using the Pepscan technique (Cambridge Research Biochemicals), (d) tested each of the peptides for their ability to stimulate the spleen cells from the immunized monkeys in a proliferative assay (e) synthesized 140 overlapping octapeptides which respresented the entire CFA/I protein, and (f) tested serum from each monkey for its ability to recognize the octapeptides in a modified ELISA assay. A total of 39 different CFA/I decapeptides supported a significant proliferative response with the majority of the responses occurring within distinct regions of the protein (peptides beginning with residues 8-40, 70-80, and 127-137). Nineteen of the responsive peptides contained a serine residue at positions 2, 3, or 4 in the peptide, and a nine contained a serine specifically at position 3. Most were predicted to be configured as an alpha holix and have a high amphipathic index. Eight B cell epitopes were identified at positions 3-11, 11-21, 22-29, 32-40, 38-45, 66-74, 93-101, and 124-136. The epitope at position 11-21 was strongly recognized by all three individual monkeys, while the epitopes at 93-101, 124-136, 66-74, and 22-29 were recognized by two of the three monkeys.

V. SUMMARY OF THE INVENTION

This invention relates to a novel pharmaceutical compositon, a microcapsule/sphere formulation, which comprises an antigen encapsulated within a biodegradable polymeric matrix such as poly (DL-lactide-co-glycolide) (DL-PLG), wherein the relative ratio between the lactide and glycolide component of the DL-PLG is within the range of 52:48 to 0:100, and its use, as a vaccine, in the effective pretreatment of animals (including humans) to prevent intestinal infections caused by a virus or bacteria. In the practice of this invention, applicants found that the AF/R1 adherence factor is a plasmid encoded pilus composed of repeating pilin protein subunits that allows E. coli RDEC-1 to attach to rabbit intestinal brush borders. To identify an approach that enhances the immunogenicity of antigens that contact the intestinal mucosa, applicants investigated the effect of homogeneously dispersing AF/R1 pili within biodegradable microspheres that included a size range selected for Peyer's Patch localization. New Zealand White rabbits were primed twice with 50 micrograms of either microencapsulated or nonencapsulated AF/R1 by endoscopic intraduodenal inoculation. Lymphoid tissues were removed and cellular proliferative responses to AF/R1 and synthetic AF/R1 peptides were measured in vitro. The synthetic peptides represented possible T and/or B cell epitopes which were selected from the AF/R1 subunit sequence using theoretical criteria. In rabbits which had received nonencapsulated AF/R1, Peyer's Patch cells demonstrated slight but signifient proliferation in vitro in response to AF/R1 pili but not the AF/R1 synthetic peptides. In rabbits which had recieved microencapsulated AF/R1, Peyer's Patch cells demonstrated a markedly enhanced response to AF/R1 and the synthetic peptides. Cells from the spleen and mesenteric lymph nodes responded similarly to AF/R1 pili in both groups of animals, while there was a greater response to the synthetic peptide AF/R1 40-55 in rabbits that had received microencapsulated AF/R1. These data demonstrate that microencapsulation of AF/R1 potentiates the mucosal cellular immune response to both the native protein and its linear peptide antigens.

VI. BRIEF DESCRIPTION OF THE DRAWINGS

FIG. 1 shows the size destribution of microspheres wherein the particle size distibution (%) is (a) By number 1-5 (91) and 6-10 (9) and Co) By weight 1-5 (28) and 6-10 (72).

FIG. 2 shows a scanning electron micrograph of microspheres.

FIGS. 3(a) and (b) show the In vitro immunization of spleen cells and demonstrates that AF/RI pilus protein remains immunogenic to rabbit spleen cells immunized in vitro after microencapsulation. AF/R1 pilus protein has been found to be immunogenic for rabbit spleen mononuclear cells in vitro producing a primary IgM antibody response specific to AF/RI. Immunization with antigen encapsulated in biodegradable, biocompatible microspheres consisting of lactide/glycolide copolymers has been shown to endow substantially enhanced immunity over immunization with the free antigen. To determine if microencapsulated AF/RI maintains the immunogenicity of the free pilus protein, a primary in vitro immunization assay was conducted. Rabbit spleen mononuclear cells at a concentration of $3 \times 10^5$ cells/well. Triplicate wells of cells were immunized with free AF/RI in a dose range from 15 to 150 ng/ml or with equivalent doses of AF/RI contained in microspheres. Supernatants were harvested on days 7, 9, 12, and 14 of culture and were assayed for free AF/RI pilus protein specific IgM antibody by the ELISA. Supernatant control values were subtracted from those of the immunized cells. Cells immunized with free pilus protein showed a significant positive IgM response on all four days of harvest, with the antibody response increasing on day 9, decreasing on day 12, and increasing again on day 14. Cells immunized with microencapsulated pilus protein showed a comparable positive IgM antibody response as cells immunized with free pilus protein. In conclusion, AF/RI maintains immunogenicity to rabbit spleen cells immunized in vitro after microencapsulation.

FIGS. 4(a) and (b) show in vitro immunization of Peyer's patch cells. Here the AF/RI pilus protein remains immunogenic to rabbit Peyer's patch cells immunized in vitro after microencapsulation. AF/RI pilus protein has been found to be immunogenic for rabbit Peyer's patch mononuclear cells in vitro producing a primary IgM antibody response specific to AF/RI. Immunization with antigen encapsulated in biodegradable, biocompatible microspheres consisting of lactide/-glycolide copolymers has been shown to endow substantially enhanced immunity over immunization with the free antigen. To determine if microencapsulated AF/RI maintains the immunogencity of the free pilus protein, a primary in vitro immunization assay was conducted. Rabbit Peyer's patch mononuclear cells at a concentration of $3\times10^6$ cells/ml were cultured in 96-well, round bottom microculture plates at a final concentration of $6\times10^5$ cells/well. Triplicate wells of cells were immunized with free AF/RI in a dose range from 15 to 150 ng/ml or with equivalent dose of AF/RI contained in microspheres. Supernatants were harvested on days 7, 9, 12, and 14 of culture and were assayed for free AF/RI pilus protein specific IgM antibody by the ELISA. Supernatant control values were subtracted from those of the immunized cells. Cells immunized with free pilus protein showed a significant positive IgM response on all four days of harvest, with the highest antibody response on day 12 with the highest antigen dose. Cells immunized with encapsulated pilus protein showed a positive response on day 12 with all three antigen doses. In conclusion, AF/RI pilus protein maintains immunogenicity to rabbit Peyer's patch cells immunized in vitro after microencapsulation.

FIG. 5 shows proliferative responses to AF/RI by rabbit Peyer's patch cells. Naive rabbits were primed twice with 50 micrograms of either non-encapsulated (rabbits 132 and 133) or microencapsulated (rabbits 134 and 135) AF/RI pili by endoscopic intraduodenal inoculation seven days apart. Seven days following the second priming, Peyer's patch cells were cultured with AF/RI in 96-well plates for four days followed by a terminal six hour pulse with [$^3$H]thymidine. Data shown is the SI calculated from the mean cpm of quadruplicate cultures. Responses were significant for all rabbits: 132 ($p=0.013$), 133 ($p=0.0006$), 134 ($p=0.0016$), and 135 ($p=0.0026$). Responses were significantly different between the two groups. Comparison of the best responder in the nonencapsulated antigen group (rabbit 133) with the lowest responder in the microencapsulated antigen group (rabbit 134) demonstrated an enhanced response when the immunizing antigen was microencapsulated ($p=0.0034$).

Additionally, FIG. 5 relates to the in vitro lymphocyte proliferation after sensitization of rabbit lymphoid tissues with encapsulated or non-encapsulated AF/RI pilus adhesion of *E. coli* strain RDEC-1. The AF/RI adherence factor is a plasmid encoded pilus protein that allows RDEC-1 to attach to rabbit intestinal brush borders. We investigated the immunopotentiating effect of encapsulating purified AF/RI into biodegradable nonreactive microspheres composed of polymerized lactide and glycolide, materials used in resorbable sutures. The microspheres had a size range of 5–10 microns, a size selected for Peyer's Patch localizaiton, and contained 0.62% protein by weight. NZW rabbits were immunized twice with 50 micrograms of either encapsulated or non-encapsulated AF/RI by intraduodenal later of non-encapsulated AF/RI by intraduodenal inoculation seven days apart. Lymphocyte proliferation in respone to purified AR/RI was conducted in vitro at seven days and showed that encapsulating the antigen into microspheres enhanced the cellular immune response in the Peyer's Patch; however, no significant increase was observed in spleen or mesenteric lymph node. These data suggest that encapsulation of AF/RI may potentiate the mucosal cellular immune response.

FIGS. 6*a–d* show proliferative responses to AF/RI synthetic peptides by rabbit Peyer's patch cells. Naive rabbits were primed twice with 50 micrograms of either non-encapsulated (rabbits 132 and 133) or microencapsulated (rabbits 134 and 135) AF/RI pili by endoscopic intraduodenal inoculation seven days apart. Seven days following the second priming, Peyer's patch cells from each rabbit were cultured with AF/R1 40–55 (FIG. 6*a*), AF/R1 79–94 (FIG. 6*b*), AF/R1 108–123 (FIG. 6*c*), or AF/R1 40–47/79–86 (FIG. 6*d*) in 96-well plates for four days followed by a terminal six hour pulse with [$^3$H]thymidine. Data shown is the SI calculated from the mean cpm of quadruplicate cultures. The responses of rabbits 132 and 133 were not significant to any of the peptides tested. Rabbit 134 had a significant response to (a) AF/R1 40–55 ($p=0.0001$), (b) AF/R1 79–94 ($p=0.0280$), and (d) AF/R1 40–57/79–86 ($p=0.025$), but not to (c) AF/R1 108–123. Rabbit 135 had a significant response to (a) AF/R1 40–55 ($p=0.034$), (b) AF/R1 79–94 ($p=0.040$), and (c) AF/R1 108–123 ($p<0.0001$), but not to (d) AF/R1 40–47/79–86. This demonstrates enhanced proliferative response to peptide antigens following mucosal priming with microencapsulated pili. AF/RI pili promotes RDEC-1 attachment to rabbit intestinal brush borders. Three 16 amino acid peptides were selected by theoretical criteria from the AF/RI sequence as probable T or B cell epitopes and were synthesized: AF/RI 40–55 as a B cell epitope, 79–94 as a T cell epitope, and 108–123 as a T and B cell epitope. We used these peptides to investigate a possible immunopotentiating effect of encapsulating purified Af/RI pili into biodegradable, biocompatible microspheres composed of polymerized lactide and glycolide at a size range that promotes localization in the Peyer's Patch (5–10 micrometers). NZW rabbits were primed twice with 50 micrograms AF/RI by endoscopic intraduadenal inoculation and their Peyer's Patch cells were cultured in vitro with the AF/RI peptides. In two rabbits which had received encapsulated AF/RI, lymphocyte proliferation was observed to AF/RI 40–55 and 79–94 in both rabbits and to 108–123 in one of two rabbits. No responses to any of the peptides were observed in rabbits which received non-encapsulated AF/RI. These data suggest that encapsulation of AF/RI may enhance the cellular response to peptide antigens.

FIGS. 7*a–d* show B-cell responses of Peyer's patch cells to AF/R1 and peptides.

FIGS. 8*a–d* show B-cell responses of Peyer's Patch cells to AF/R1 and peptides.

FIGS. 9*a–d* show B-cell responses of spleen cells to AF/R1 and Peptides.

FIGS. 10a–d show B cell responses of spleen cells to AF/R1 and peptides.

FIGS. 7 through 10, illustrate enhanced lymphocyte antibody response by mucosal immunization of rabbits with microencapsulated AF/R1 pilus protein. The AF/RI pilus protein has been found to be immunogenic for rabbit spleen and Peyer's patch cells in vitro producing a primary IgM antibody response. The purpose of this study was to determine if AR/R1 pilus protein immune response is enhanced by microencapsulation. The AF/R1 was incorporated into biodegradable, biocompatible microspheres composed of lactide-glycolide copolymers, had a size range of 5–10 micrometer and containing 0.62% pilus protein by weight. Initially, NZW rabbits were immunized twice with 50 micrograms of either encapsulated or non-encapsulated AF/RI via intraduodenal route seven days apart. For in vitro challenge, $6 \times 10^5$ rabbit lymphocytes, were set in microculture at final volume of 0.2 ml. Cells were challenged with AR/RI or three different synthetic 16 amino acid peptides representing, either predicted T, B or T and B cell epitopes in a dose range of 15 to 150 ng/ml for splenic cells or 0.05 to 5.0 micrograms/ml for Peyer's patch mononuclear cells (in triplicate). Supernatants were collected on culture days 3, 5, 7, and 9 assayed by ELISA for anti-AF/R1 antibody response as compared to cell supernatant control. Significant antibody responses were seen only from spleen and Peyer's patch cells from rabbits immunized with microencapsulated AF/R1. The antibody response tended to peak between days 5 and 9 was mainly an IgM response. The results for the predicted epitopes were similar to those obtained with purified AF/RI. In conclusion, intestinal immunization with AF/RI pilus protein contained within microspheres greatly enhances both the spleen and Peyer's patch B-cell responses to predicted T & B-cell epitopes.

FIG. 11 shows proliferative responses to AF/R1 40–55 by rabbit MLN cells. Naive rabbits were primed twice with 50 micrograms of either nonencapsulated (rabbits 132 and 133) or microencapsulated (rabbits 134 and 135) AF/R1 pili by endoscopic intraduodenal inoculation seven days apart. Seven days following the second priming, MLN cells were cultured with AF/R1 40–55 for four days in 24-well plates. Cultures were transferred into 96-well plates for a terminal [$^3$H]thymidine pulse. Data shown is the SI calculated from the mean cpm of quadruplicate cultures. Responses of rabbits 132 and 133 were not statistically significant. Responses were significant for rabbits 134 ($p=0.0.0051$) and 135 ($p=0.0055$).

FIG. 12 shows proliferative responses to AF/R1 40–55 by rabbit spleen cells. Naive rabbits were primed twice with 50 micrograms of either nonencapsulated (rabbits 132 and 133) or microencapsulated (rabbits 134 and 135) AF/R1 pili by endoscopic intraduodenal inoculation seven days apart. Seven days following the second priming, spleen cells were cultured with AF/R1 40–55 for four days in 24-well plates. Cultures were transferred into 96 well plates for a terminal [$^3$H]thymidine pulse. Data shown is the SI calculated from the mean cpm of quadruplicate cultures. Responses of rabbits 132 and 133 were not statistically significant. Responses were significant for rabbits 134 ($p=0.0.0005$) and 135 ($p=0.0066$).

FIG. 13 shows proliferative responses to AF/R1 pili by rabbit spleen and mesenteric lymph node cells. A rabbit with preexisting high levels of anti-AF/R1 serum IgG was boosted twice by injection of 50 ug of purified AF/R1 pili i.p. seven days apart. A week after the final boost, spleen and mesenteric lymph node cells were stimulated with AF/R1 in 24-well plates. Cultures were transferred into 96-well plates for a terminal [$^3$H]thymidine pulse. Data shown is the mean cpm of quadruplicate cultures$+/-$SD. Responses were significant for both the spleen ($p<0.0001$) and the mesenteric lymph node ($p=0.0003$).

FIG. 14 shows proliferative responses to AF/R1 synthetic peptides by rabbit spleen cells. Spleen cells from the AF/R1 immune rabbit described in FIG. 13 were stimulated with AF/R1 synthetic peptides in 96-well plates for four days followed by a terminal six hour pulse with [$^3$H]thymidine. Data shown is the mean cpm of quadruplicate cultures$+/-$SD. Responses were significant for all peptides: AF/R1 40–55 ($p=0.0022$), AF/R1 79–94 ($p=0.018$), AF/R1 108–123 ($p=0.018$), and AF/R1 40–47/79–86 ($p=0.0006$).

FIG. 15 shows proliferative responses to AF/R1 by rabbit mesenteric lymph node cells. Naive rabbits were primed twice with 50 ug of either non-encapsulated (rabbits 132 and 133) or microencapsulated (rabbits 134 and 135) AF/R1 pili by endoscopic intraduodenal inoculation seven days apart. Seven days following the second priming, mesenteric lymph node cells were cultured for four days with AF/R1 in 24-well plates. Cultures were transferred into 96-well plates for a terminal [$^3$H]thymidine pulse. Data shown is the SI calculated from the mean cpm of quadruplicate cultures. Responses were significant for all rabbits: 132 ($p=0.0001$), 133 ($p<0.0001$), 134 ($p=0.0005$), and 135 ($p<0.0001$).

FIG. 16. A. SDS-PAGE of intact CFA/I (lane 1), trypsin treated CFA/I (lane 2), and S. aureus V8 protease treated CFA/I. Molecular masses of individual bands were estimated from molecular weight standards (on left). Multiple lanes of both trypsin and V8 treated CFA/I were transferred to PVDF membranes where bands corresponding to the approximate molecular masses of 3500 (trypsin digest, see arrow lane 2) and 6000 (V8 digest, see arrow lane 3) were excised and subjected to Edman degradation. B. Resulsting sequence of protein fragments from each lane of A (position of sequenced portion of fragment in the intact protein. Underlined, italisized residues are amino acids under dispute in literature.

FIG. 17. ELISA assay results testing hyperimmune sera of monkeys (A) 2Z2 (monkey 3), (B) 184 (D) (monkey 1) and (C) 34 (monkey 2) to CFA/I primary structure immobilized on polyethylene pins. Monkey sera diluted 1:1000. Peptide number refers first amino acid in sequence of octapeptide on pin from CFA/I primary structure OD 405 refers to optical density wavelength at which ELISA plates were reat (405 nm).

FIG. 18. Complete sequence of CFA/I (147 amno acids) with B cell recognition site (boxed areas) as defined by each individual monkey response (2Z2, 184D, and 34). Derived from data in FIG. 17.

FIGS. 19–21. Lymphocyte proliferation to synthetic decapeptides of CFA/I. Each monkey was immunized with three i.m. injections of CFA/I subunits in adjuvant, and its spleen cells were cultured with synthetic decapeptides which had been constructed using the Pepscan technique. The decapeptides represented the entire CFA/I protein. Concentrations of synthetic peptide used included 6.0, 0.6, and 0.06 micrograms/ml. Values shown represent the maximum proliferative response produced by any of the three concentrations of antigen used±the standard deviation. The cpm of the control peptide for each of the three monkeys was 1,518±50, 931±28, and 1,553±33 respectively. The cpm of the media control for each of the three monkeys was 1,319±60, 325±13, and 1,951±245 respectively.

FIGS. 22–24. Lymphocyte proliferation to 6.0, 0.6, and 0.06 micrograms/ml synthetic decapeptides of CFA/I in one monkey. The monkey (2Z2) as immunized with three i.m. injections of CFA/I subunits in adjuvant, and its spleen cells were cultured with synthetic decapeptides which had been constructed using the Pepscan technique. The decapeptides represented the entire CFA/I protein. Values shown represent the proliferative response which occurred to 6.0 micrograms/ml (FIG. 22), 0.6 micrograms/ml (FIG. 23), or 0.06 micrograms/ml (FIG. 24) of antigen±the standard deviation. The cpm of the control peptide was 1,553±33 and the cpm of the media control was 1,951±245.

FIG. 25 shows that rabbits numbers 21 and 22 received intraduodual administration of AF/R1 microspheres at doses of AF/R1 of 200 micrograms (ug) on day 0 and 100 ug on day 7, 14, and 21 then sacrificed on day 31. The spleen, Peyer's patch and ileal lamina propria cells at $6 \times 10^5$ in 0.2 ml in quadriplate were challenged with AF/RI and AF/R1 1-13, 40-55, 79-94, 108-123, and 40-47, 79-85 synthetic peptides at 15, 1.5 and 0.15 ug/ml for 4 days. The supernatants were tested for IL-4 using the IL-4/IL-2 dependent cell line cells CT4R at 50,000/well with 0.1 ml of 6.25% supernatant for 3 days then pulsed with tritiated thymidine for 4 hrs, cells harvested and the tritiated thymidine incorporation determined, averaged and expressed with one standard deviation thousand counts per minute (kcpm).

Figure 29:
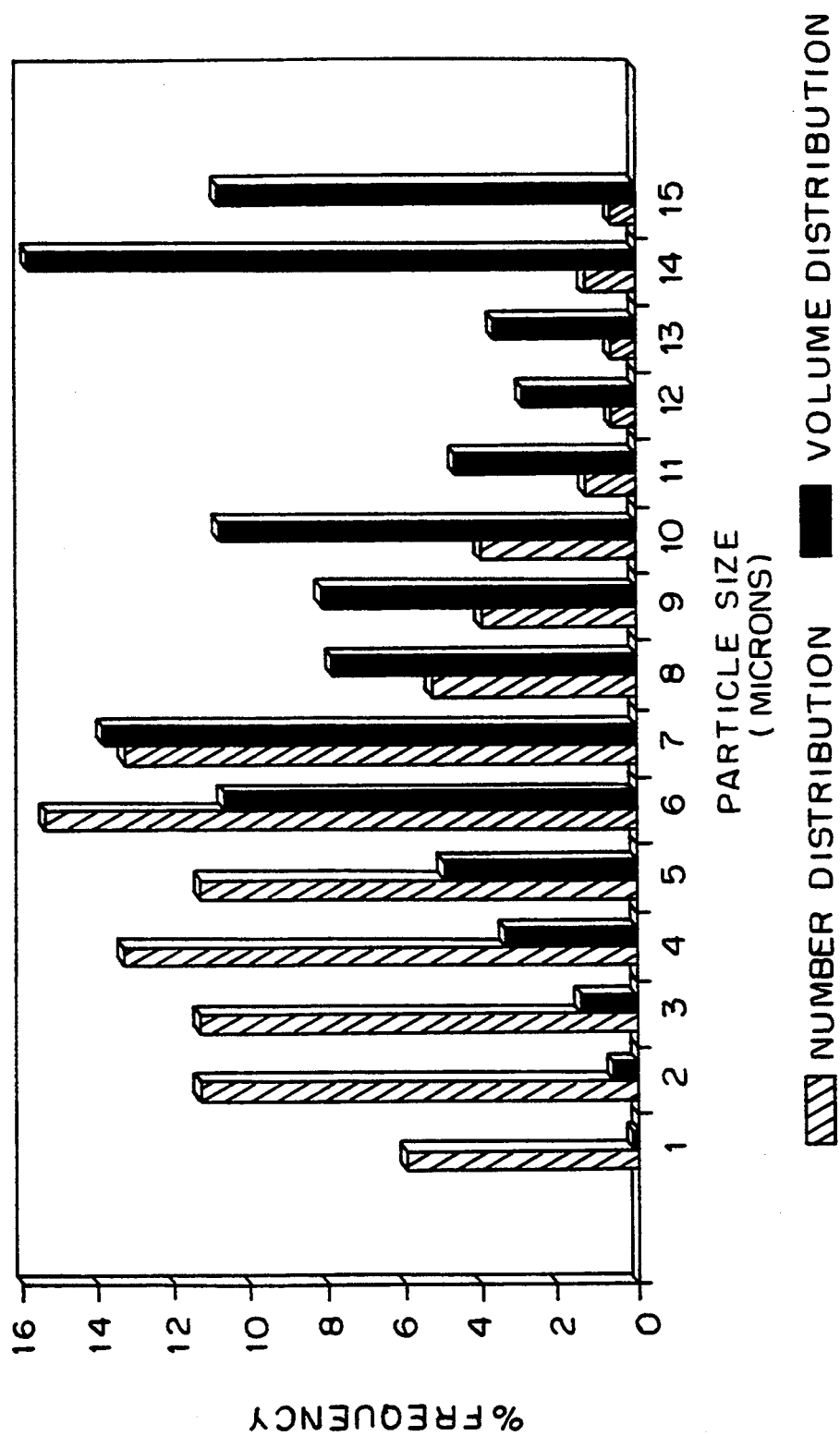

FIG. 29. Particle size distribution of CFA/II microsphere vaccine Lot L74F2 values are percent frequency of number or volume verses distribution. Particle size (diameter) in microns. 63% by volume are between 5-10 um and 88% by volume are less then 10 um.

Figure 30:
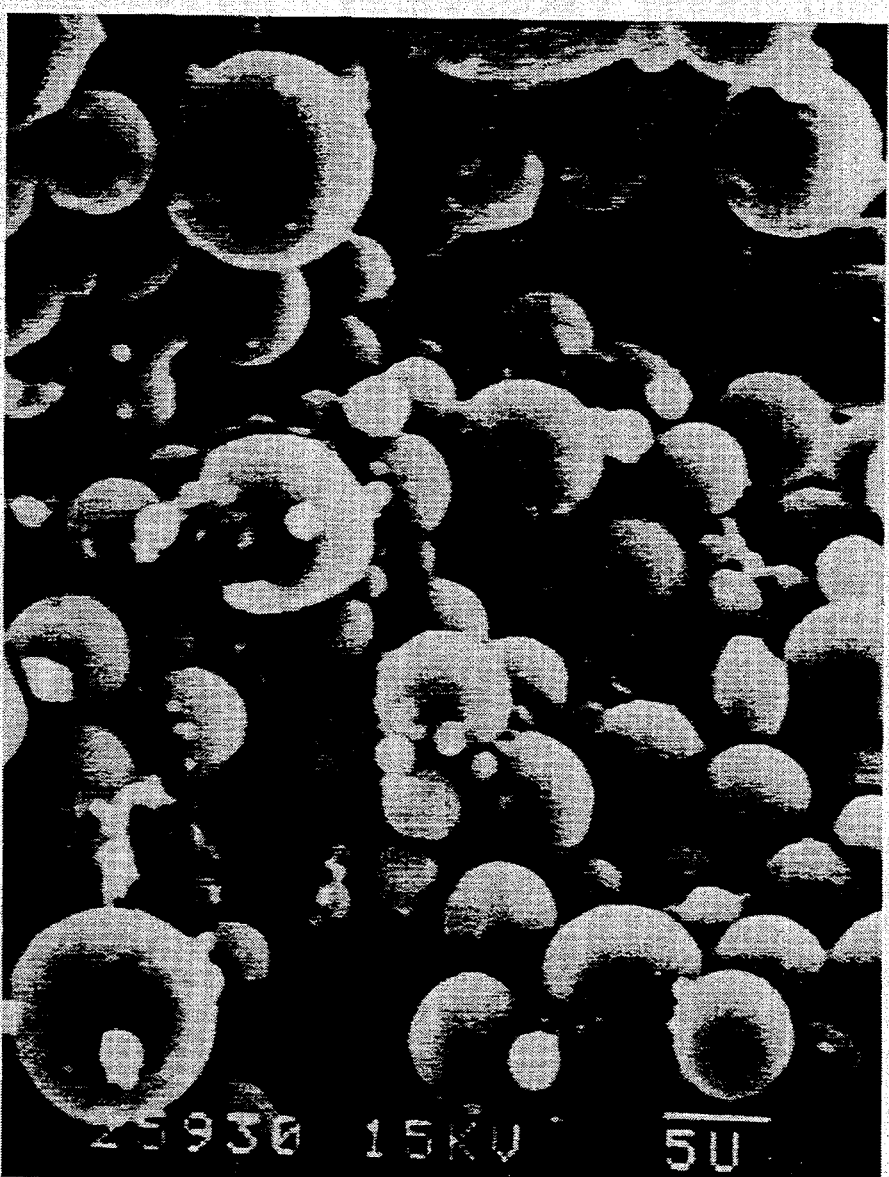

FIG. 30. Scanning electron photomicrograph of CFA/II microsphere vaccine Lot L7472 standard bar represents 5 um distance.

Figure 31:
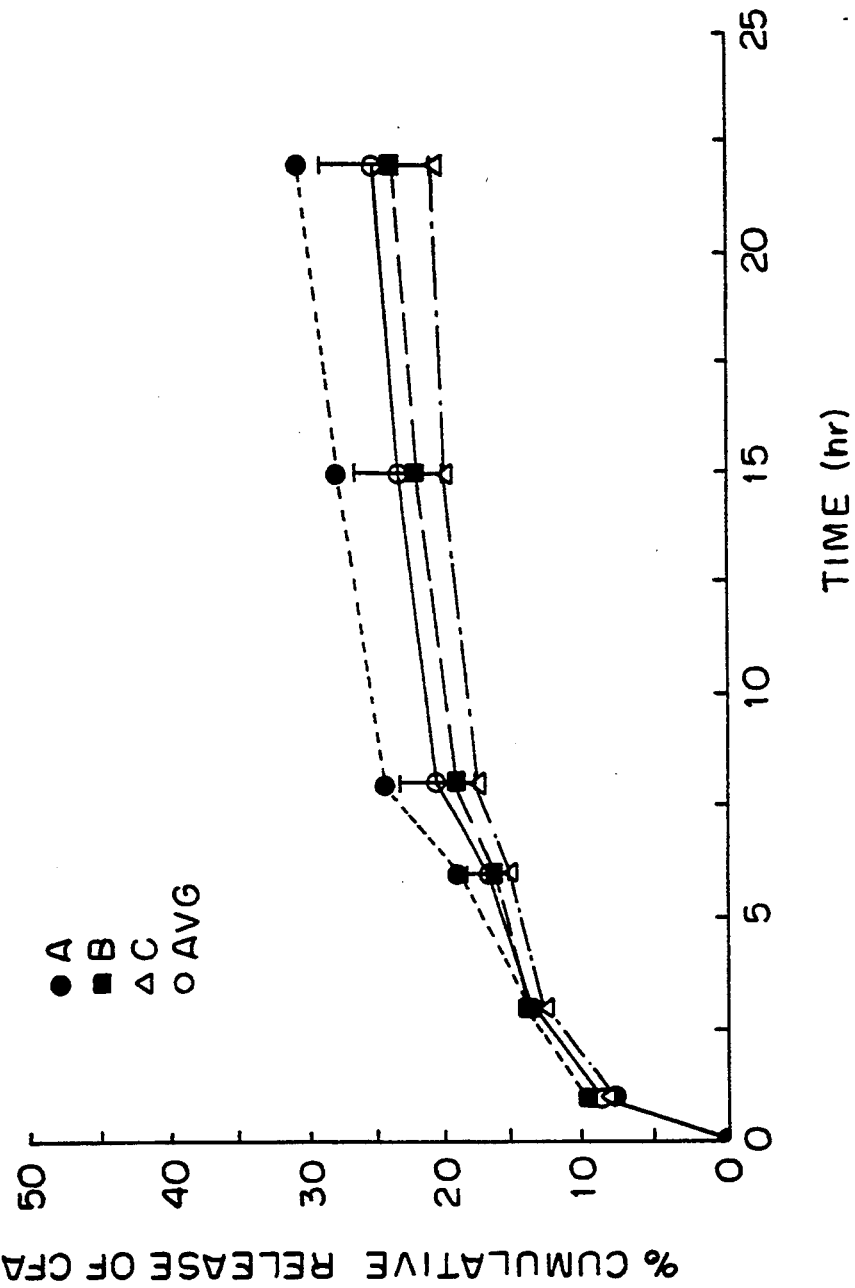

FIG. 31. Twenty-two hour CFA/II release study of CFA/II microsphere vaccine Lot L7472. Percent cumulative release of CFA/II from three sample: A, 33.12 mgm; B, 29.50 mgm c, 24.20 mgm at 1, 3, 6, 8, 12 and 22 hour intervals. Average represents the mean±ISD.

Figure 32:
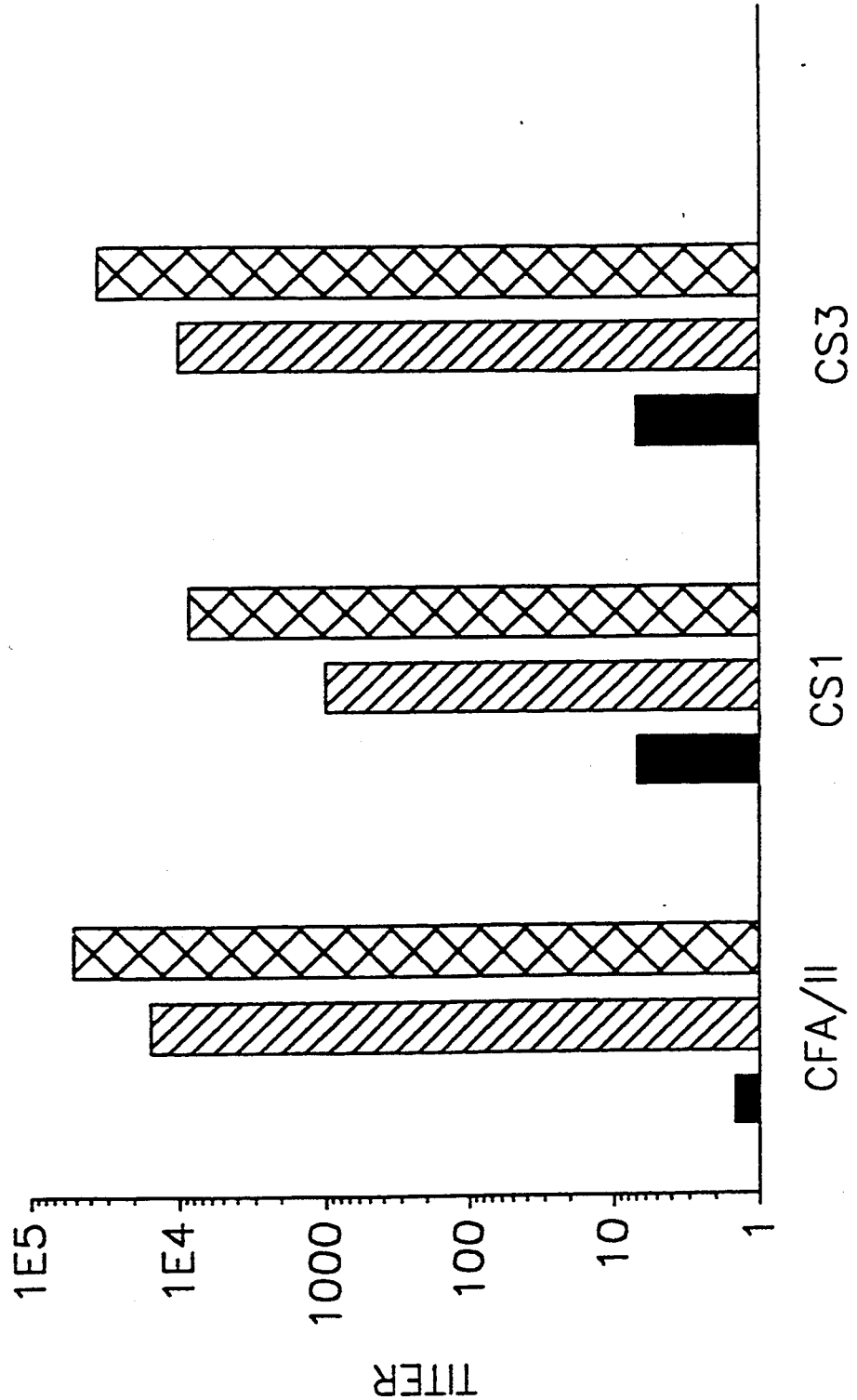

FIG. 32. Serum IgG antibody reponse to CFA/II microsphere vaccine Lot L7472 following 2 25 ug protein IM immunization on day 0 in 2 rabbits. Antibody determines on serial dilution of sera by ELISA and expressed as mean titer versus day 0, 7 and 14.

Figure 33:
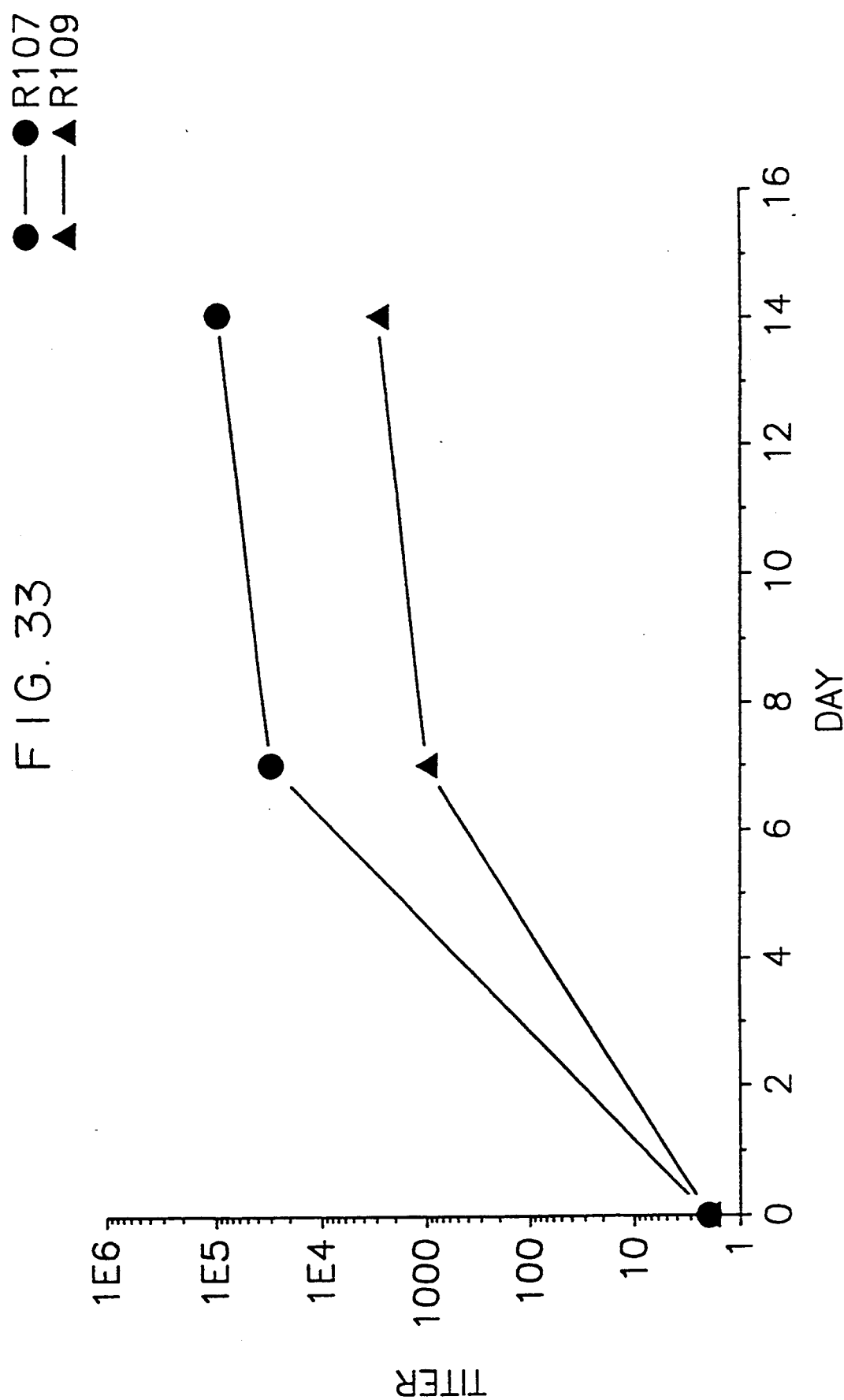
Figure 34B:
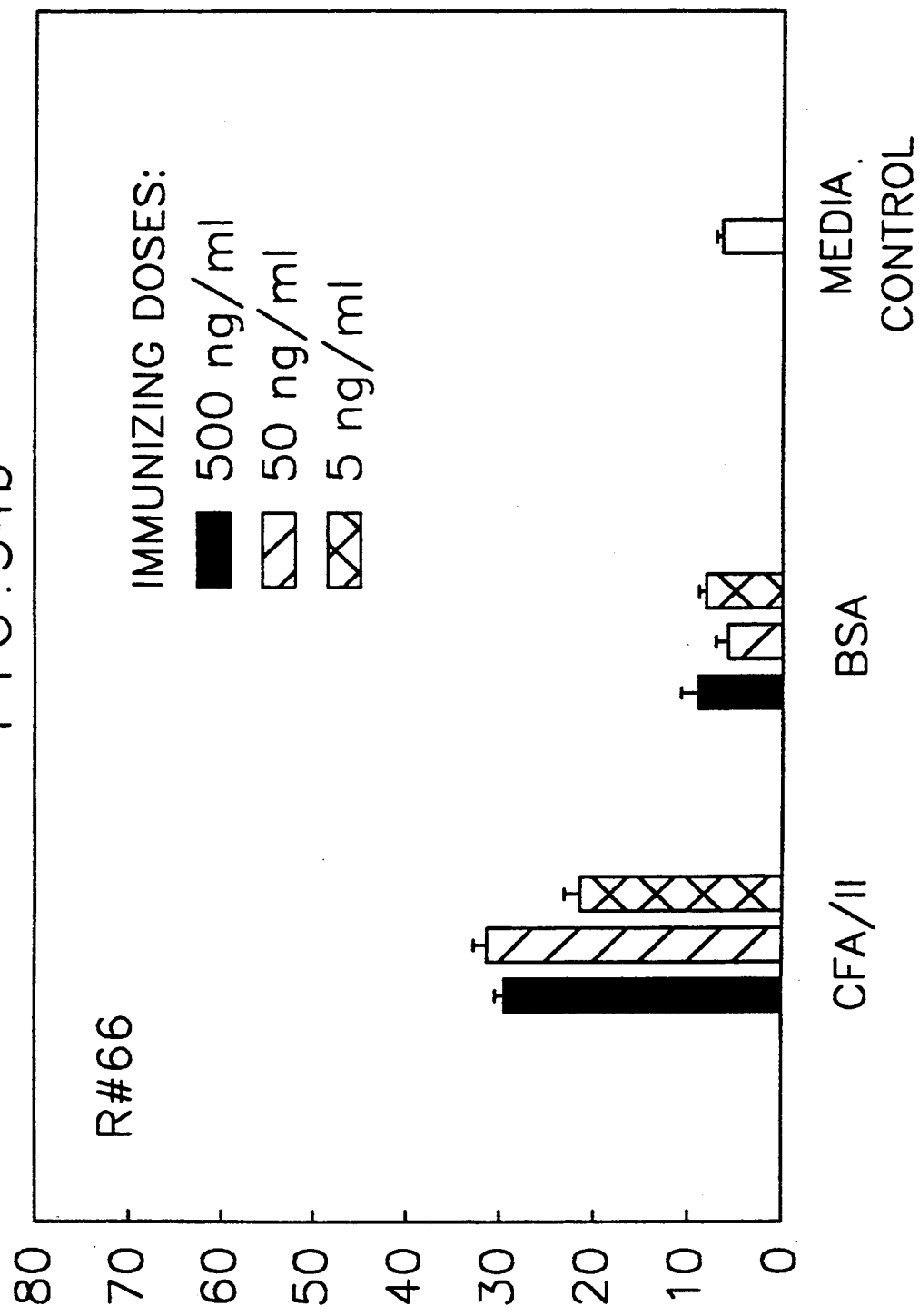
Figure 34C:
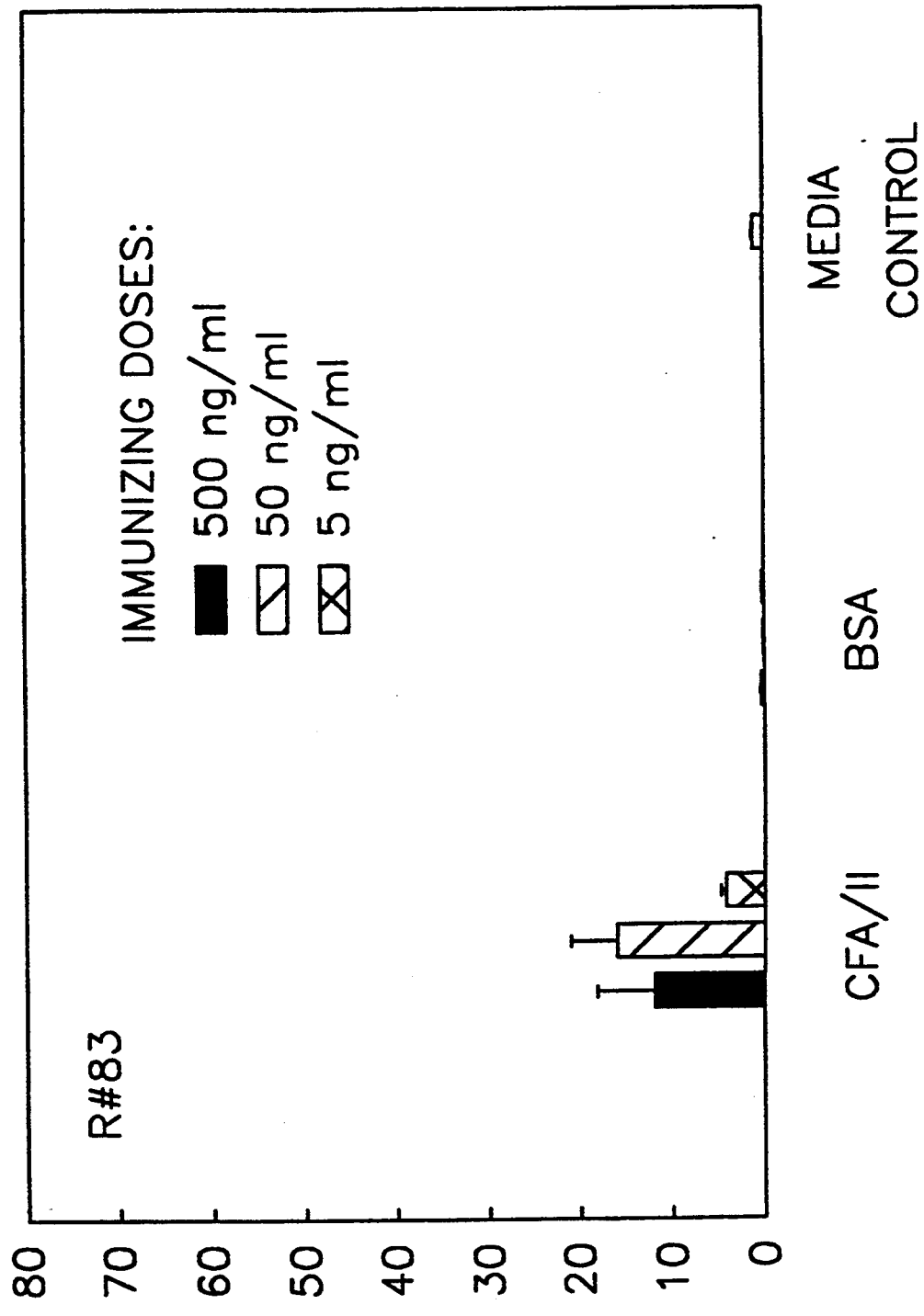
Figure 34D:
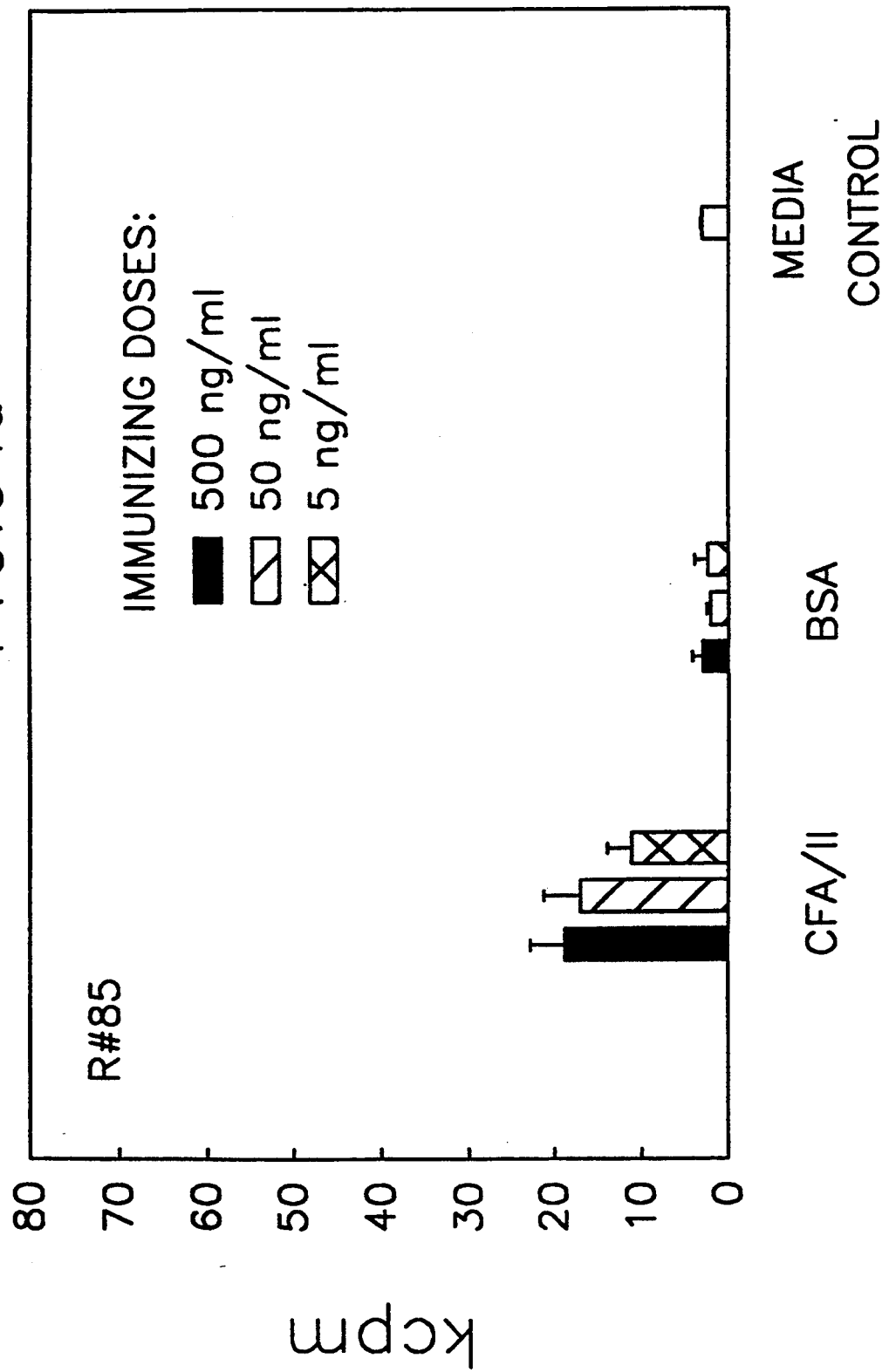
Figure 34E:
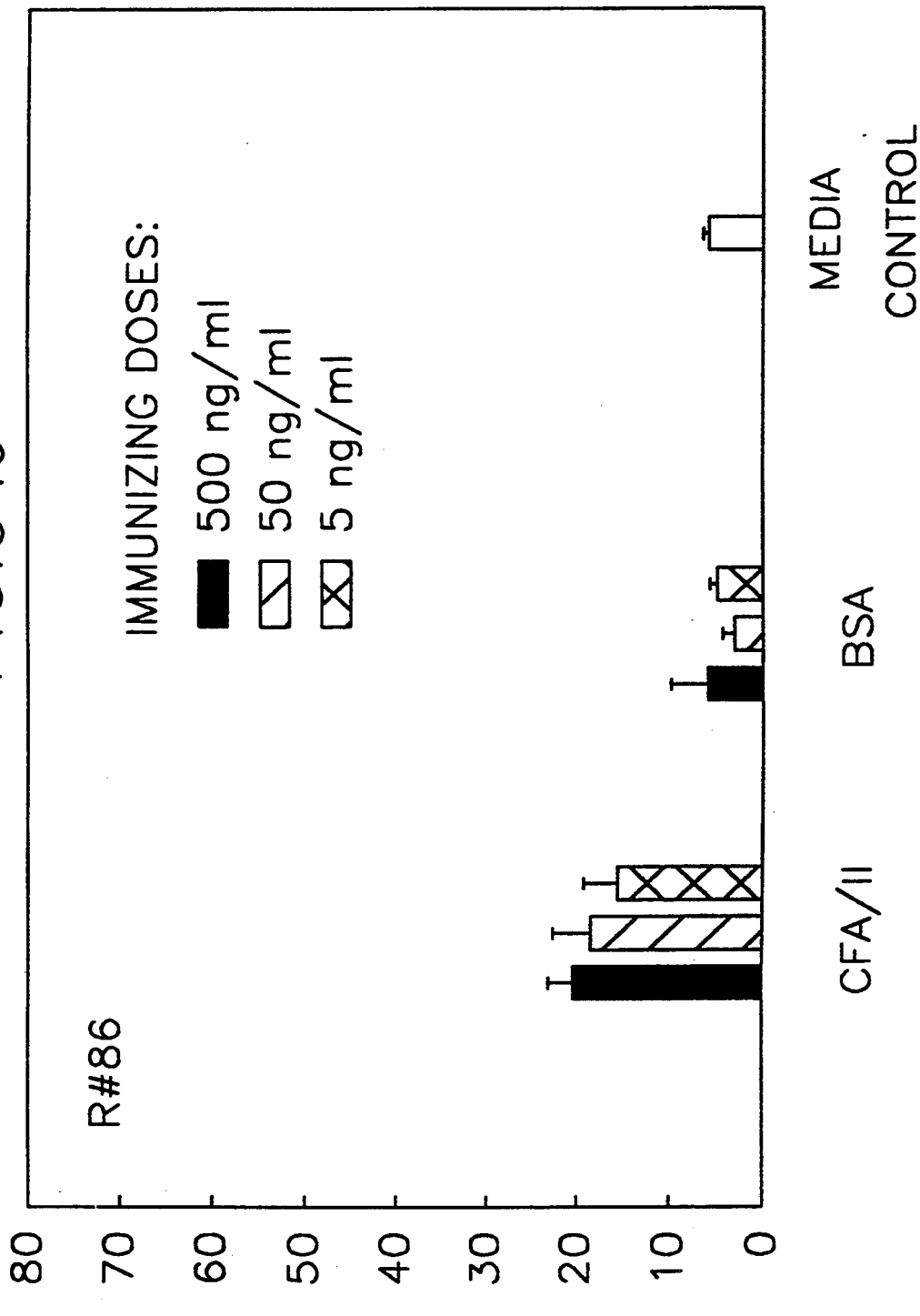
Figure 35A:
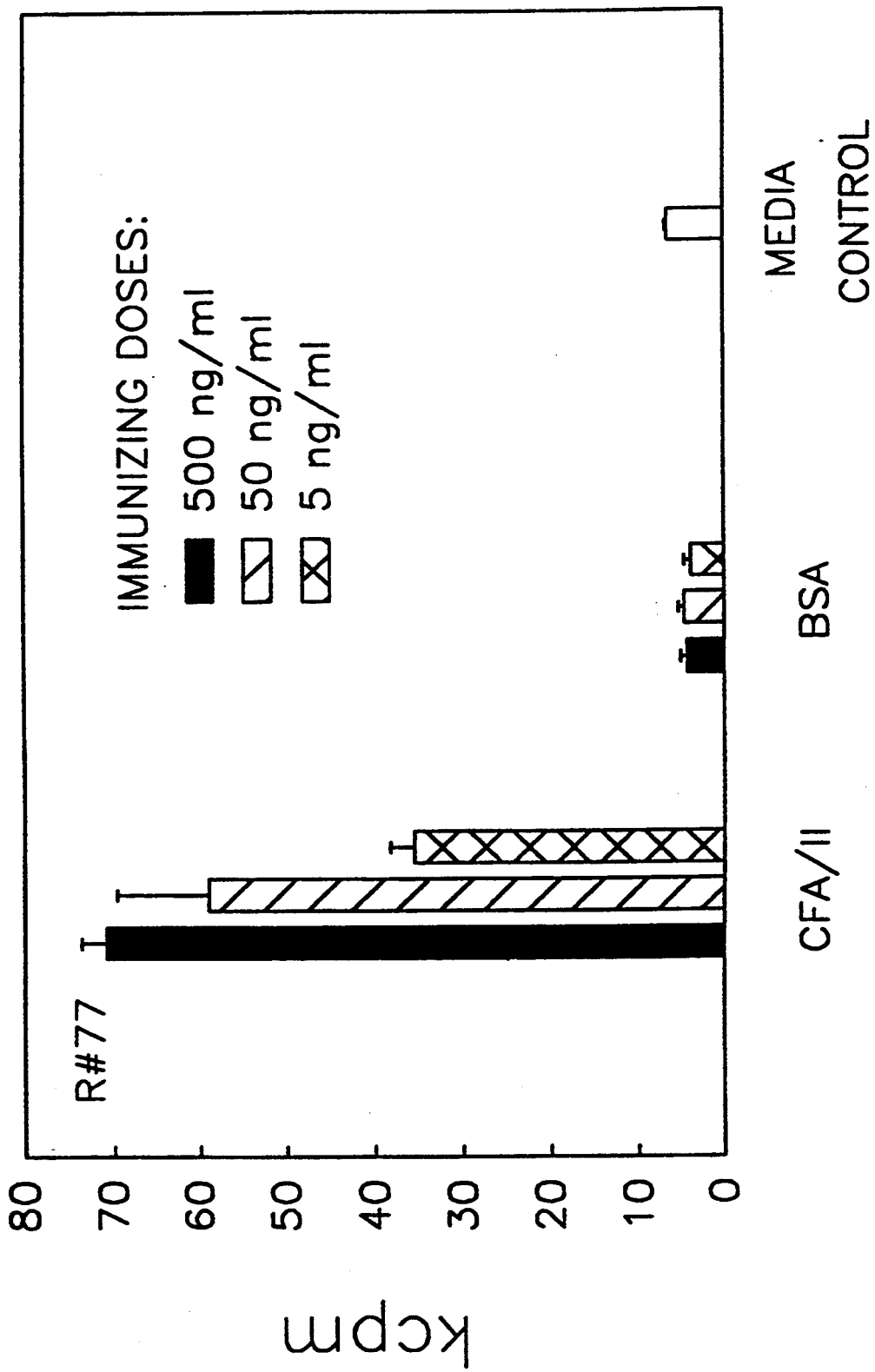
Figure 35B:
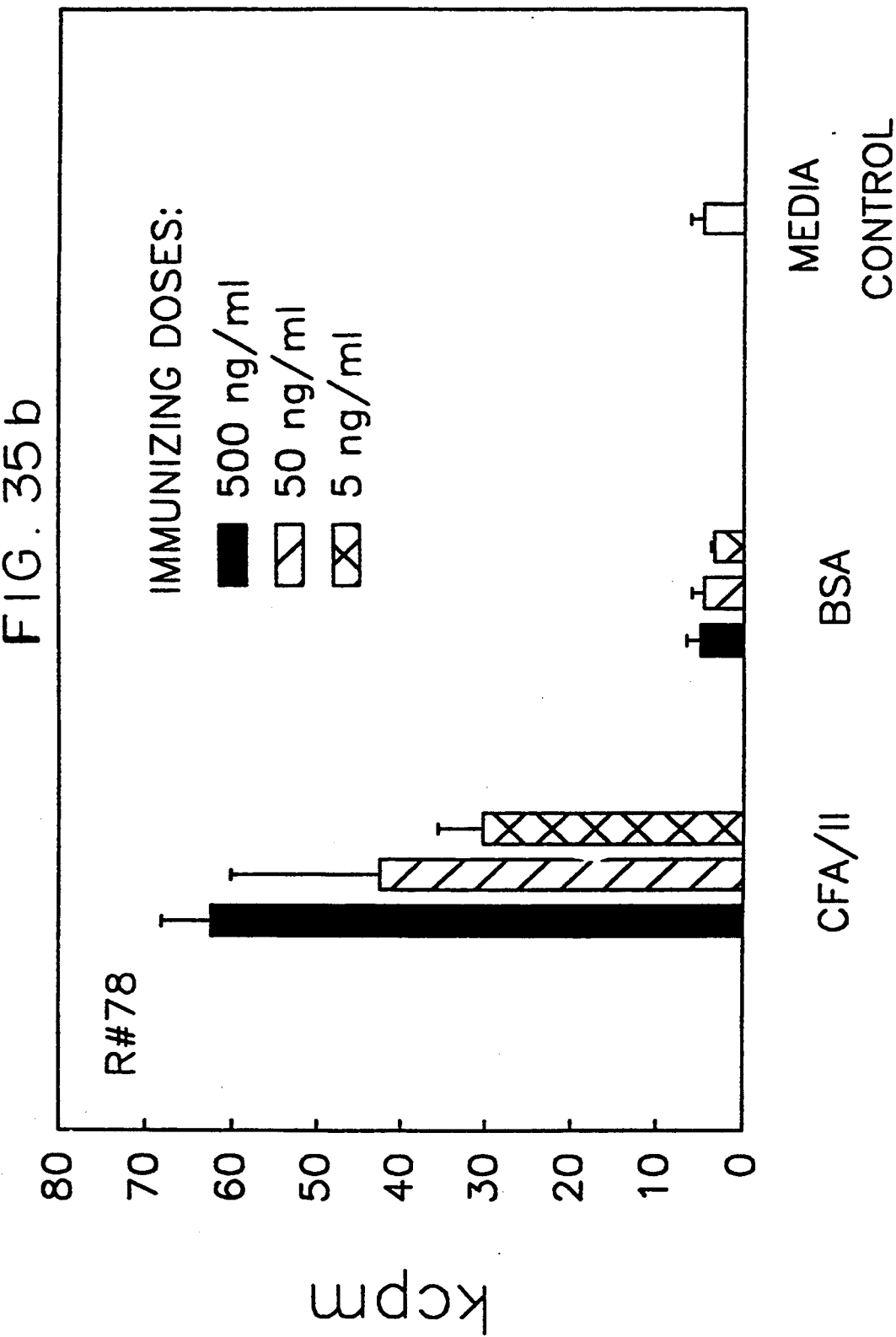
Figure 35C:
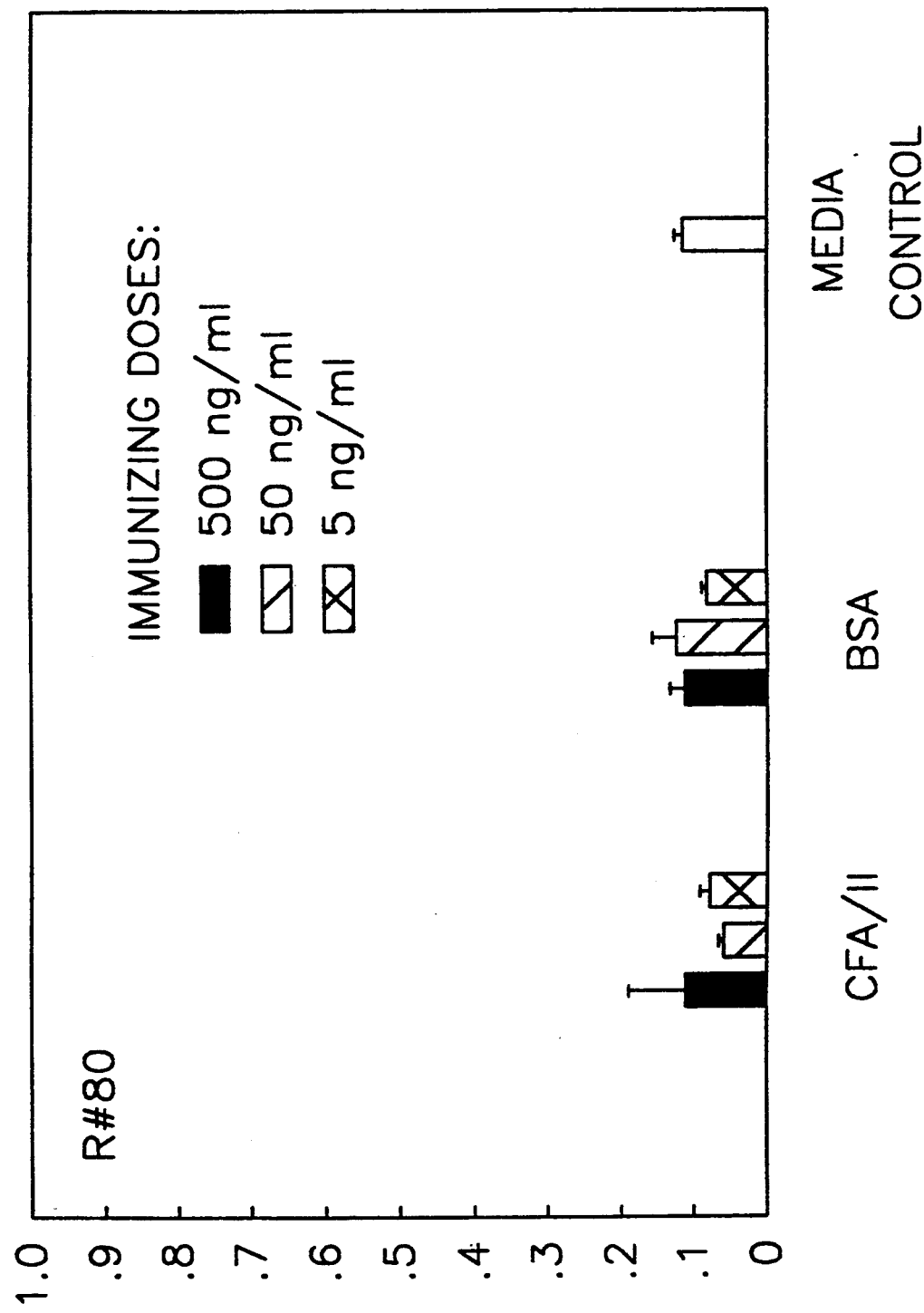
Figure 35D:
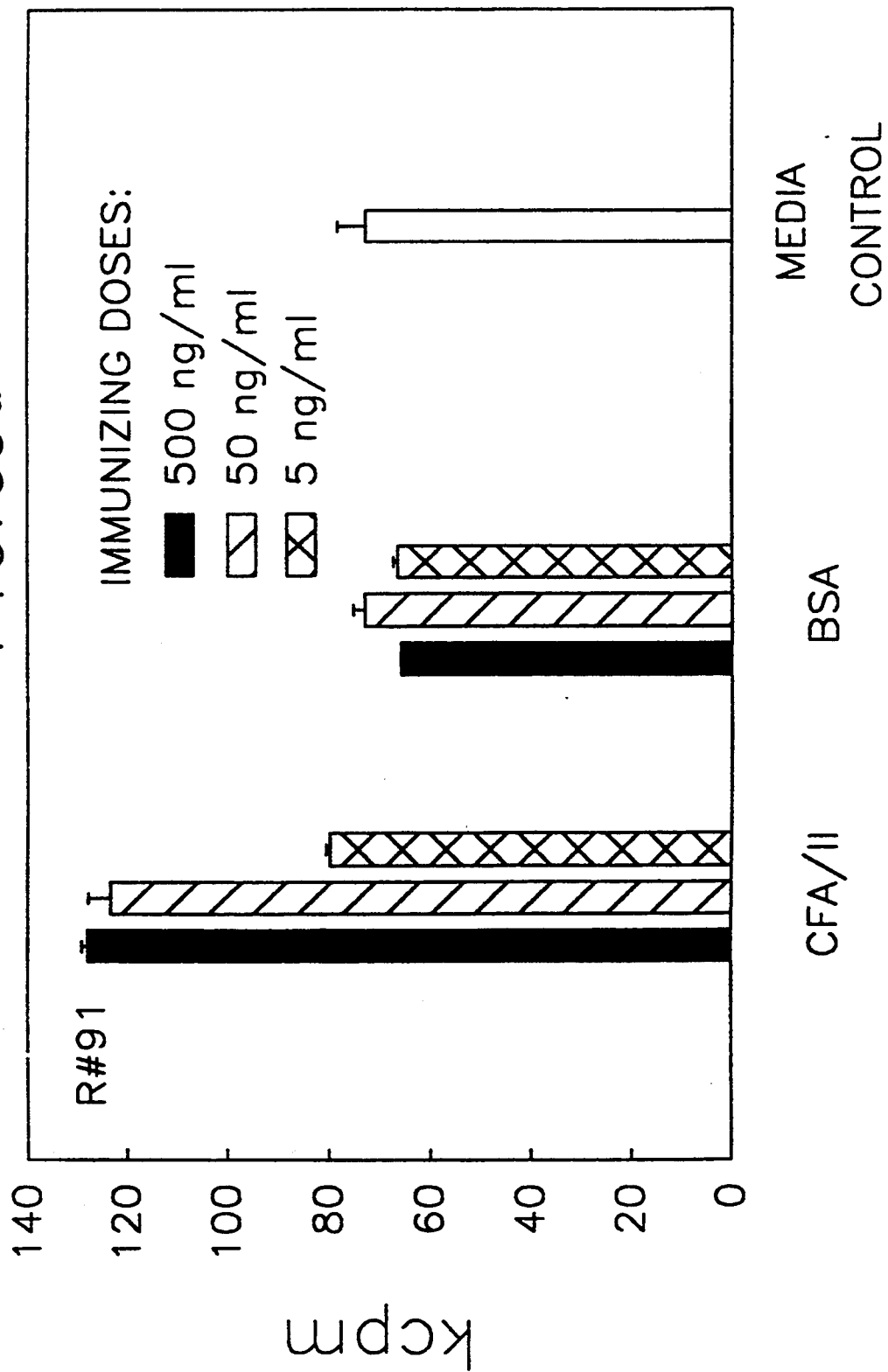

FIG. 33. Serum IgG antibody response to CFA/II microsphere vaccine Lot L7F2 following 2 25 ug protein IM immunizations on day 0 if rabbit 107 & 109. Antibody determined on serial dilution (in duplicate) of sera by ELISA and expressed as mean titer versus day 0, 7 and 14.

FIG. 34. Lymphocyte proliferative responses for Peyer's patch cells of rabbits 65 (FIG. 34(a)), 66 (FIG. 34(b)), 83 (FIG. 34(c)), 86 (FIG. 34(d)), and 87 (FIG. 34(e)) immunized intraduodenally with 50 mgm protein of CFA/II microsphere vaccine 4 and 7 days earlier. The cells are challenged in vitro with CFA/II or BSA at 500, 50 and 5 ug/ml or media in triplicate. The uptake of tritiated thymidine in Kcp is expressed as mean±ISD. Using the paired student t-test, the p values of 500 ug/ml dose of CFA/II compared to media control are: 65,p=0.0002; 66 ,p=0.0002; 83,p=0.0002; and 86, p=0.0002.

FIG. 35. Lymphocyte proliferative responses from Peyer's patch cells of rabbits 77 (FIG. 35(a)), 78 (FIG. 35(b)), 80 (FIG. 35(c)), 88 (FIG. 35(d)), and 91 (FIG. 35(e)) immunized introduodenally with 50 mgm protein of CFA/II microspheres vaccine 14 and 7 days earlier. The cells are challenged in vitro with CFA with CFA/II or BSA at 500, 50 and 5 ug/ml or media in triplicate the uptake of triciplate. The uptake of tritiated thymidine in Kcp is expressed as mean±ISD. Using the paired student t-test, the protein of 500 ug/ml dose of CFA/II compared to media control are: 77, p=0.0001; 78; =0.0015; 80, p=insignificant; 88, p=0.0093; and 91 p=0.0001.

Figure 36C:
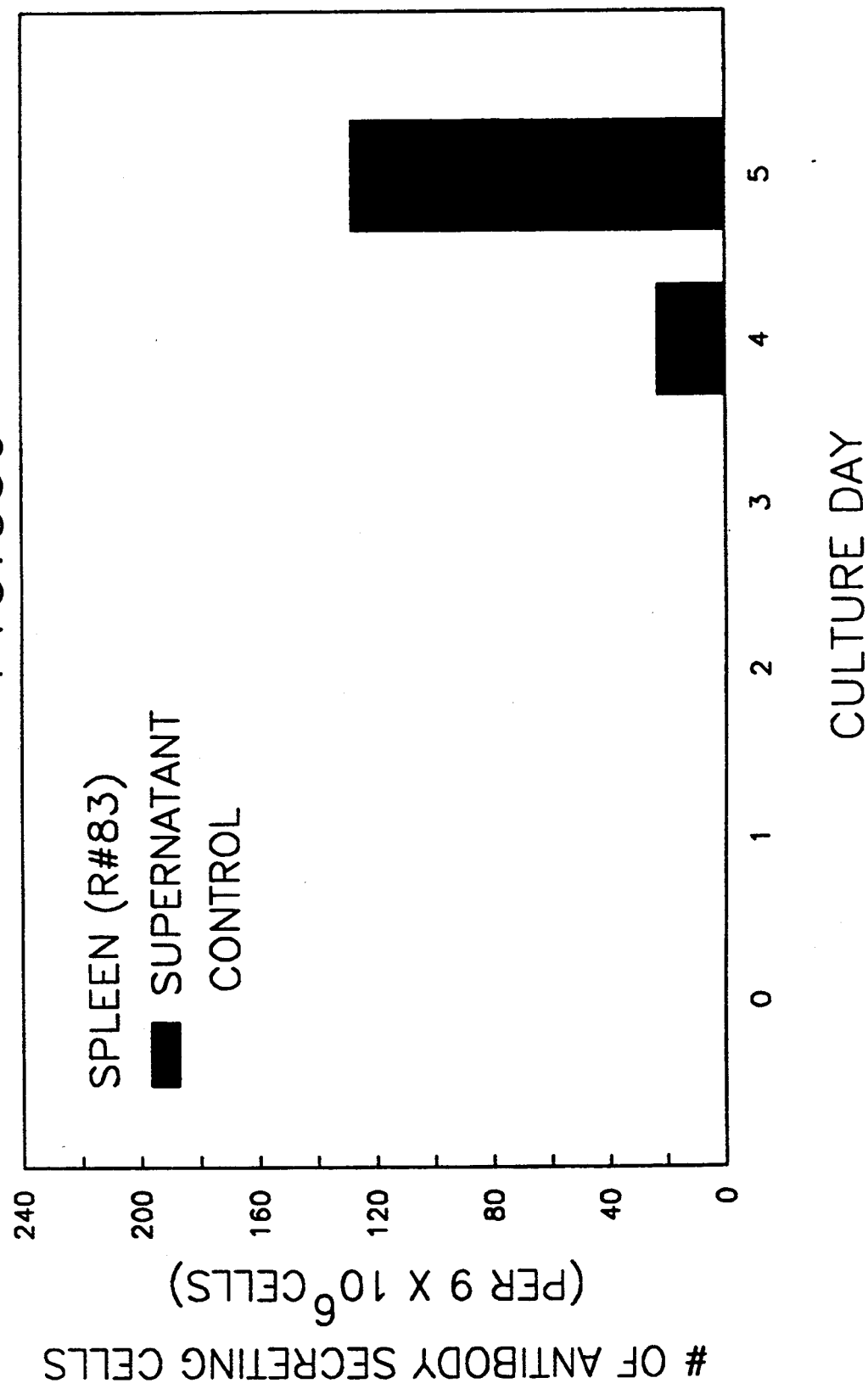

FIG. 36. ELISPOT assay of spleen cells from rabbits 65 (FIG. 36(a)), 66 (FIG. 36(b)), 83 (FIG. 36(c)), 86 (FIG. 36(d)), and 87 (FIG. 36(e)) immunized intraduodenally with 50 mgm protein of CFA/II microsphere vaccine 14 and 7 days earlier. These were cells placed into microculture and tested on day 0, 1, 2, 3, 4 and 5 by ELISPOT for cells secreting antibodies specific for CFA/II antigen. The results are expressed as number per $9 \times 10^6$ spleen cells versus culture day tested.

FIG. 37. ELISPOT assay of spleen cells from normal control rabbits, 67, 69, 72 and 89. The cells were placed into microculture and tested on days 0, 1, 2, 3, 4 and 5 by ELISPOT for cells secreting antibodies specific for CFA/II antigen. The results are expressed as number per $9 \times 10^6$ spleen cells versus culture day tested.

FIG. 38. Curve for determining vaccination dosages for regimen b.

Figure 39:
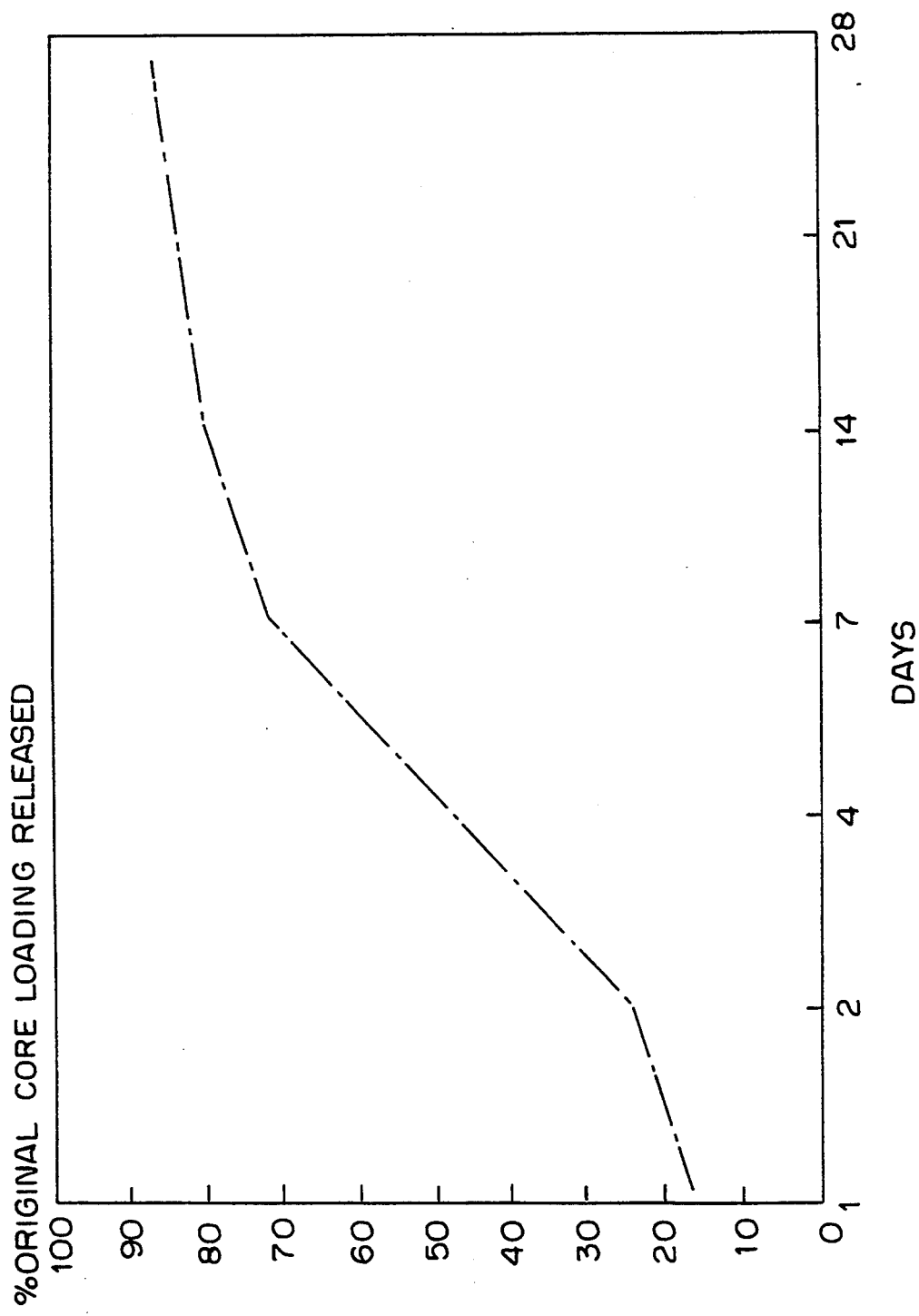

FIG. 39. Hepatitis B surface antigen release from 50:50 poly (DL-lactide-co-glycolide).

FIGS. 11 and 12 serve to illustrate that inclusion of *Escherichia coli* pilus antigen in microspheres enhances cellular immunogenicity.

A primary mucosal immune response, characterized by antipilus IgA, follows infection of rabbits with *E. coli* RDEC-1. However, induction of an optimal primary mucosal response by enteral vaccination with pilus antigen depends on immunogenicity of pilus protein, as well as such factors as its ability to survive gastrointestinal tract (GI) transit and to target immunoresponsive tissue. We tested the effect of incorporating AF/R1 pilus antigen into resorbable microspheres upon its ability to induce primary mucosal and systemic antibody responses after direct inoculation into the GI tract.

METHODS

Rabbits were inoculated with 50 micrograms of AF/R1 pilus antigen alone or incorporated into uniformaly sized (5–10 microns) resorbably microspheres (MIC) of poly(DL-lactide-coglycolide). Inoculation was by intra-duodenal (ID) intubation via endoscopy or directly into the ileum near a Peyer's patch via the RITARD procedure (with the cecum ligated to enhance recovery of gut secretions and a reversible ileal tie to slow antigen clearance). ID rabbits were sacrificed at 2 weeks for collection of gut washes and serum. RITARD rabbits were bled and purged weekly for 3 weeks with Co-lyte to obtain gut secretions. Anti-pilus IgA and IgG were measured by ELISA.

TABLE 1

| RESULTS: *pos/test | RITARD-PILI | RITARD-MIC | ID-PILI | ID-MIC |
|---|---|---|---|---|
| Anti-pilus IgA (fluid) | *7/8 | 4/8 | 1/2 | 0/3 |
| Anti-pilus IgG (serum) | 0/8 | 3/8 | 0/2 | 1/3 |

Native pilus antigen led to a mucosal IgA resposne in 7/8 RITARD rabbits. MIC caused a similar response in only 4/8, but the groups were not statistically different. MIC (but not pili) induced some systemic IgG responses (highest in animals without mucosal responses). Results in rabbits inoculated ID were similar for pili, but no mucosal response to ID-MIC was noted.

SUMMARY

Inoculation with pilus antigen produces a primary mucosal IgA response. Microencapsulation does not enhance this response, although the antigen remains immunogenic as shown by measurable mucosal and some strong serum responses. It must be determined whether priming with antigen in microspheres can enhance secondary responses.

B CELL EPITOPE DATA

Materials and Methods

CFA/I PURIFICATION—INTACT CFA/I pili were purified from H10407 (078:H-) as described by Hall et al, (1989) [20]. Briefly, bacteria grown on colonization factor antigen agar were subjected to shearing, with the shearate subjected to differential centrifugation and isopycnic banding on cesium chloride in the presence of N-lauryl sarkosine. CFA/I were dissociated to free subunits in 6M guanididinium HCl, 0.2M ammonium bicarbonate (2 hr, 25°), passed through an ultrafiltration membrane (Amicon XM 50 stirred cell, Danvers, Mass.), with concentration and buffer exchange to PBS on a YM 10 stirred cell (Amicon). Examination of dissociated pili by electron microscopy demonstrated a lack of pilus structure.

Protein Sequencing—The primary structure of CFA/I has been determined by protein sequencing techniques (Klemm, 1982) and through molecular cloning methods (Karjalainen, et al 1989) [21]. In these two studies there was agreement in all but two of the 147 amino acid residues (at positions 53 and 74). To resolve the apparent discrepancies, CFA/I was enzymatically digested in order to obtain internal amino acid sequence. Trypsin or S. aureus V8 protease (sequencing grade, Boehringer Mannheim) was incubated with CFA/I at a 1:50 w:w ratio (Tris 50 mM, 0.1% SDS, pH 8.5 for 16 h at 37° (trypsin) or 24° C. (V8)). Digested material was loaded onto precast 16% tricine SDS-PAGE gels (Schagger and von Jagow, 1987) (Novex, Encinitis, Calif.) and run following manufacturers instructions. Separated samples were electrophoretically transferred to PVDF membranes (Westrans, Schleicher and Schuell, Keene, N.H.) following Matsiduria (1987) using the Novex miniblot apparatus. Blotted proteins were stained with Rapid Coomassie stain (Diversified Biotech, Newton Centre, Mass.). To obtain the desired fragment containing the residue of interest within a region accessible by automated gas phase sequencing techniques, molecular weights were estimated from standards of molecular weights 20,400 to 2,512 (trypsin inhibitior, myoglobin, and myoglobin cyanogen bromide fragments; Diversified Biotech) using the corrected molecular weights for the myoglobin fragments as given in Kratzin et al., (1989) [22]. The estimated molecular weights for the unknown CFA/I fragments were compared to calculated molecular weights of fragments as predicted for CFA/I from the sequence of CFA/I as analysed by the PEPTIDESORT program of a package developed by the University of Wisconsin Genetics Computer Group. Selected fragments were cut from the PVDF emebrane and subjected to gas phase sequencing (Applied Biosystem 470, Foster City, Calif.).

Monkey Immunization—Three rhesus monkeys (Macaca mulatta) were injected intramuscularly with 250 ug of dissociated CFA/I in complete Freund's adjuvent and subsequently with two injections of 250 ug of antgen in incomplete Freund's adjuvent at weekly intervals. Blood was drawn three weeks after primary immunization.

Peptide Synthesis—Continuous overlapping octapeptides spanning the entire sequence CFA/I were synthesized onto polyethylene pins by the method of Geysen et al. [16], also known as the PEPSCAN procedure. Derivitized pins and software were purchased from Cambridge Research Biochemicals (Valley Stream, N.Y.). Fmoc-amino acid pentafluorophenyl esters were purchased from Peninsular Laboratories (Belmont, Calif.), 1-hydroxybenzotriazole monohydrate (HYBT) was purchased from Aldrich, and reagent grade solvents from Fisher. To span the entire sequence of CFA/I with a single amino acid overlap of from one peptide to the next, 140 total pins were necessary, with a second complete set of 140 pins synthesized simultaneously.

ELISA procedure—Sera raised in monkeys to purified dissociated pili were incubated with the pins in the capture ELISA assay of Geysen et al., [16] with the preimmune sera of the same animal tested at the same dilution simultaneously with the duplicate set of pins. Dilution of sera used on the pins was chosen by initial titration of sera by standard ELISA assay and immunodot blot assay against the same antigen.

RESULTS

Figures 16A, 16B:

It was essential to utilize the correct sequence of CFA/I in the synthesis of the pins for both T- and B-cell experiments to carry out the studies as planned. At issue were the amino acids at position 53 and 74; incorrect residues at those positions would effect 36 of 138 pins (26%) for T-cell epitope analysis and 30 of 140 pins (21%) for B-cell analysis. To resolve the discrepancy in the literature, purified CFA/I was proteolytically digested separately with trypsin and with S. aureus V8 protease (V8). These enzymes were chosen in order to give fragments with the residues of interest (53 and 74) relatively near to the N-terminus for automated Edman degradation (preferably 1–15 residues). These digests were separated on tricine SDS-PAGE gels (FIG. 16A) and molecular masses of fragments estimated. A fragment of 3459 calculated molecular mass is expected from the trypsin digest (corresponding to amino acids 62–94) and a fragment of 5889 calculated molecular mass is expected from the V8 digest (residues 42–95).

These fragments were located within each digest (arrows in FIG. 16), and a companion gel with four lanes of each digest was run, electrophoreticaly transferred to PVDF, the bands excised and sequenced. N-terminal sequences of each fragment are given in FIG. 16B. The N-terminal eighteen residues from the trypsin fragment were determined that corresponded to positions 62–79 in CFA/I. Position 74, a serine residue was consistent with that determined by Karjalainen et al., (Karjalainen et al., 1989). Nineteen residues of the V8 fragment were determined, corresponding to residues 41–60 of the parent protein. The twelfth residue of the fragment contained an aspartic acid, also consistent with Karjalainen et al., (1989). All other residues sequenced were consistent with those published previously (including residues 1–29, not shown). For the following peptide synthesis were therefore utilized the complete amino acid sequence of CFA/I consistent with Karjalainen et al., (1989).

Figure 17A:
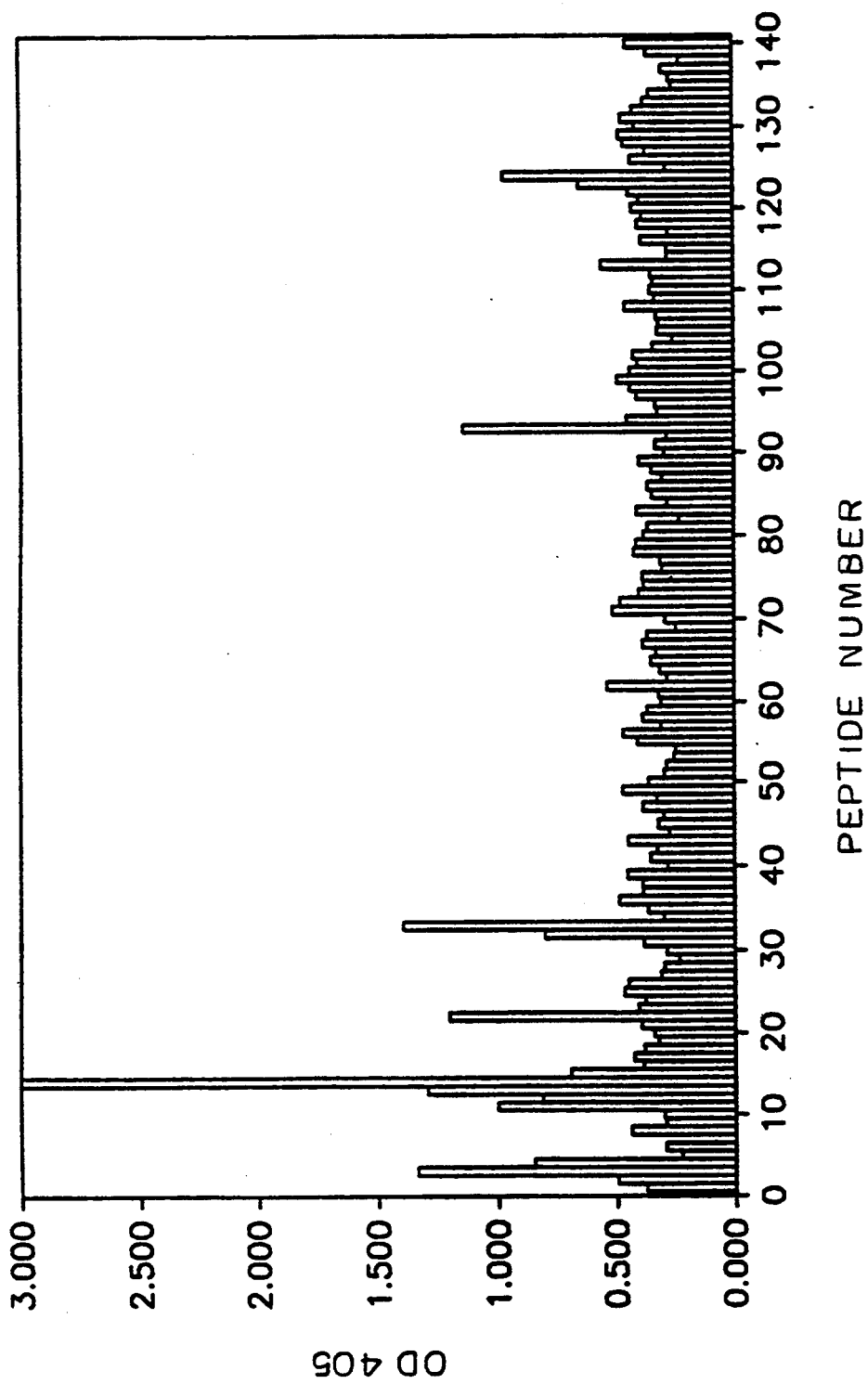
Figure 17B:
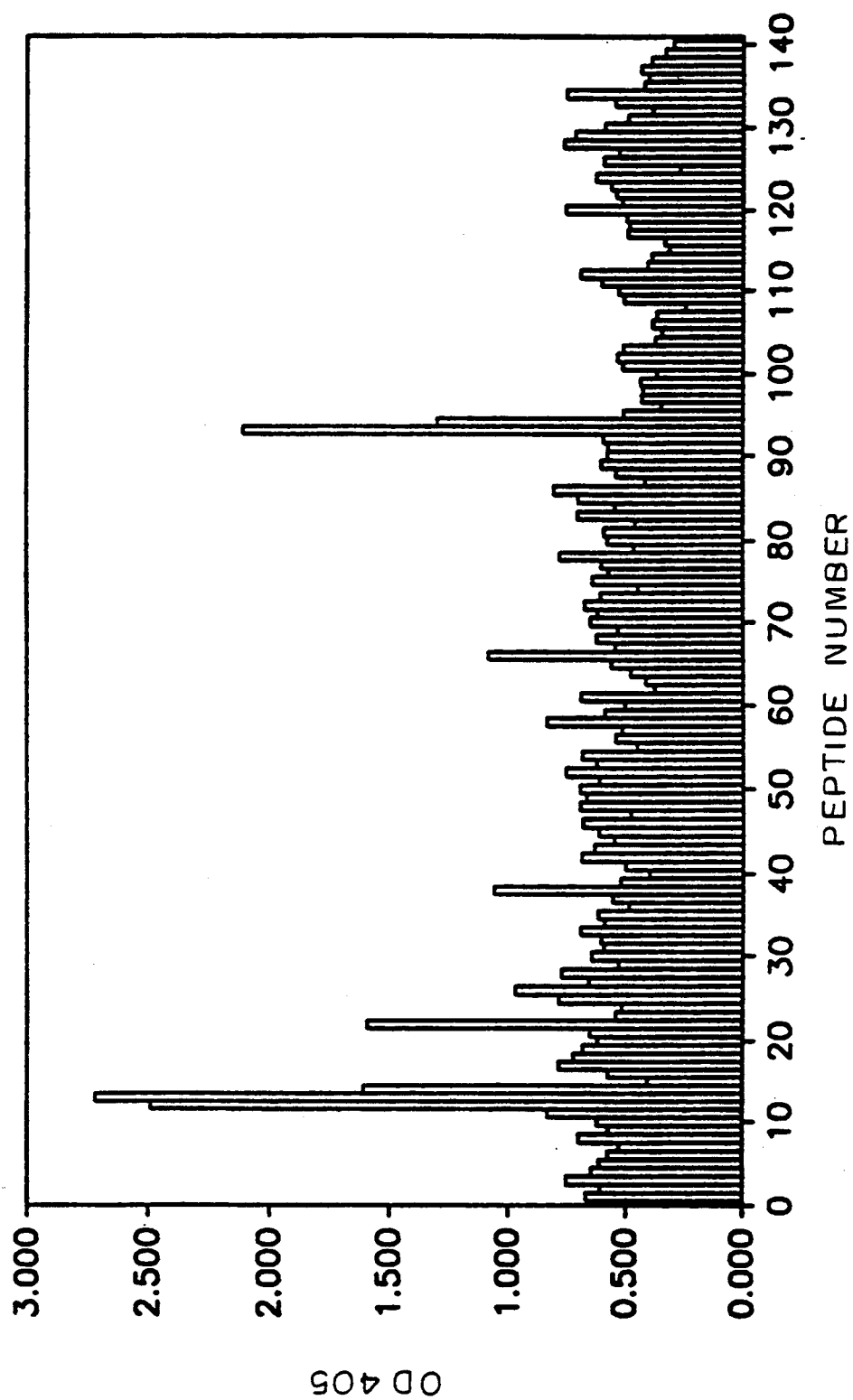
Figure 17C:
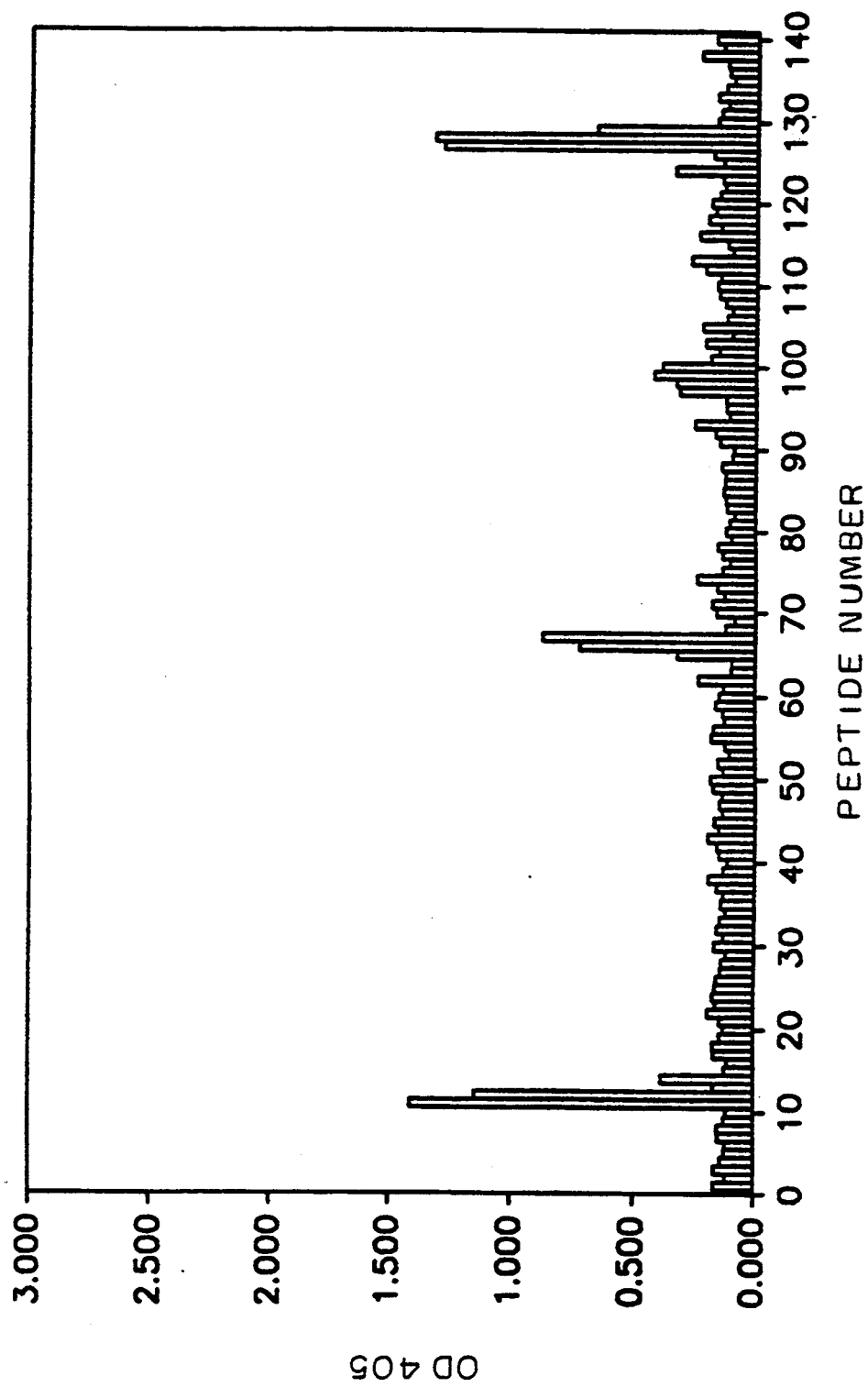
Figure 18:
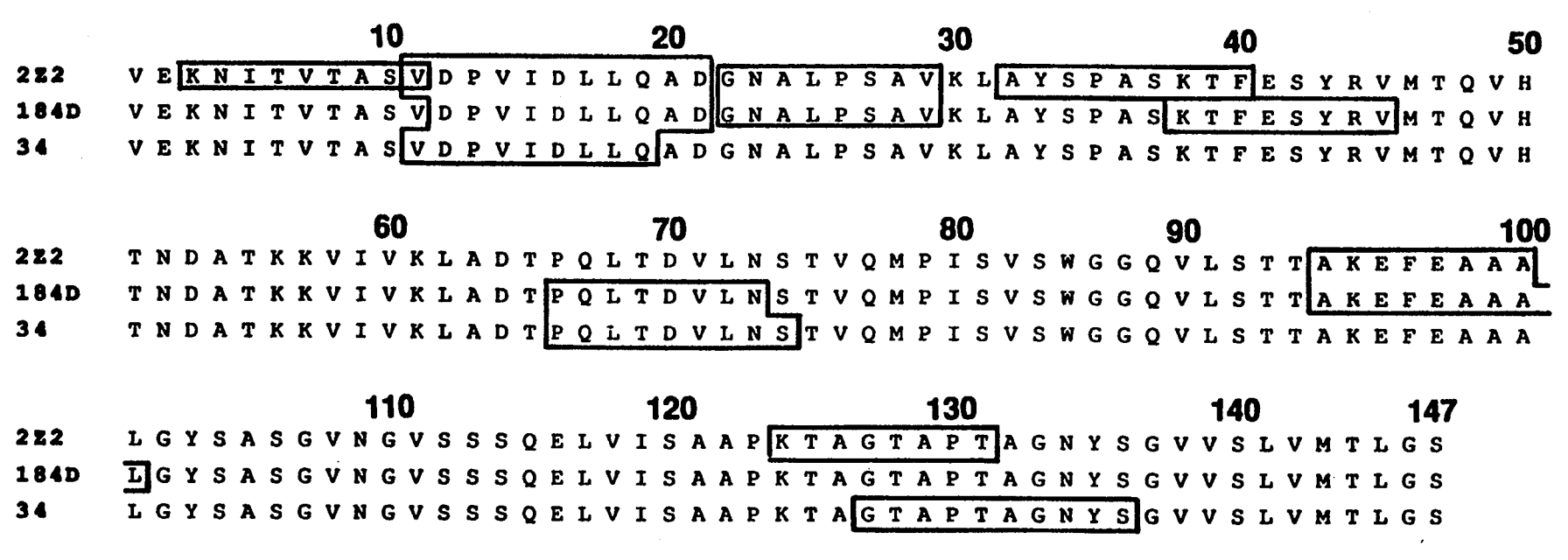

Sera from monkeys immunized with CFA/I subunits were tested in a modified ELISA assay, with the preimmunization sera tested simultaneously with duplicate pins. Assays results are displayed in FIG. 17. Monkey 2Z2 (FIG. 2A) responded strongly to six regions of the CFA/I sequence. Peptide 14 (the octapeptide 14–21) gave the strongest response with four pins adjacent to it (11, 12, 13, and 15) also appearing to bind significant antibody. The other 2Z2 epitopes are centered at peptides 3, 22, 33, 93, and 124. Monkey 184D (FIG. 17B) also responded strongly to peptide 14, although the maximum response was to peptide 13, with strong involvement of peptide 12 in the epitope. Additional epitopes recognized by 184d were centered at peptides 22, 33, 66, and 93. The third monkey serum tested, 34, responded to this region of the CFA/I primary structure, both at peptides 1, 12 and weakly at 14. Two other epitopes were identified by 34, centered at peptides 67 and 128. FIG. 18 illustrates the amino acids corresponding to the epitopes of CFA/I as defined by the response of these three monkeys aligned with the entire primary structure. The entire antigenic determinants are mapped and areas of overlap with other epitopes (consensus sites) are displayed. These epitopes are summarized in Table 1.

T Cell Epitope Data

Materials and Methods

Animals. Three healthy adult *Macaca mulatta* (Rehesus) monkeys (approximately 7 kg each) were used in this study. Their medical records were examined to assure that they had not been in a previous protocol which would preclude their use in this study. Each monkey was sedated with ketamine HCL1 at standard dosage and blood was drawn to obtain preimmune serium.

Antigen. CFA/I pili were purified from *E. coli* strain H107407 (serotype 078:H11) by ammonium sulfate precipitation using the method of Isaacson [17]. The final preparation migrated as a single band on SD-polyacrylamide gel electrophoresis and was shown to be greater than 95% pure by scanning with laser desitometry when stained with coomassie blue. The pili were then dissociated into CFA/I pilin subunits.

Immunization. Each monkey was given 25 mg of purified CFA/I pilin subunits, which had been emulsified in Complete Freund's Adjuvant, by single i.m. injection (0.5 ml). For each animal, the initial dose of antigen was followed by two similar injections in Incomplete Freund's Adjuvant at seven day intervals.

Peptide Antigens. The peptides were synthesized based on the published sequence of CFA/I [18] using the Geysen pin method (Pepscan procedure) [16] with equipment and software purchased from Cambridge Research Biochemicals, Inc. (Wilmington, Del.). Fmoc-amino acid pentafluorophenyl esters were purchased from Peninsula Laboratories (Belmont, Calif.) and used without further treatment or analysis. The activating agent 1-hydroxybenzotriazole monohydrate (HOBT) was purchased from Aldrich Chemical Company (Milwaukee, Wis.). Solvents were reagent-grade from Fisher Scientific (Springfield, N.J.).

Two schemes were used to synthesize the peptides. Peptides for the B-cell tests were synthesized as octamers and remained linked to the resin. However, the peptides used to search for T-cell epitopes were synthesized as decamers with an additional Asp-Pro spacer between the pins and the peptides of interest. The Asp-Pro linkage is acid labile allowing cleavage of the decamers from the pins for T-cell proliferation assays [15]. The peptides were cleaved in 70% formic acid for 72 hours at 37 degrees C. The acid solution was removed by evaporation (Speed-Vac, Savant Instruments, Framingdale, N.Y.) followed by rehydration with distilled deionized water and lyophilizaiton. The resulting cleaved peptides were used without further treatment or analysis. The yield was approximately 10 ug per pin, approximately 10 per cent on a molar basis of the total amount of proline on each pin as determined by quantitative amino acid analysis.

Residues 12 and 13 on the CFA-1 protein are Asp and Pro, respectively, the same sequence used to cleave the peptides from the pins. Therefore, to prevent truncated peptides from the native sequence during the cleavage process, two substitutions were made for Asp-12. One substitution was a glutamic acid residue for the aspartic acid, a substitution to retain the carboxylic acid functional group. The second substitution was an asparagine residue to conserve the approximate size of the side chain while retaining some hydrophilicity. Each substitution was tested in the T-cell proliferation assay. Both substitutions as well as the native sequence were analyzed by ELISA. For both the T cell and B cell assays, additional sequences not found on the protein were synthesied and used as control peptides.

Lymphocyte proliferation. At day 10–14 following the final inoculation of antigen, the monkeys were again sedated with ketamine HCl, and 50 ml of blood was drawn from the femoral artery for serum preparation. Animals were then euthanized with an overdose of pentothal and spleen was removed. Single cell suspensions were prepared and washed in Dulbecco's modified Eagle medium (Gibco Laboratories, Grand Island, N.Y.) which had been supplemented with penicillin (100 units/ml), streptomycin (100 ug/ml), L-glutamine (2 mM), and HEPES Buffer (10 mM) all obtained from Gibco Laboratories, as well as MEM non-essential amino acid solution (0.1 mM), MEM [50×] amino acids (2%), sodium bicarbonate (0.06%), and $5 \times 10^{-5}$M 2-ME all obtained from Sigma Chemical Company (St. Louis, Mo.) [cDMEM]. Erythrocytes in the spleen cell suspension were lysed using standard procedures in an ammonium chloride lysing buffer. Cell suspensions were adjusted to $10^7$ cells per ml in cDMM, and autologous serum was added to yield a final concentration of 1.0%. Cells (0.05 ml) were plated in 96-well flat bottom culture plates (Costar, Cambridge, Mass.) along with 0.05 ml of various dilutions of antigen in cDMEM without serum (yielding a 0.5% final concentration of autologous serum) and were incubated at 37 degrees C. in 5% $CO_2$. Each peptide was tested at 6.0, 0.6, 0.06 ug/ml. All cultures were pulsed with 1 uci [$^3$H]thymidine (25 Ci/mmol, Amersham, Arlington Hights, Ill.) on day 4 of culture and were harvested for scintillation counting 6 hours later.

ELISA.

Epitope prediction. Software designed to predict B cell epitopes based on hydrophilicity, flexibility, and other criteria was developed by the University of Wisconsin Genetics Computer Group [19]. Software designed to predict T cell epitopes based on the Rothbard method [7] was written by Stephen Van Albert (The Walter Reed Army Institute of Research, Washington, D.C.). Software designed to predict T cell epitopes based on the Berzofsky method was published as the AMPHI program [9]. It predicts amphipathic amino acid segments by evaluating 7 or 11 residues as a block and assigning the score to the middle residue of that block.

Statistics. All lymphocyte proliferations were conducted in replicates of four, and standard deviations of the counts per minute (cpm) are shown. Statistical significance (p value) for the proliferative assay was determined using the Student's t test to compare the cpm of quadruplicate wells cultured with the CFA/I peptides to the cpm of wells cultured with a control peptide.

RESULTS

Prediction of T cell epitopes within the CFA/I molecule. To identify possible T cell epitopes within the CFA/I molecule, amphipathic amino acid segments were predicted by evaluating 7 or 11 residues as a block using the AMPHI program [9]. Possible t cell epitopes were also identified using criteria published by Rothbard and Taylor [7]. The sequence numbers of the first amino acid of the predicted segments are shown in Table 1.

Figure 3A:
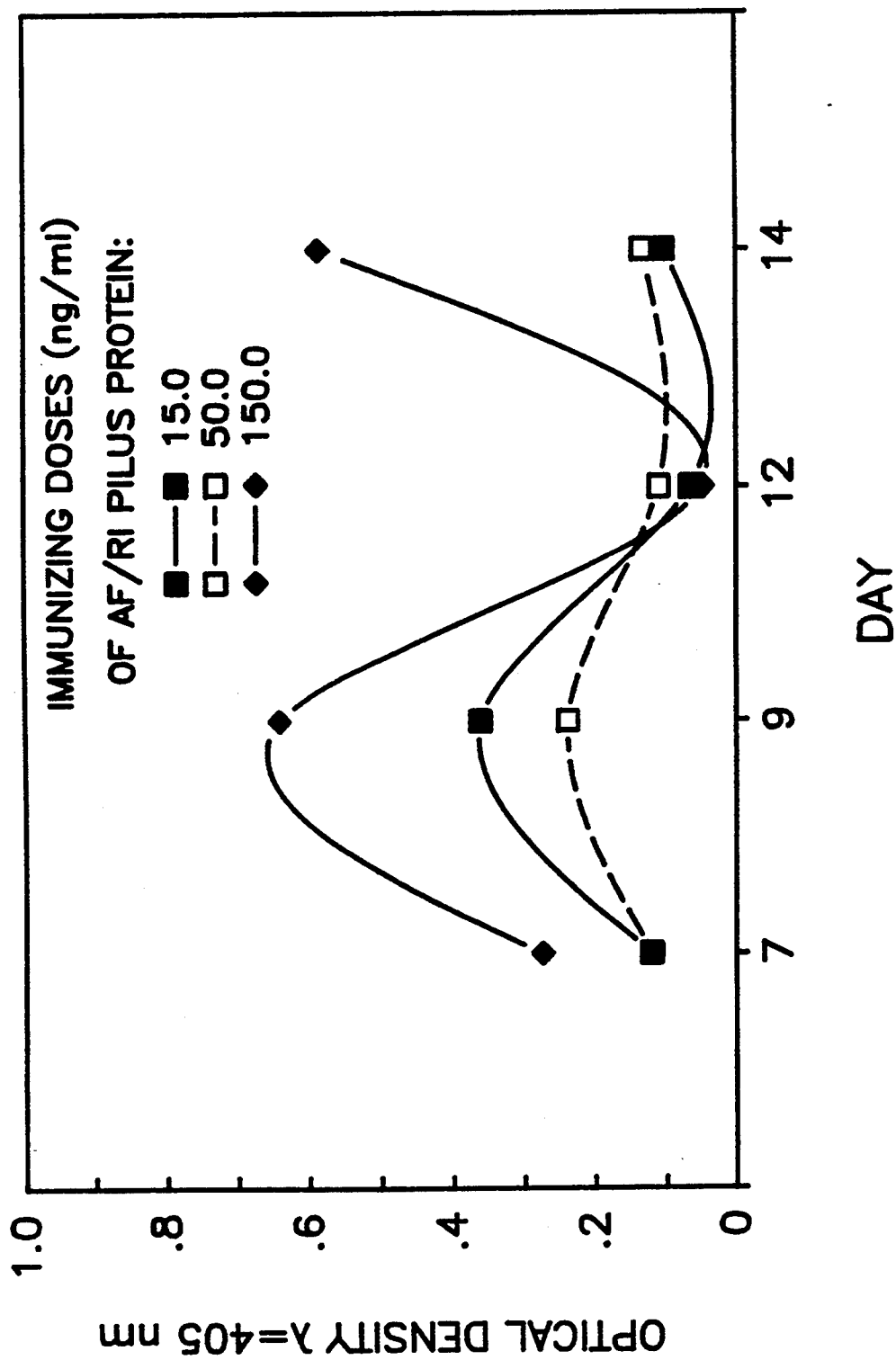
Figure 3B:
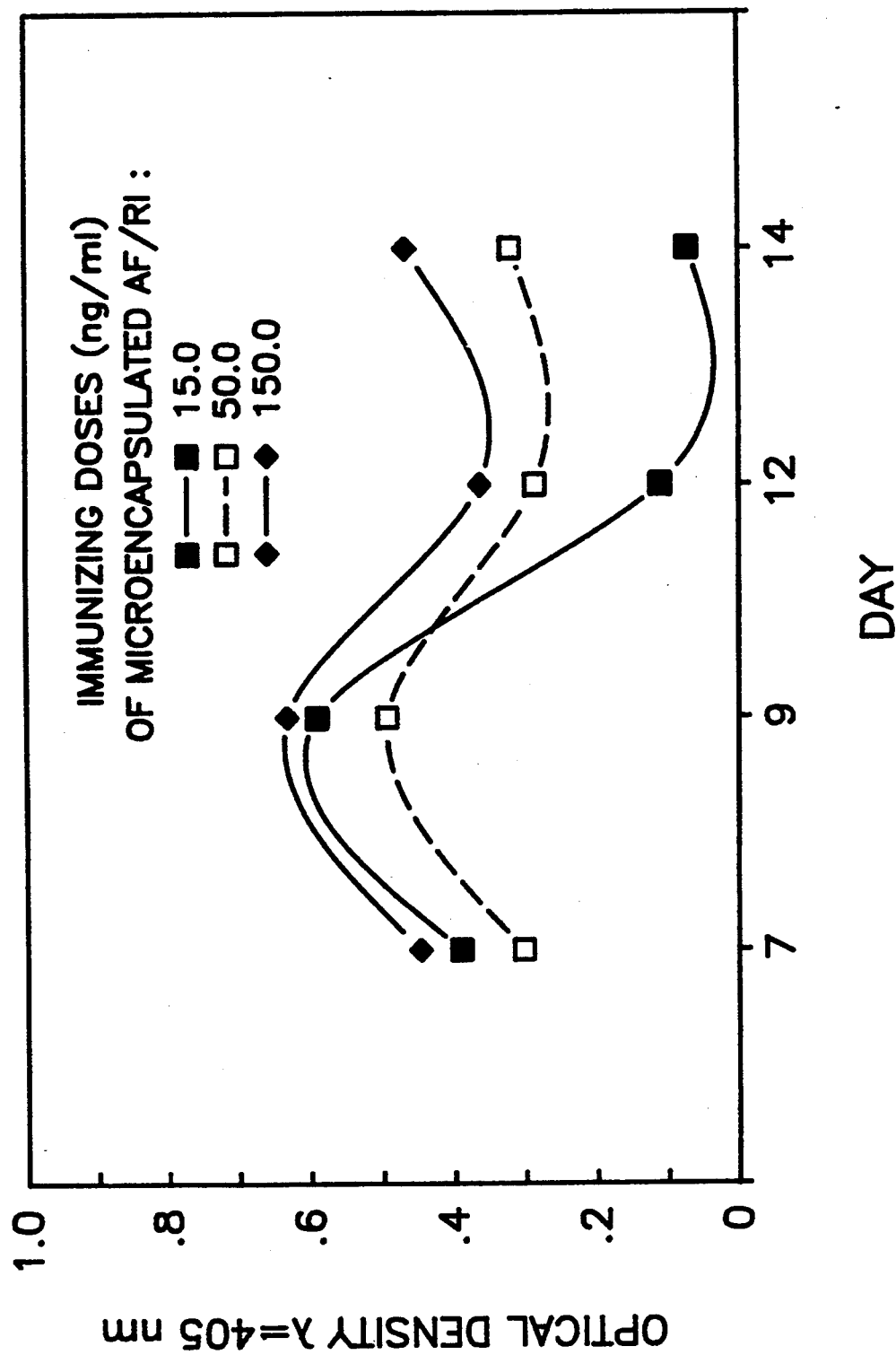
Figure 4B:
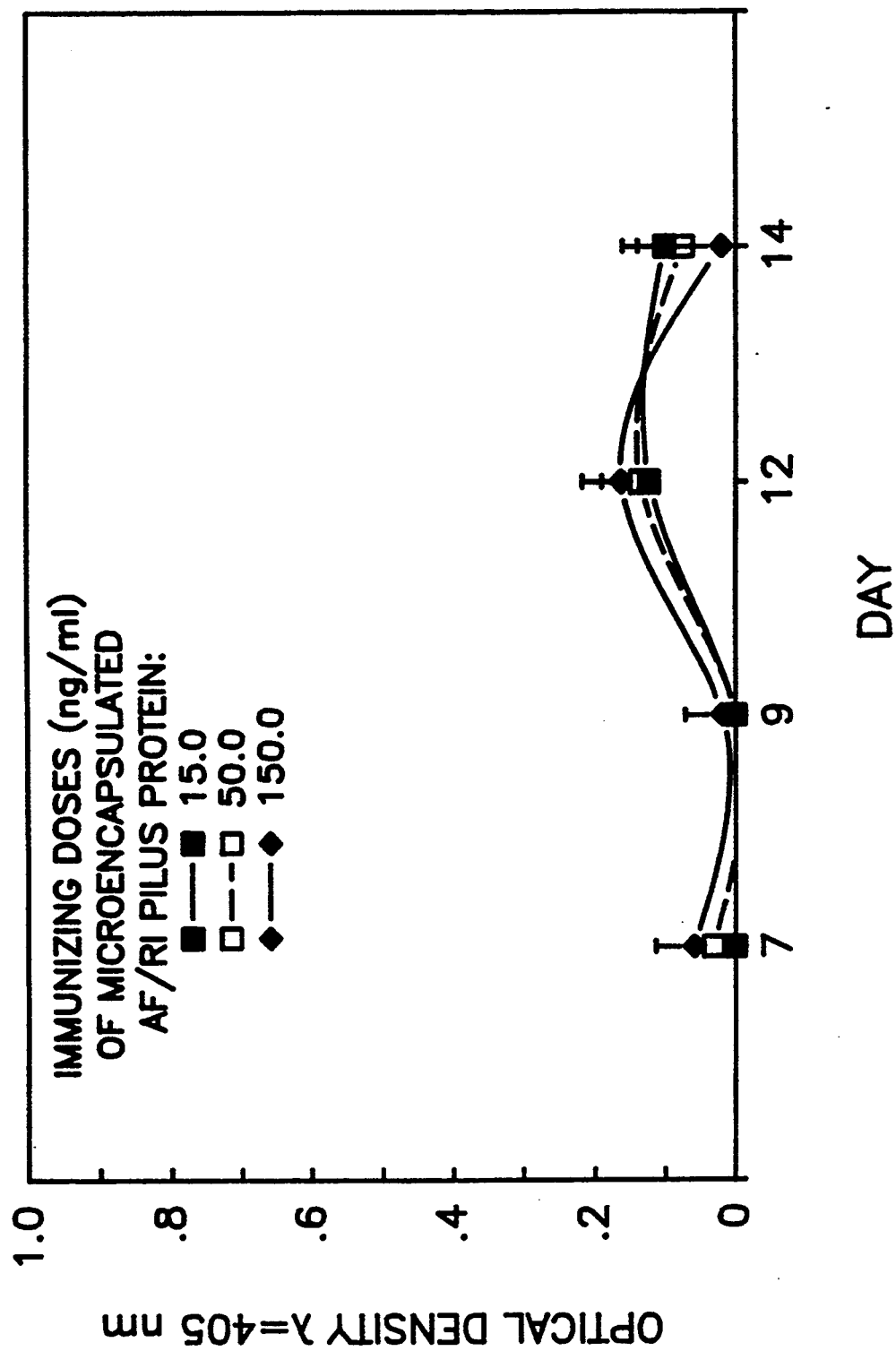
Figure 5:
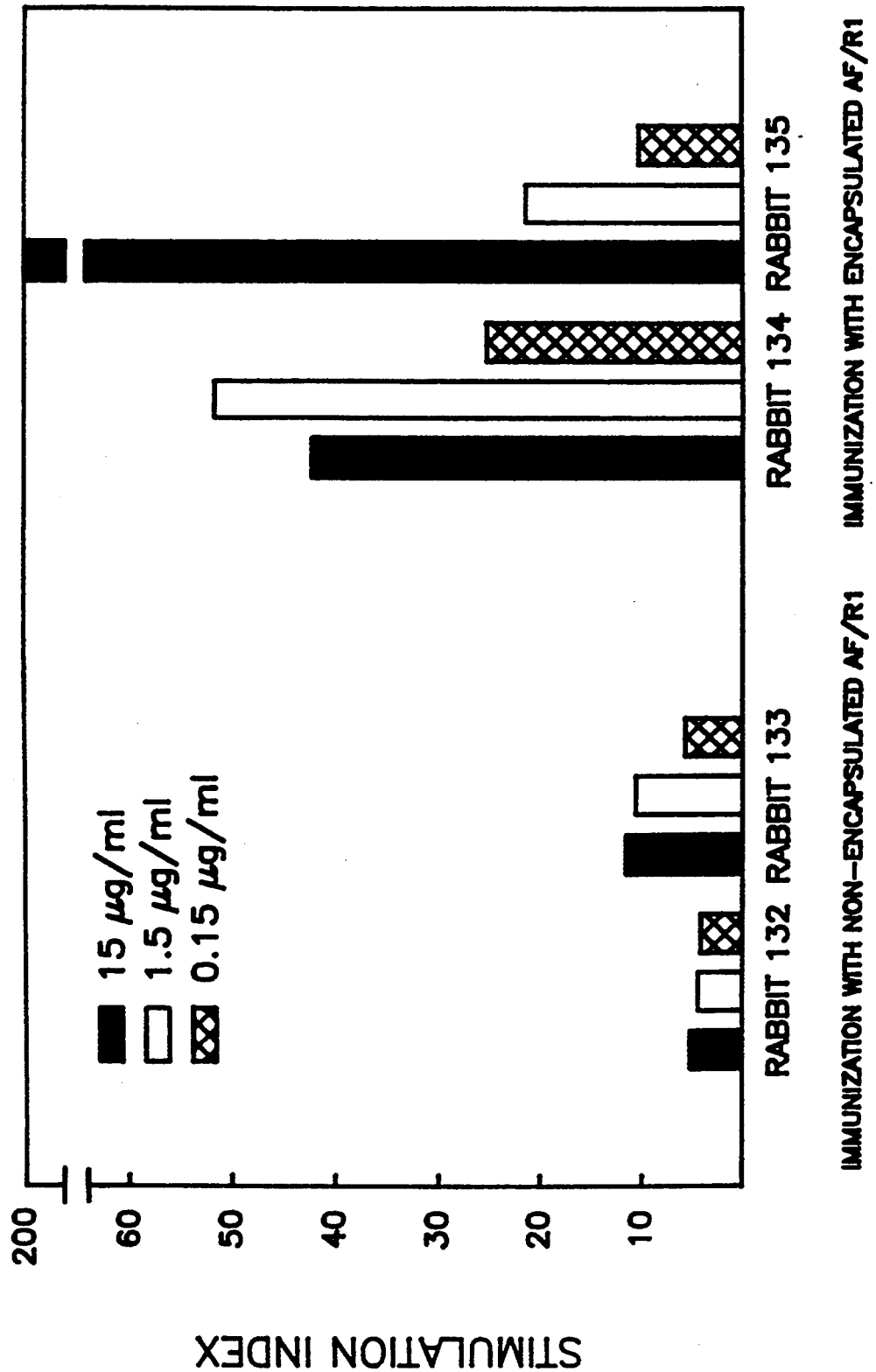
Figure 8A:
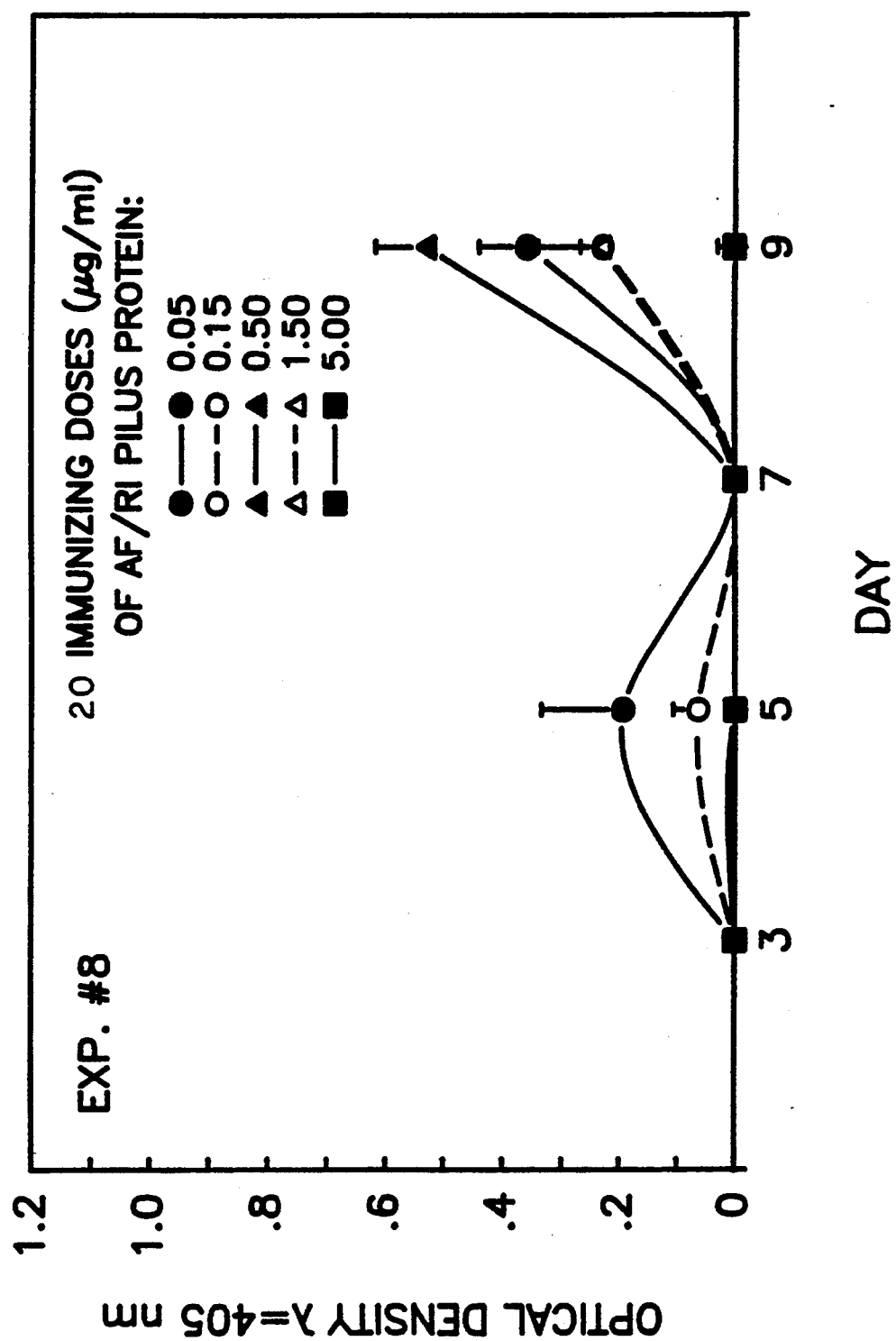
Figure 8D:
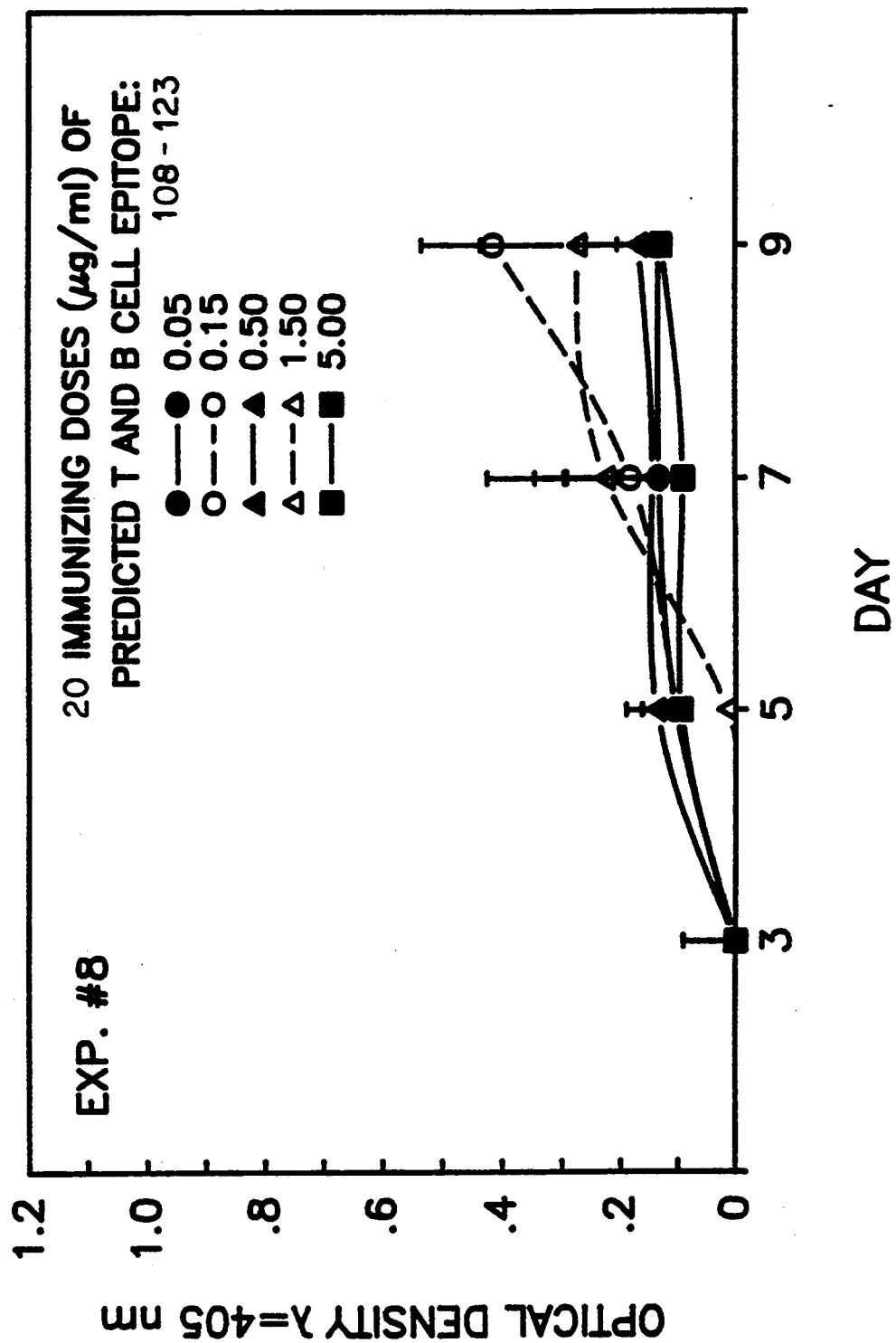
Figure 9A:
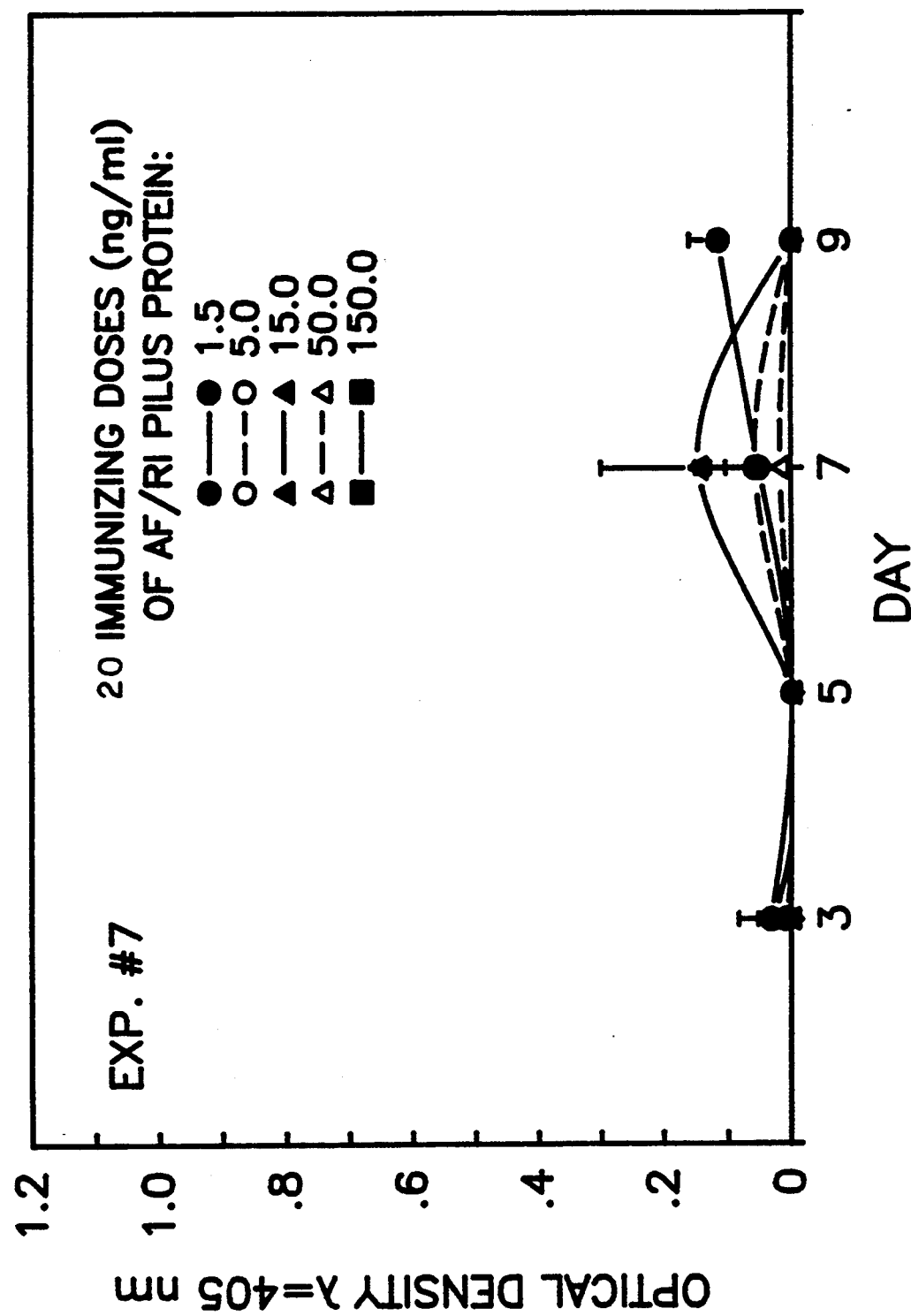
Figure 9B:
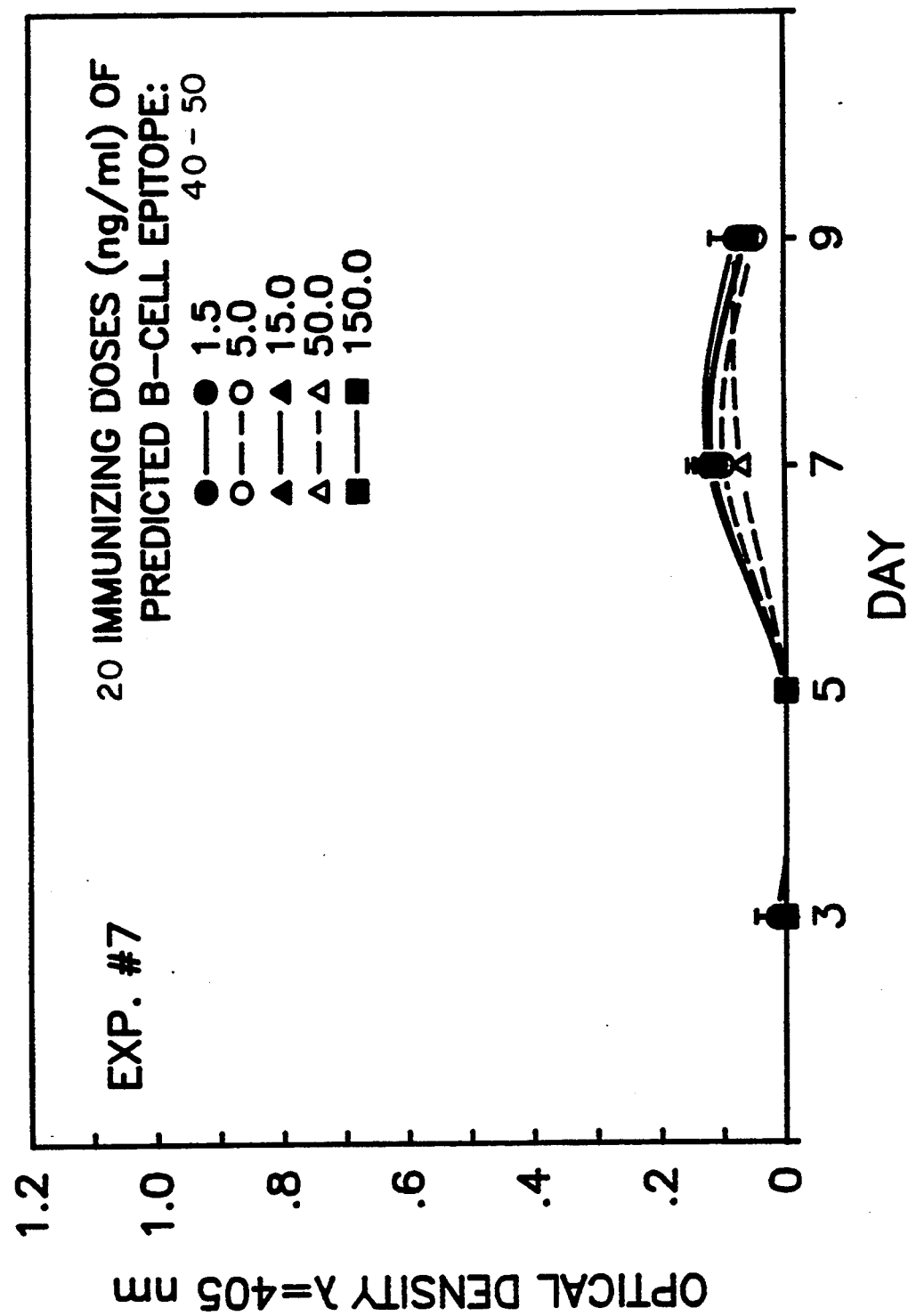
Figure 9C:
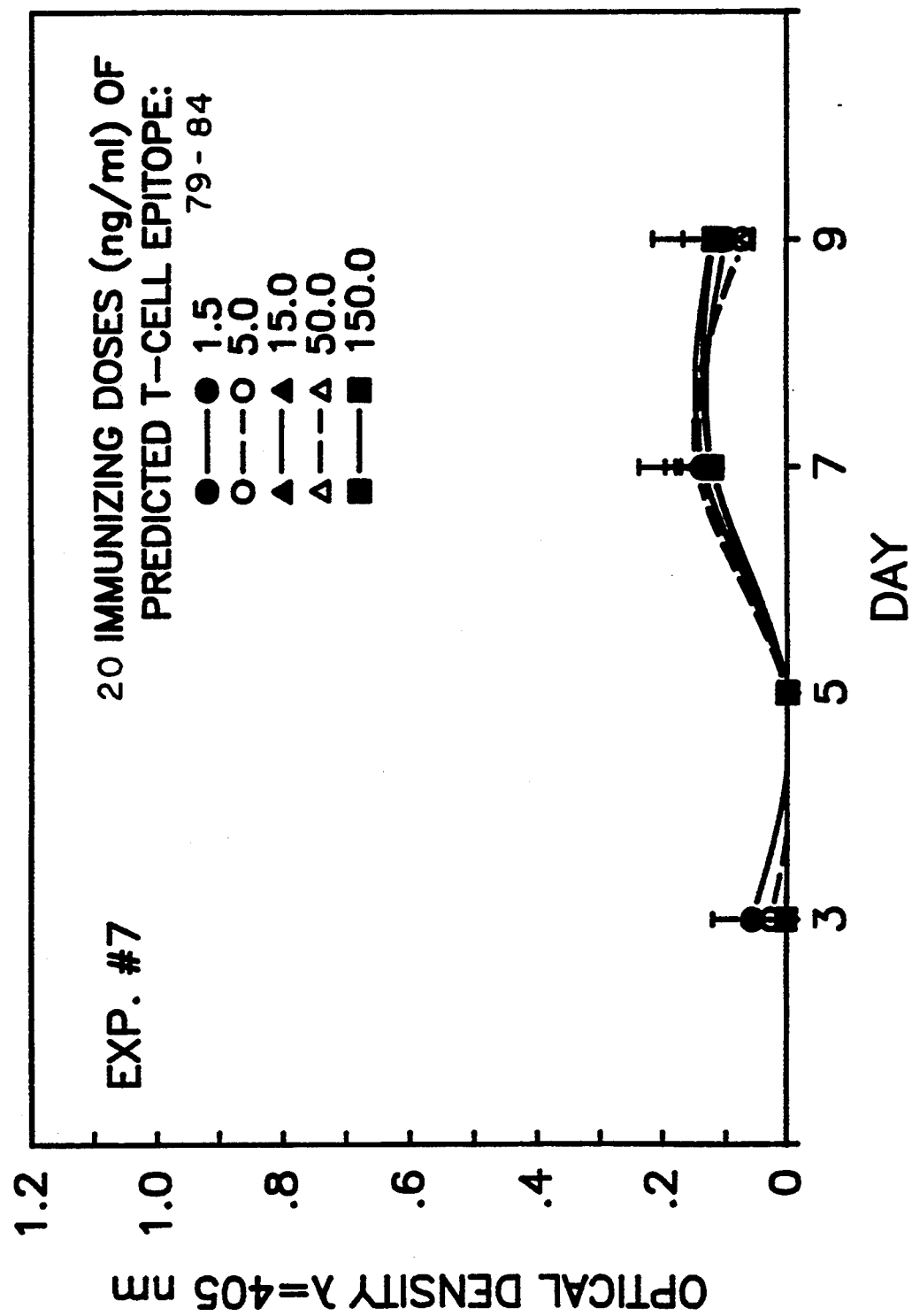
Figure 9D:
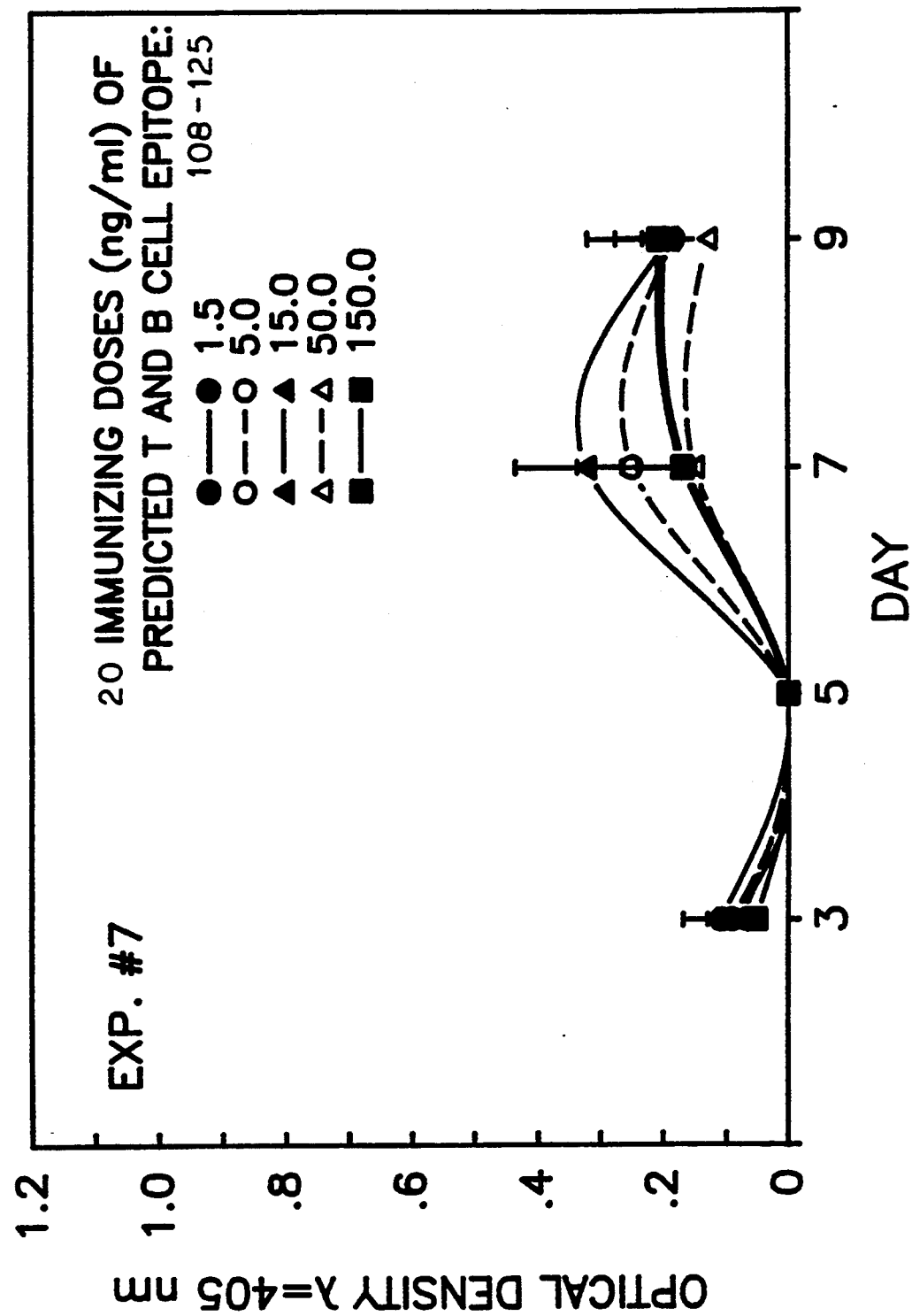
Figure 10A:
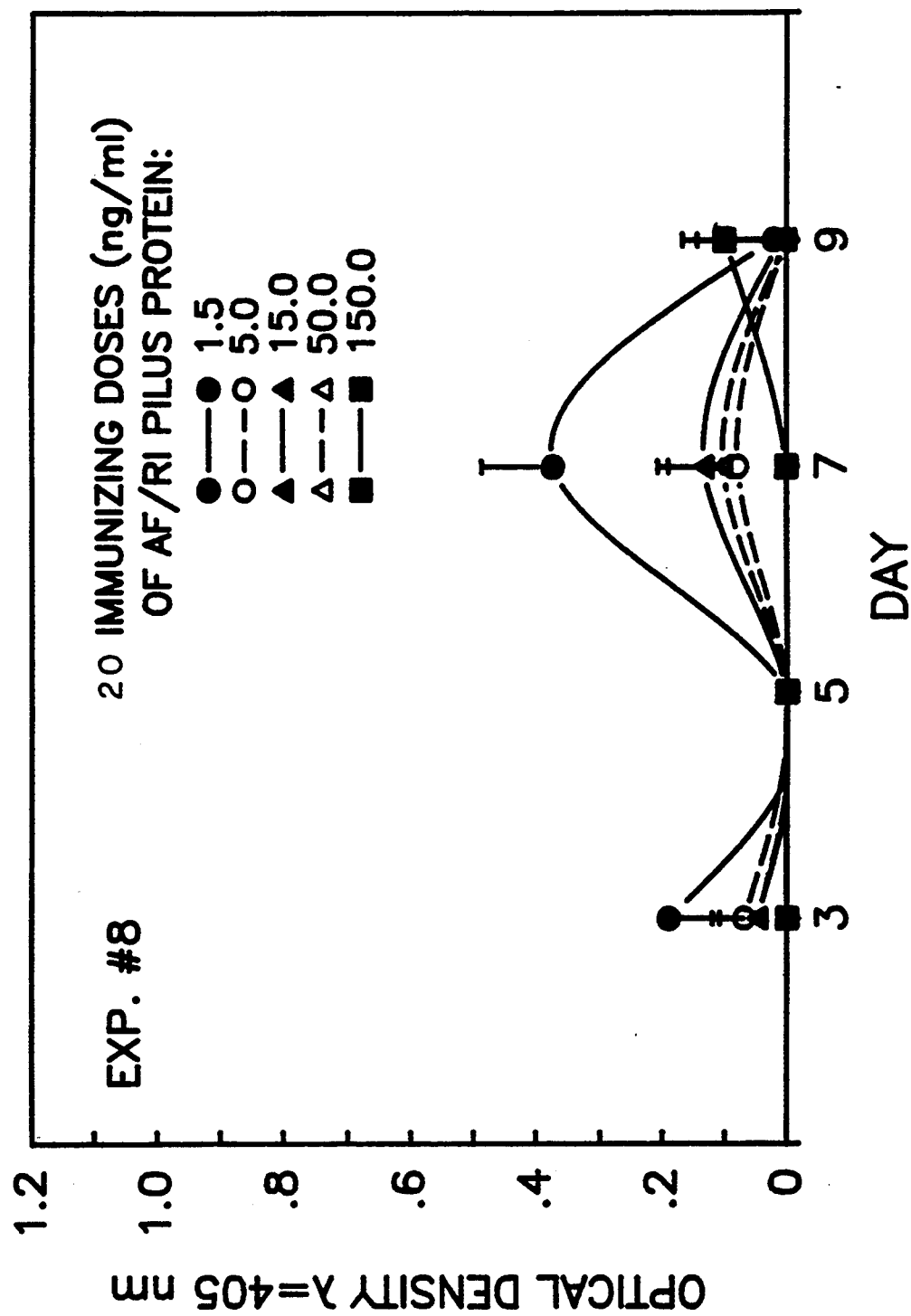
Figure 10B:
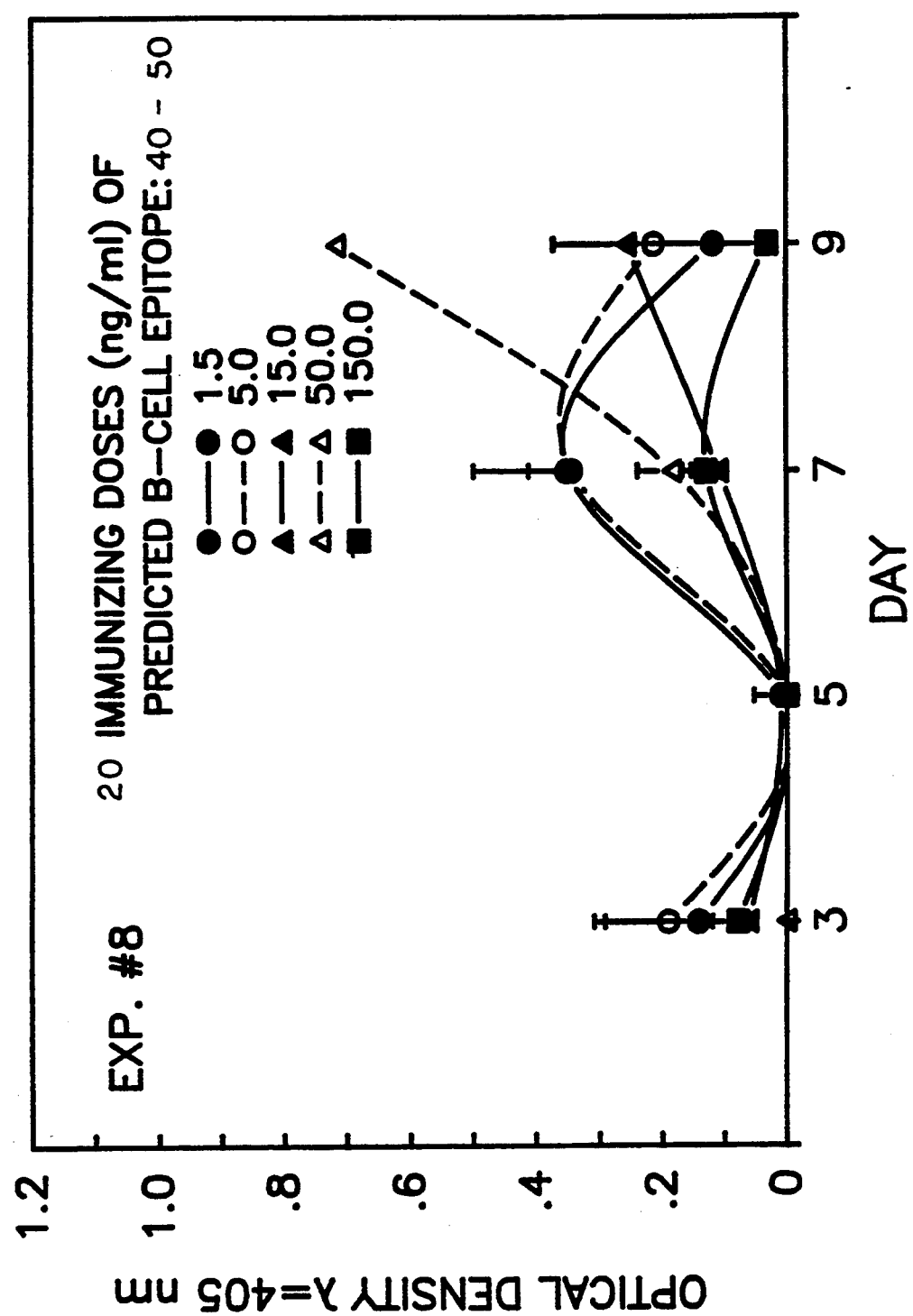
Figure 10C:
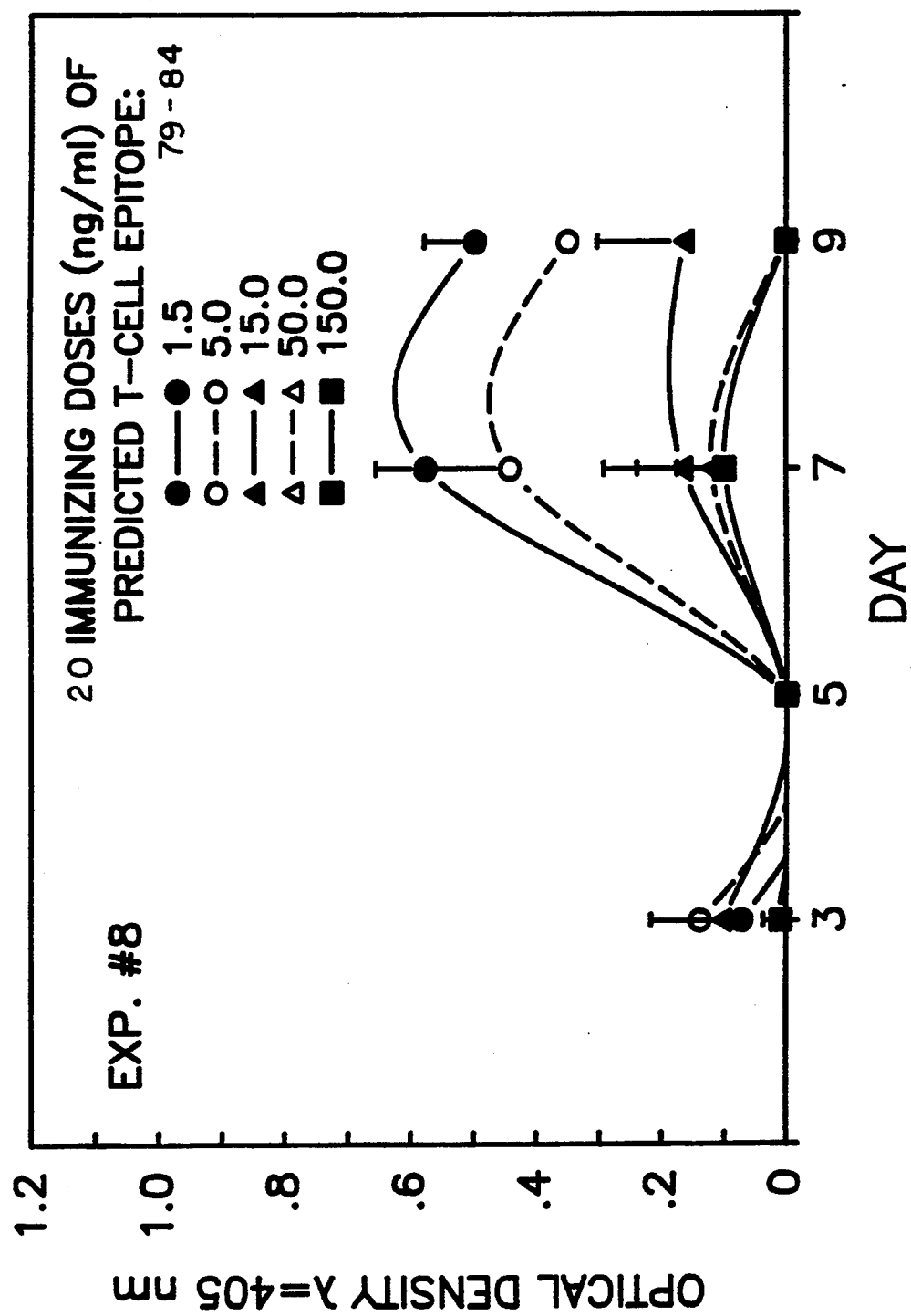
Figure 10D:
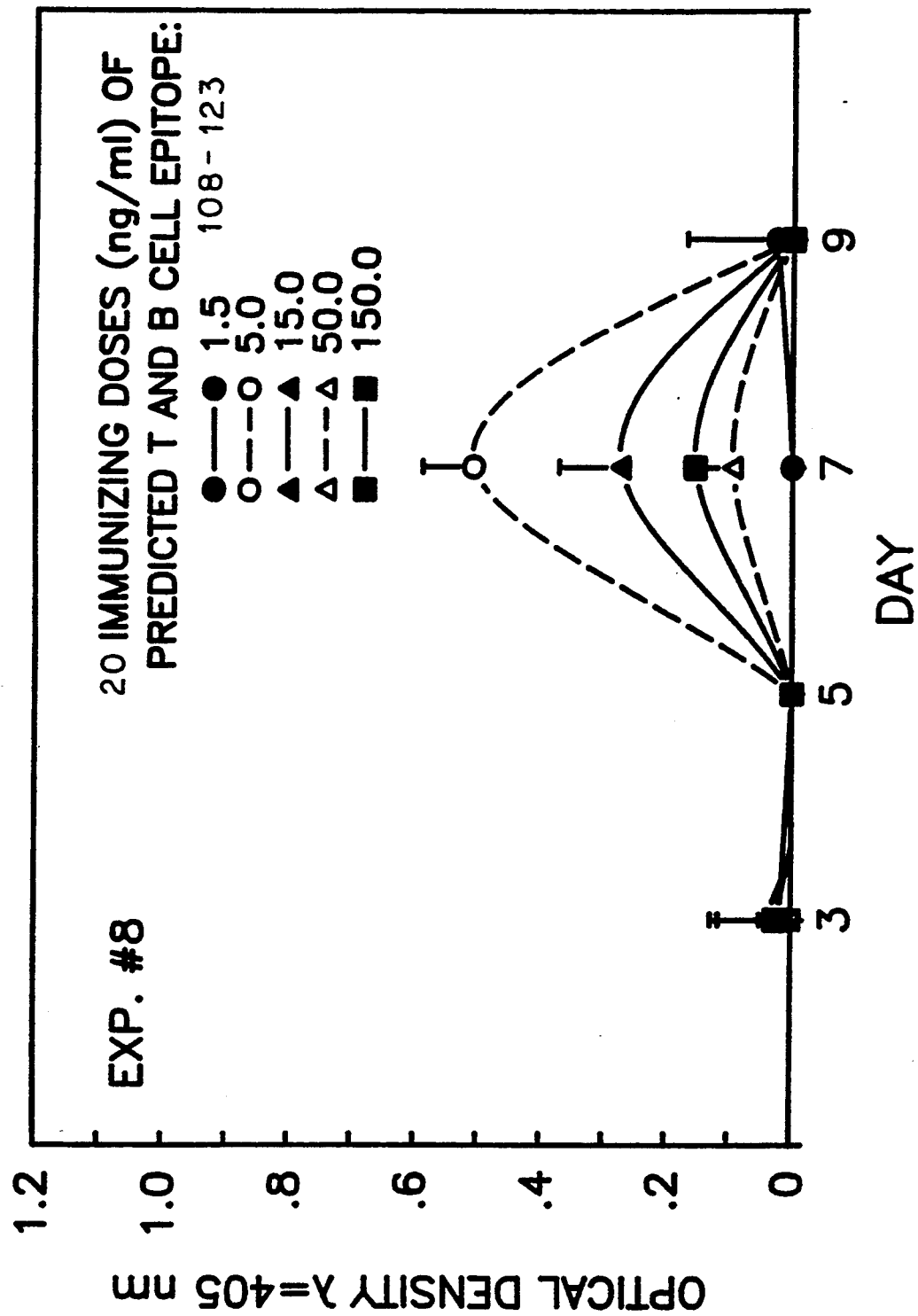
Figure 13:
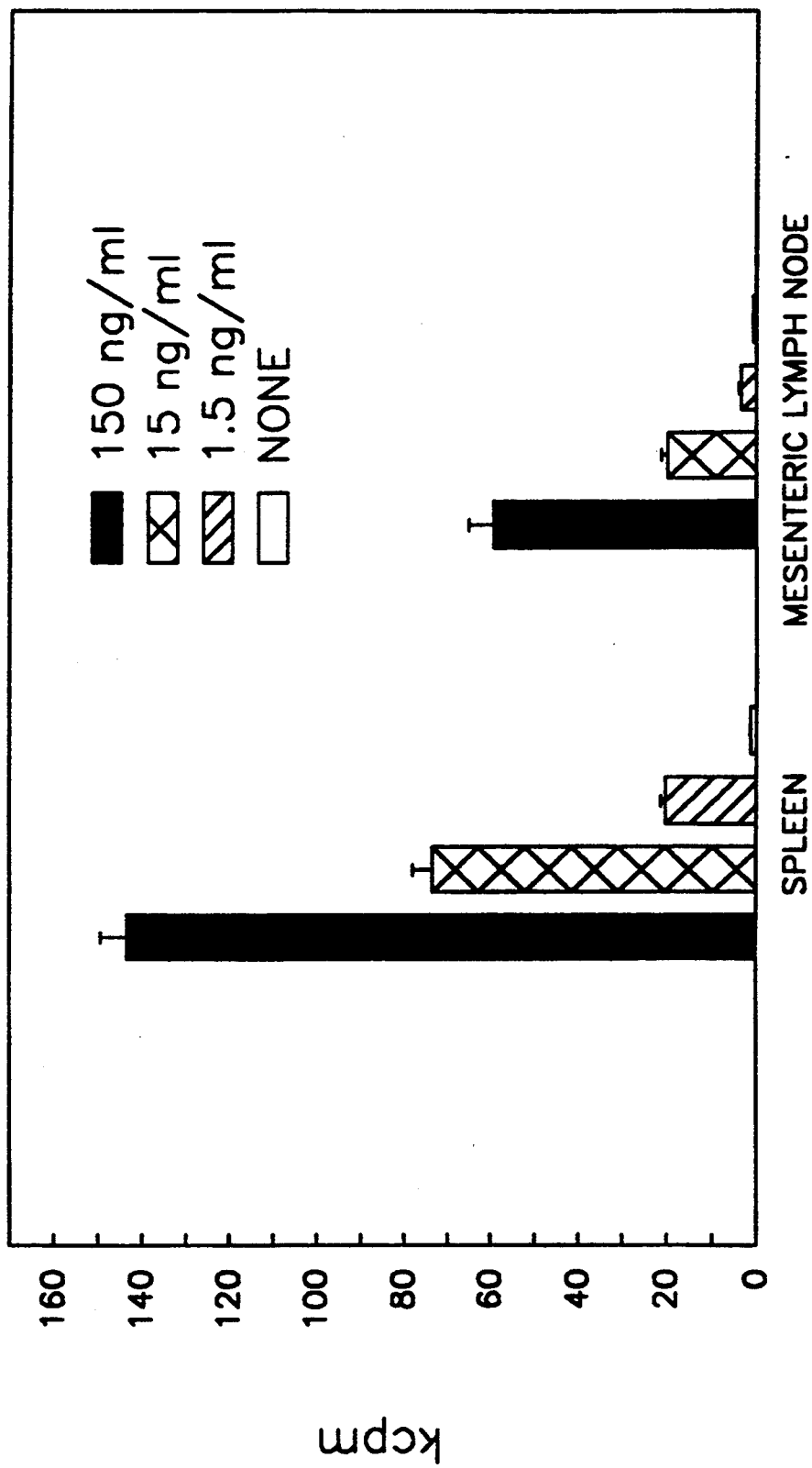
Figure 14:
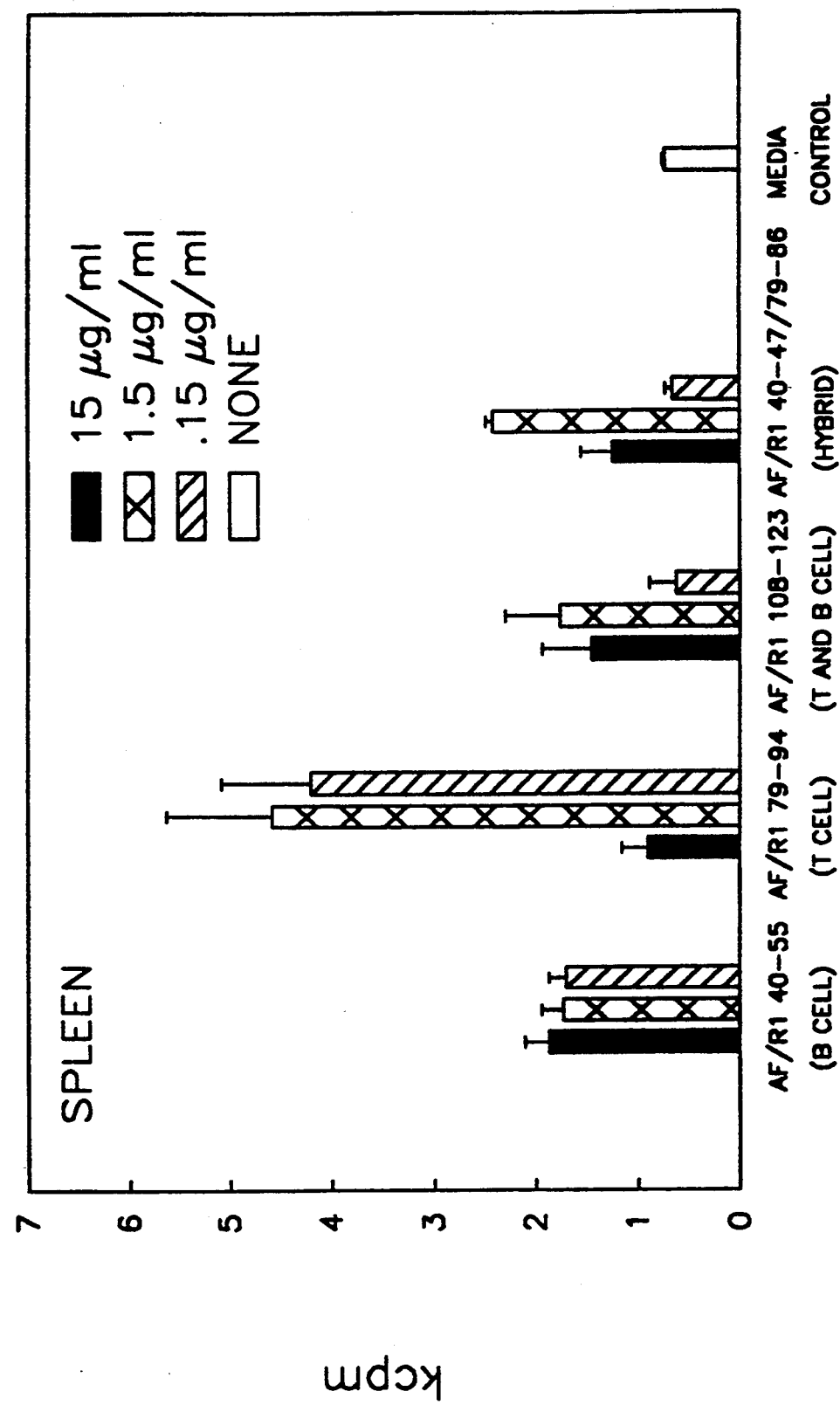
Figure 19:
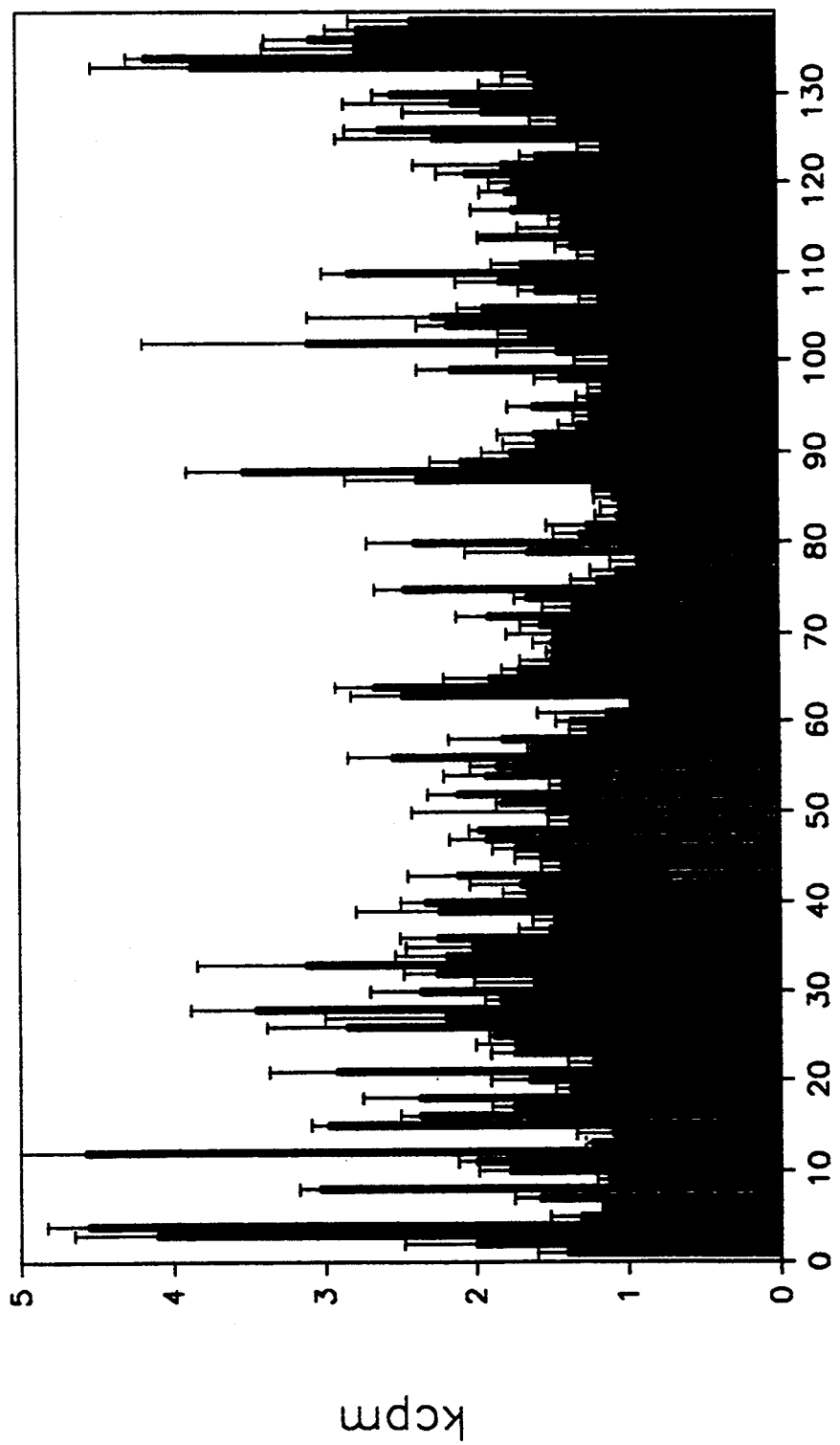
Figure 20:
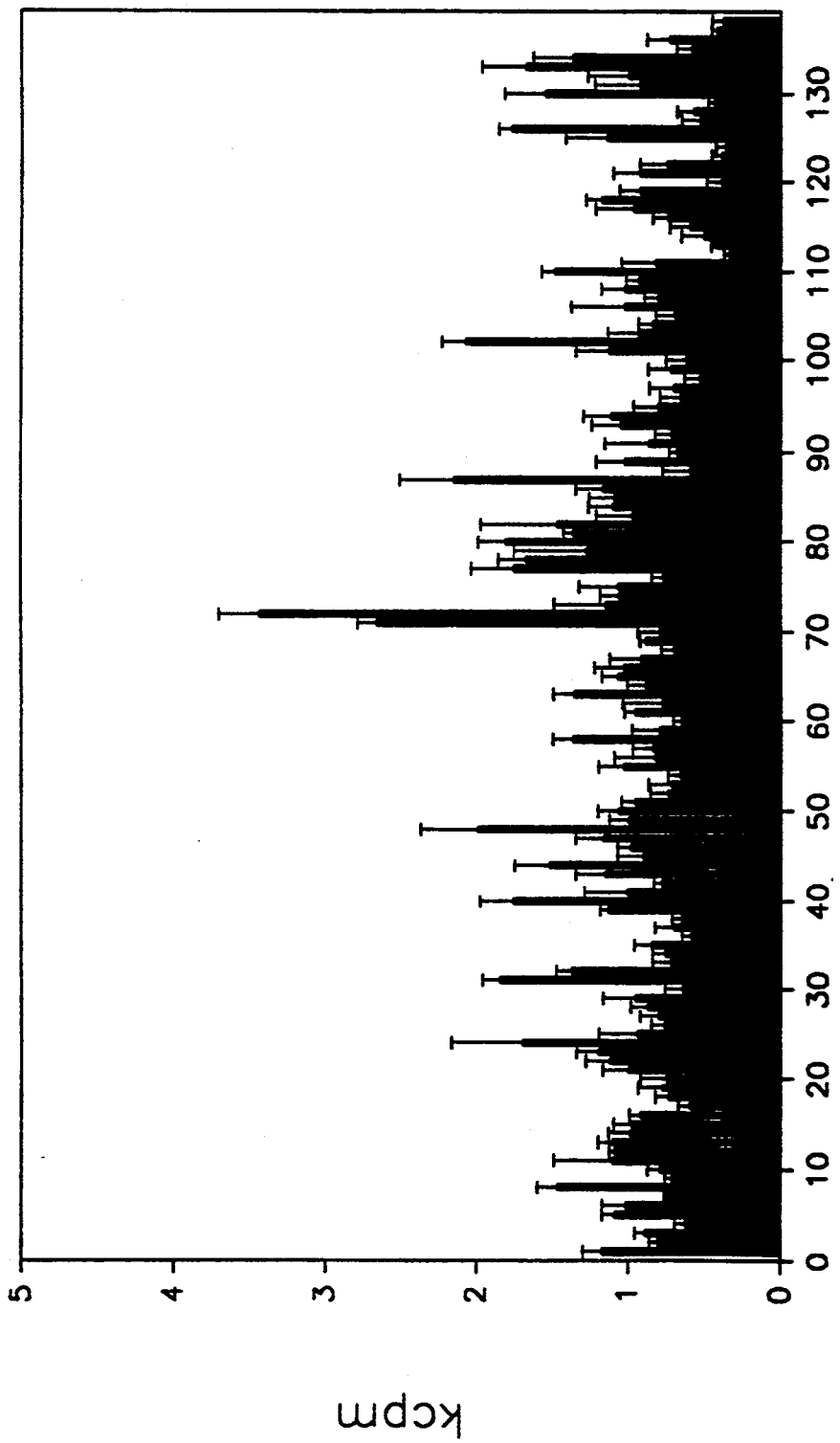
Figure 21:
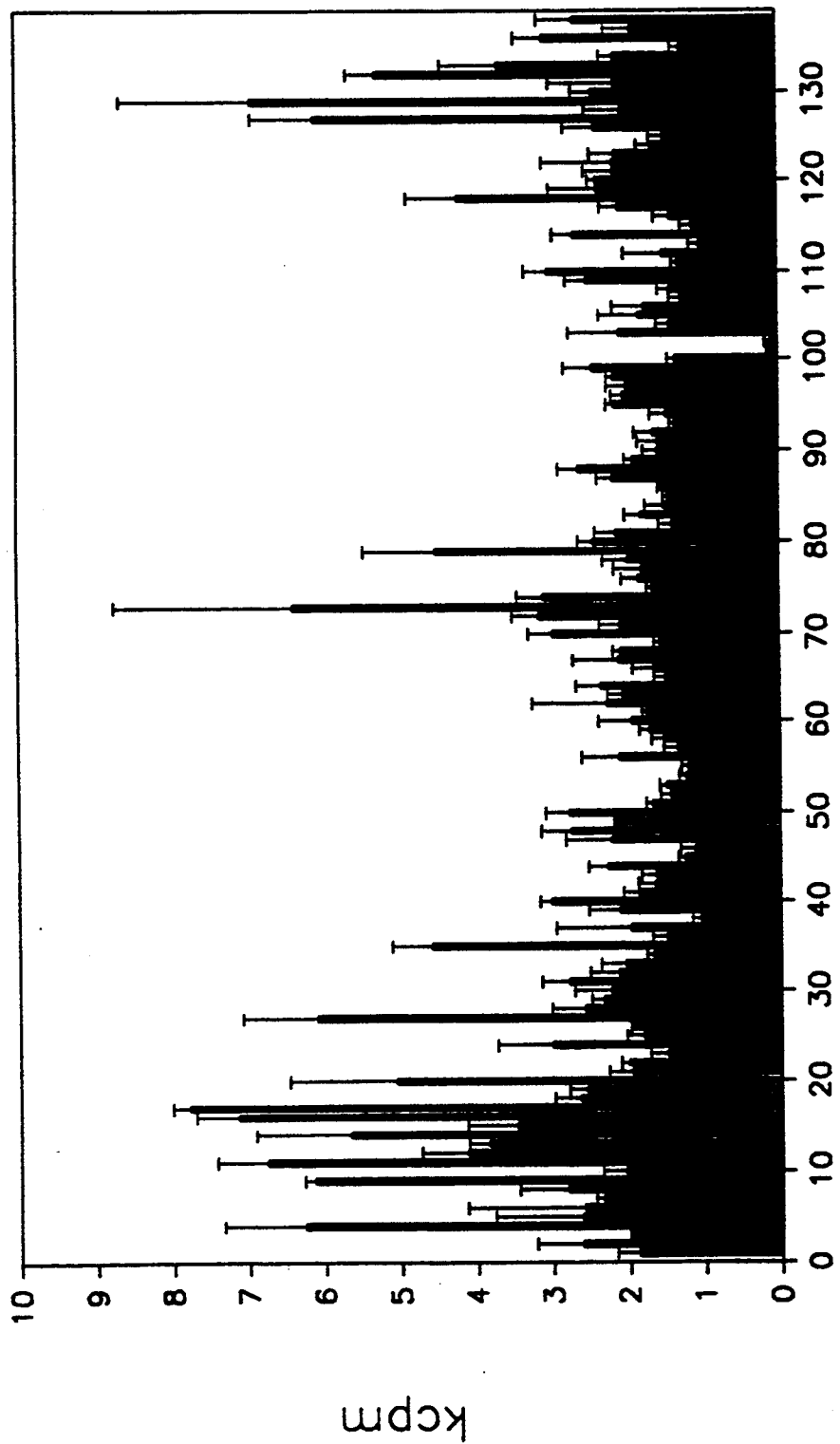
Figure 22:
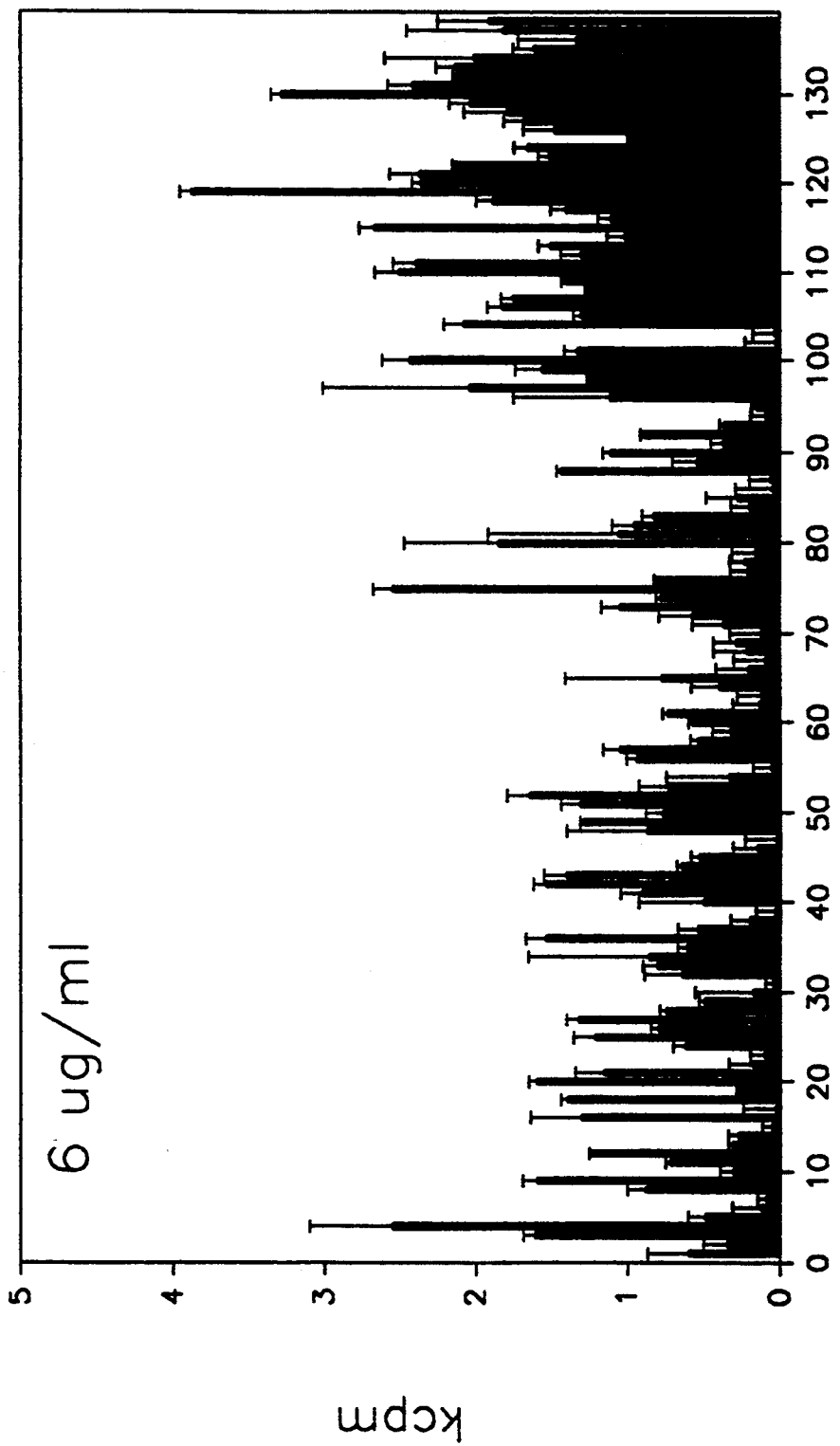
Figure 23:
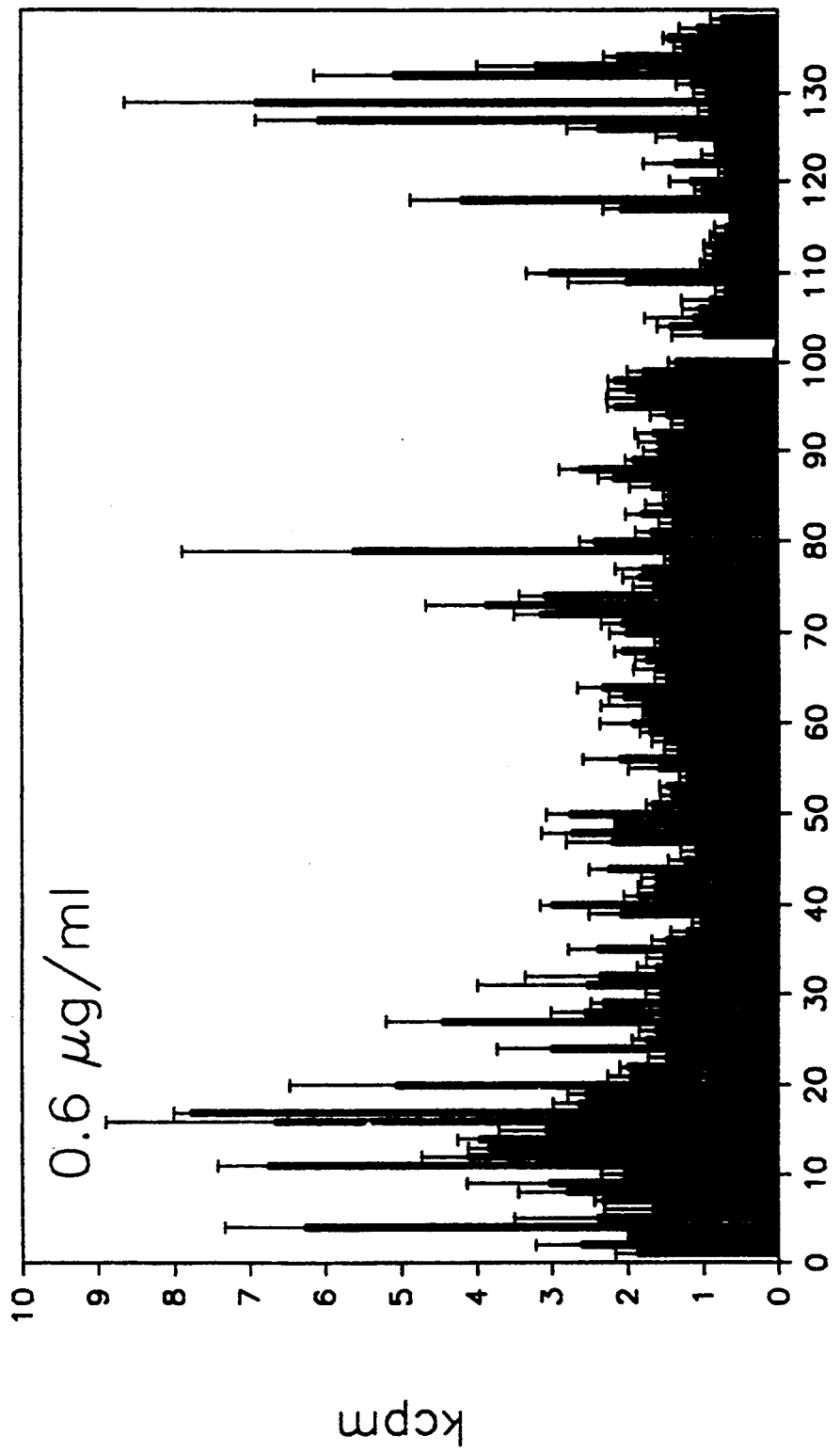
Figure 24:
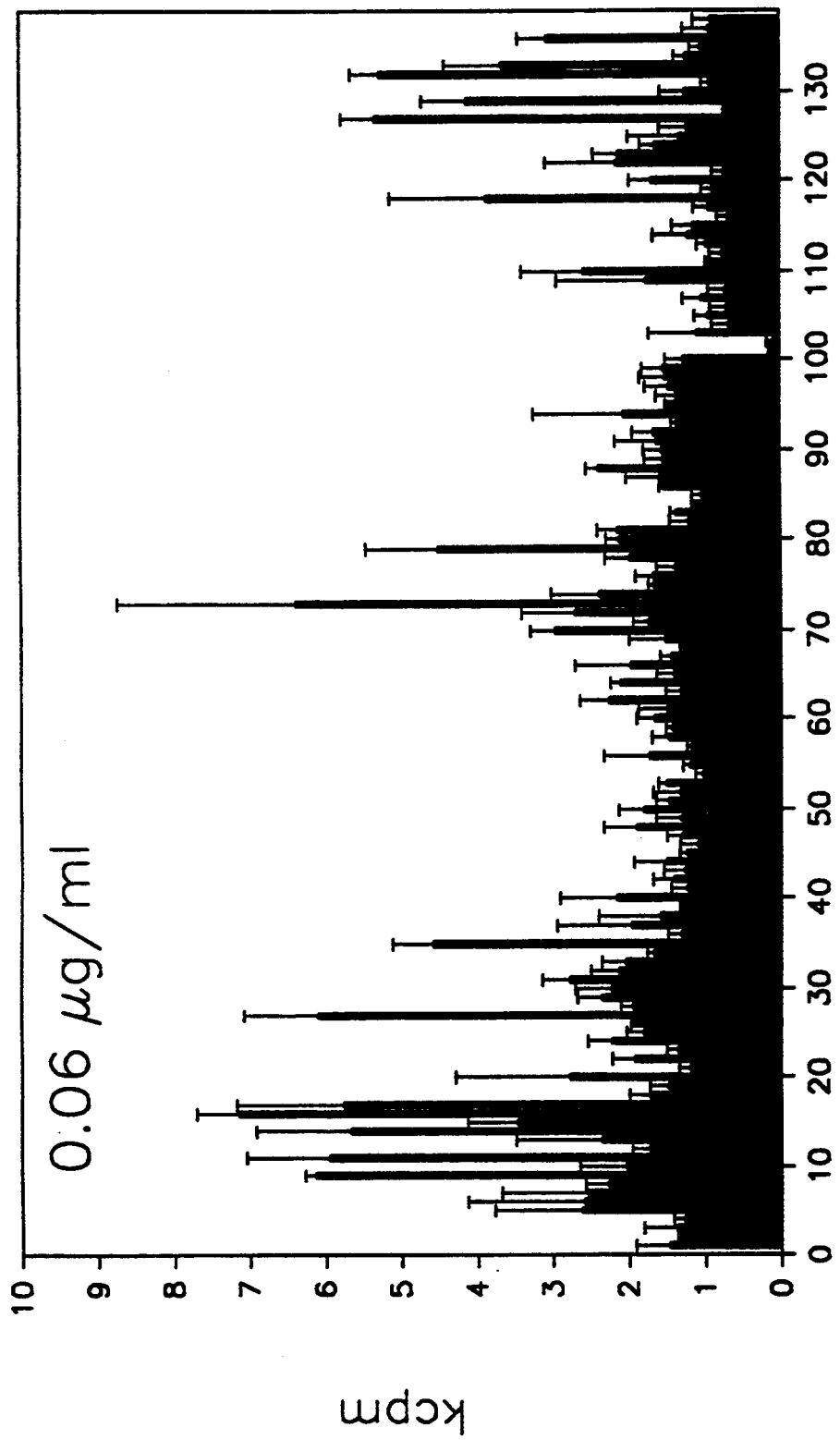
Figure 25:
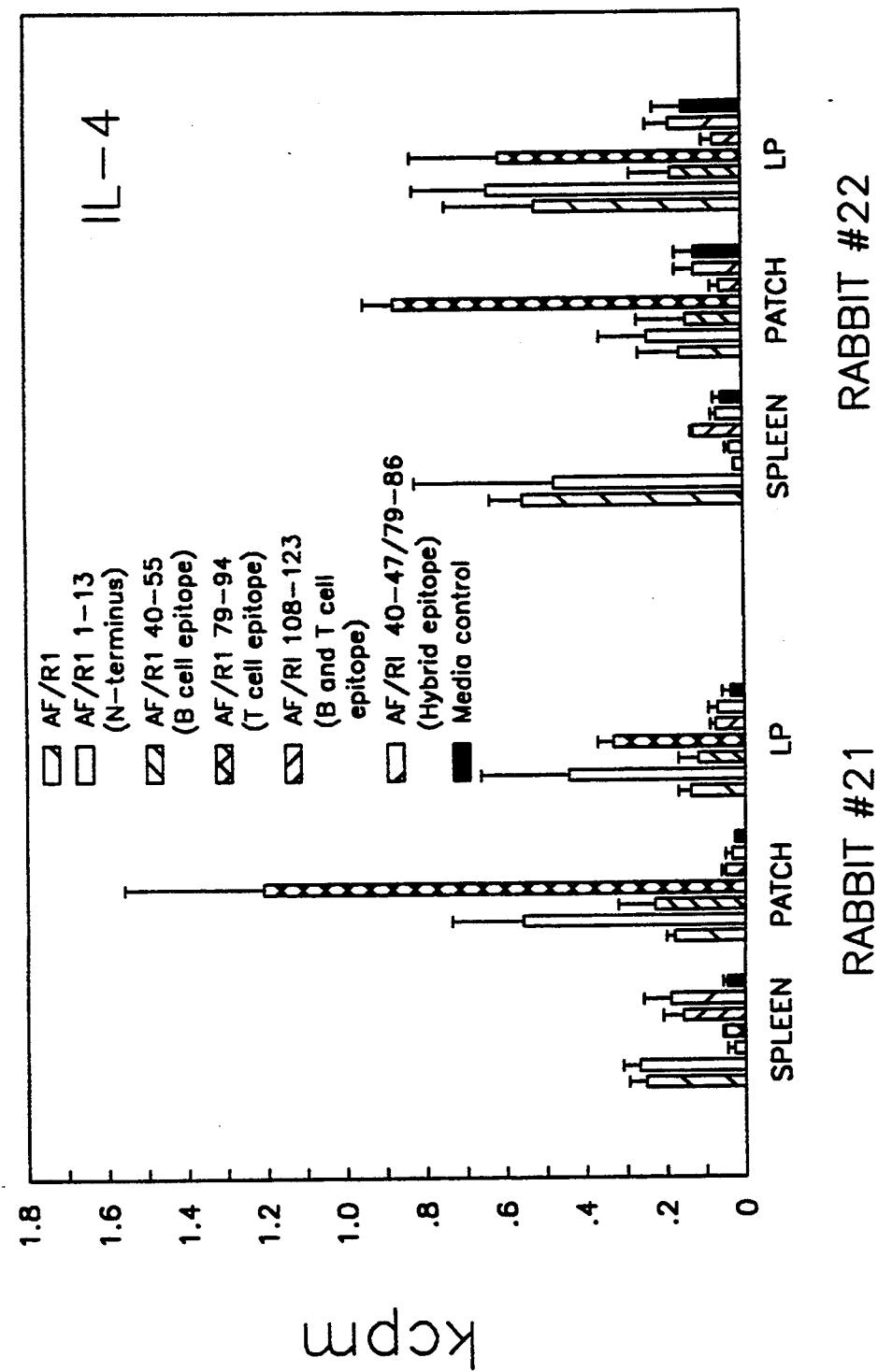

Lymphocyte proliferation of monkey spleen cells to CFA/I synthetic peptides. To determine which segments of the CFA/I protein are able to stimulate proliferation of CFA/I immune primate lymphocytes in vitro, three Rhesus monkeys were immunized with CFA/I subunits, and their splenic lymphocytes were cultured with synthetic overlapping decapeptides which represented the entire CF/I sequence. Concentrations of peptides used as antigen were 6.0, 0.6, and 0.6 ug/ml. Proliferative responses to the decapeptides were observed in each of the three monkeys (FIGS. 1-3). The majority of the responses occurred at the 0.6 and 0.06 ug/ml concentrations of antigen and within distinct regions of the protein (peptides beginning with residues 8-40, 70-80, and 27-137). A comparison of the responses at the 6.0, 0.6 and 0.06 ug/ml concentrations antigenic peptide for one monkey (2&2) are shown (FIGS. 4–6). Taking into account all concentrations of antigen tested, spleen cells from monkey 184D demonstrated a statistically significant response to decapeptides beginning with CFA/I amino acid residues 3, 4, 8, 12, 15, 21, 26, 28, 33, 88, 102, 10, 133, 134, and 136 (FIG. 19). Monkey 34 had a significant response to decapeptides beginning with residues 24, 31, 40, 48, 71, 72, 77, 78, 80, 87, and 102, 126 and 133 (FIG. 20); monkey 2Z2 responded to decapeptides which began with residues 4, 9, 11, 12, 13, 14, 15, 16, 17, 20, 27, 35, 73, 79, 18, 127, 129, 132, and 133 (FIG. 19). Peptides beginning with amino acid residues 3 through 2 were synthesized with either a glutamic acid or an asparagine substituted for the aspartic acid residue at position twelve to prevent truncated peptides. The observed responses to peptides beginning with residue 8 (monkey 184d), and residues 9, 11, 12 (monkey 2Z2) occurred in response to peptides that had the glutamic acid substitution. However, the observed responses to peptides beginning with residue 3, 4, and 12 (monkey 184D), a well as residue 4 (monkey 2Z2) occurred in response to peptides that had the asparagine substitution. Monkey 34 did not respond to any of the peptides that had the substitution at position twelve. All other responses shown were to the natural amino acid sequence of the CFA/I protein. Statistical significance was determined by comparing the cpm of quadruplicate wells cultured with the CFA/I peptides to the cpm of wells cultured with the CFA/I peptides to the cpm of wells cultured with a control peptide.

Analysis of decapeptides that supported proliferation of lymphocytes from CFA/I immune animals. Of the 39 different peptides that supported proliferative responses, thirty contained a serine residue, 19 contained a serine at either position 2, 3, or 4, and nine had a serine specifically at position 3. Some of the most robust responses were to the peptides that contained a serine residue at the third position. The amino acid sequence of four such peptides is shown in Table 3.

VII. DETAILED DESCRIPTION OF THE INVENTION

Applicants have discovered efficacious pharmaceutical compositions wherein the relative amounts of antigen to the polymeric matrix are within the ranges of 0.1 to 1.5% antigen (core loading) and 99.9 to 98.5% polymer, respectively. It is preferred that the relative ratio between the lactide and glycolide component of the poly(DL-lactide-co-glycolide) (DL-PLG) is within the range of 52:48 to 0: 100. However, it is understood that effective core loads for certain antigens will be influenced by its microscopic form (i.e. bacteria, protozoa, viruses or fungi) and type of infection being prevented. From a biological perspective, the DL-PLG or glycolide monomer excipient are well suited for in vitro drug (antigen) release because they elicit a minimal inflamatory response, are biologically compatible, and degrades under physiologic conditions to products that are nontoxic and readily metabolized.

Surprisingly, applicants have discovered an extremely effective method for the protection against bacterial or viral infections in the tissue of a mammal (human or nonhuman animal) caused by enteropathogenic organisms comprising administering orally to said animal an immunogenic amount of a pharmaceutical composition consisting essentially of an antigen encapsulated within a biodegradable polymeric matrix. When the polymeric matrix is DL-PLG, the most preferred relative ratio between the lactide and glycolide component is within the range of 48:52 to 52:48. The bacterial infection can be caused by bacteria (including any derivative thereof) which include *Salmonella typhi, Shigella Sonnei, Shigella flexnet, Shigella dysenteriae, Shigella boydii, Escheria coli, Vibro Cholera, yersinia, staphylococcus, clostridium* and *campylobacter.* Representative viruses contemplated within the scope of this invention, susceptible to treatment with the above-described pharmaceutical compositions, are quite extensive. For purposes of illustration, a partial listing of these viruses (including any derivative thereof) include hepatitis A, hepatitus B, rotaviruses, polio virus human immunodeficiency viruses (HIV), Herpes Simplex virus type 1 (cold sores), Herpes Simplex virus type 2 (Herpesvirus genitalis), Varicella-zoster virus (chicken pox, shingles), Epstein-Barr virus (infectious mononucleosis; glandular fever; and Burkittis lymphoma), and cytomegalo viruses.

A further representation description of the instant invention is as follows:

A. (1) To homogeneously disperse antigens of enteropathic organisms within the polymeric matrix of biocompatible and biodegradable microspheres, 1 nanogram (ng) to 12 microns in diameter, utilizing equal molar parts of polymerized lactide and glycolide (50:50 DL-PLG, i.e. 48:52 to 52:48 DL-PLG) such that the core load is within the range of about 0.1 to 1.5% by volume. The microspheres containing the dispered antigen can then be used to immunize the intestine to produce a humoral immune response composed of secretory antibody, serum antibody and a cellular immune response consisting of specific T-cells and B-cells. The immune response is directed against the dispered antigen and will give protective immunity against the pathogenic organism from which the antigen was derived.

(2) AF/R1 pilus protein is an adherence factor that allows *E. coli* RDEC-1 to attach to rabbit intestinal brush borders thus promoting colonization resulting in diarrhea. AF/R1 pilus protein was homogeneously dispered within a polymeric matrix of biocompatible and biodegradable microspheres, 1–12 microns in diameter (FIG. 1 and photograph 1) using equal molar parts of polymerized lactide and glycolide (50:50 DL-PLG) such that the core load was 0.62% by weight.

(3) The microspheres were found to contain immunogenic AF/R1 by immunizing both rabbit spleen (FIG. 2) and Peyer's patch (FIG. 3) B-cells in vitro. The resultant cell supernatants contained specific IgM antibody which recognized the AF/R1. The antibody response was comparable to immunizing with AF/R1 alone.

(4) Microspheres containing 50 micrograms of AF/R1 were used to intraintestinally (intraduodenally) immunize rabbits on two separate occasions 1 week apart. One week later, compared to rabbits receiving AF/R1 alone, the intestinal lymphoid tissue, Peyer's patches, demonstrated an enhanced cellular immune response to AF/R1 and to three AF/R1 linear peptide fragments 40–55, 79–94 and 108–123 by both lymphocyte transformation (T-cells) (FIGS. 4 and 5) and antibody producing B-cells (FIGS. 6 and 7). Similarly enhanced B-cell responses were also detected in the spleen (FIGS. 8 and 9). An enhanced T-cell response was also detected in the mesenteric lymph node and the spleen to one AF/R1 peptide fragment, 40–55 (FIGS. 10 and 11). The cellular immune response at two weeks was too early for either a serum or secretory antibody response (See Results in Table 1); but indicates that a secretory antibody response will develop such that the rabbits so immunized could be protected upon challenge with the *E. coli* RDEC-1.

B. Microspheres do not have to be made up just prior to use as with liposomes. Also liposomes have not been effective in rabbits for intestinal immunization of lipopolysaccharide antigens.

C. (1) Only a small amount of antigen is required (ugs) when dispersed within microspheres compared to larger amounts (mgms) when antigen is used alone for intestinal immunization.

(2) Antigen dispersed within microspheres can be used orally for intestinal immunization whereas antigen alone used orally even with gastric acid neutralization requires a large amount of antigen and may not be effective for intestinal immunization.

(3) Synthetic peptides with and without attached synthetic adjuvants representing peptide fragments of protein antigens can also be dispersed within microspheres for oral-intestinal immunization. Free peptides would be destroyed by digestive processes at the level of the stomach and intestine. Any surviving peptide would probably not be taken up by the intestine and therefore be ineffective for intestinal immunization.

(4) Microspheres containing antigen maybe placed into gelatin-like capsules for oral administration and intestinal release for improved intestinal immunization.

(5) Microspheres promote antigen uptake from the intestine and the development of cellular immune (T-cell and B-Cell) responses to antigen components such as linear peptide fragments of protein antigens.

(6) The development of intestinal T-cell responses to antigens dispersed within microspheres indicate that T-cell immunological memory will be established leading to long-lived intestinal immunity. This long-lived intestinal immunity (T-cell) is very difficult to establish by previous means of intestinal immunization. Failure to establish long-lived intestinal immunity is a fundamental difficulty for intestinal immunization with non-viable antigens. Without intestinal long-lived immunity only a short lived secretory antibody response is established lasting a few weeks after which no significant immunological protection may remain.

D. (1) Oral intestinal immunization of rabbits against *E. coli* RDEC-1 infection using either whole killed organisms, pilus protein preparations or lipopolysaccharide preparations.

(2) Microspheres containing adherence pilus protein AF/R1 or its antigen peptides for oral intestinal immunization of rabbits against RDEC-1 infection.

(3) Oral-intestinal immunization of humans against enterotoxigenic *E. coli* infection using either whole killed organisms, pilus protein preparations or lipopolysaccharide preparations.

(4) Microspheres containing adherence pilus proteins CFA/I, II, III and IV or their antigen peptides for oral intestinal immunization of humans against human enterotoxigenic *E. coli* infections.

(5) Oral-intestinal immunization of humans against other enteric pathogens as salmonella, shigella, camphlobacter, hepatitis-A virus, rota virus and polio virus.

(6) Oral-intestinal immunization of animals and humans for mucosal immunological protection at distal mucosal sites as the bronchial tree in lungs, genito-urinary tract and breast tissue.

E. (1) The biocompatible, biodegradable co-polymer has a long history of being safe for use in humans since it is the same one used in resorbable suture material.

(2) By using the microspheres, we are now able to immunize the intestine of animals and man with antigens not normally immunogenic for the intestinal mucosa because they are either destroyed in the intestine, unable to be taken up by the intestinal mucosa or only weakly immunogenic if taken up.

(3) Establishing long-lived immunological memory in the intestine is now possible because T-cells are immunized using microspheres.

(4) Antigens that can be dispersed into microspheres for intestinal immunization include the following: proteins, glycoporteins, synthetic peptides, carbohydrates, synthetic polysaccharides, lipids, glycolipids, lipoopolysaccharides (LPS), synthetic lipopolysaccharides and with and without attached adjuvants such as synthetic muramyl dipeptide derivatives.

(5) The subsequent immune response can be directed to either systemic (spleen and serum antibody) or local (intestine, Peyer's patch) by the size of the microspheres used for the intestinal immunization. Microspheres 5–10 microns in diameter remain within macrophage cells at the level of the Peyer's patch in the intestine and lead to a local intestinal immune response. Microspheres 1 ng—5 microns in diameter leave the Peyer's patch contained within macrophages and migrate to the mesenteric lymph node and to the spleen resulting in a systemic (serum antibody) immune response.

(6) Local or systemic antibody mediated adverse reactions because of preexisting antibody especially cytophyllic or IgE antibody may be minimized or eliminated by using microspheres because of their being phagocytized by macrophages and the antigen is only available as being attached to the cell surface and not free. Only the free antigen could become attached to specific IgE antibody bound to the surface of mast cells resulting in mast cell release of bioactive amines necessary for either local or systemic anaphylaxis.

(7) Immunization with microspheres containing antigen leads to primarily IgA and IgG antibody responses rather than an IgE antibody response, thus preventing subsequent adverse IgE antibody reactions upon reexposure to the antigen.

In addition to the above, the encapsulation of the following synthetic peptides are contemplated and considered to be well within the scope of this invention:
  (1) AF/R1 40–55;
  (2) AF/R1 79–94;
  (3) AF/R1 108–123;
  (4) AF/R1 1–13;
  (5) AF/R1 pepscan 16AA.
  (6) CFA/I 1–13; and
  (7) CF A/I pepscan 16AA.
  (8) Synthetic Pepetides Containing CFA/I Pilus Protein T-cell Epitopes (Starting Sequence # given) 4(Asn-Ile-Thr-Val-Thr-Ala-Ser-Val-Asp-Pro), 8(Thr-Ala-Ser-Val-Asp-Pro-Val-Ile-Asp-Leu), 12(Asp-Pro-Val-Ile-Asp-Leu-Leu-Gln-Ala-Asp), 5(Ile-Asp-Leu-Leu-Gln-Ala-Asp-Gly-Asn-Ala), 20(Ala-Asp-Gly-Asn-Ala-Leu-Pro-Ser-Ala-Val), 26(Pro-Ser-Ala-Val-Lys-Leu-Ala-Tyr-Ser-Pro), 72(Leu-Asn-Ser-Thr-Val-Gln-Met-Pro-Ile-Ser), 78(Met-Pro-Ile-Ser-Val-Ser-Trp-Gly-Gly-Gln), 87(Gln-Val-Leu-Ser-Thr-Thr-Ala-Lys-Glu-Phe), 126(Ala-Gly-Thr-Ala-Pro-Thr-Ala-Gly-Asn-Tyr), and 133(Gly-Asn-Tyr-Ser-Gly-Val-Val-Ser-Leu-Val), and mixtures thereof.
  (9) Synthetic Peptides Containing CFA/I Pilus Protein B-cell (antibody) Eptiopes (Starting Sequence # given) 3(Lys-Ana-Ile-Thr-Val-Thr-Ala-Ser-Val), 11(Val-Asp-Pro-Val-Ile-Asp-Leu-Leu-Gln-Ala-Asp), 22(Gly-Asn-Ala-Leu-Pro-Ser-Ala-Val), 32(Ala-Tyr-Ser-Pro-Ala-Ser-Lys-Thr-Phe-Lys-Thr-Phe-Glu-Ser-Tyr-Arg-Val), 32(Ala-Tyr-Ser-Pro-Ala-Ser-Lys-Thr-Phe), 38(Lys-Thr-Phe-Glu-Ser-Tyr-Arg-Val), 66(Pro-Gln-Leu-Thr-Asp-Val-Leu-Asn-Ser), 93(Ala-Lys-Glu-Phe-Glu-Ala-Ala-Ala), 124 (Lys-Thr-Ala-Gly-Thr-Ala-Pro-Thr), 127(Gly-Thr-Ala-Pro-Thr-Ala-Gly-Asn-Tyr-Ser), and 124(Lys-Thr-Ala-Gly-Thr-Ala-Pro-Thr-Ala-Gly-Asn-Tyr-Ser), and mixtures thereof.
  (10) synthetic peptides containing CFA/I pilus protein T-cell and B-cell (antibody) epitopes (Starting Sequence # given) 3(Lys-Asn-Ile-Thr-Val-Thr-Ala-Ser-Bal-Asp-Pro), 8(Thr-Ala-Ser-Bal-Asp-Pro-Bal-Ile-Asp-Leu-Leu-Gln-Ala-Asp), 11 (Bal-Asp-Pro-Bal-Ile-Asp-Leu-Leu-Gln-Ala-Asp), 20(Ala-Asp-Gly-Asn-Ala-Leu-Pro-Ser-Ala-Val), 124(Lys-Thr-Ala-Gly-Thr-Ala-Pro-Thr-Ala-Gly-Asn-Tyr-Ser), and 126(Ala-Gly-Thr-Ala-Pro-Thr-Ala-Gly-Asn-Tyr-Ser), and mixtures thereof.
  (11) synthetic peptides containing CFA/I pilus protein T-cell and B-cell (antibody) epitopes (Starting Sequence # given)
  CFA/I pilus protein T-cell epitopes
    4(Asn-Ile-Thr-Val-Thr-Ala-Ser-Val-Asp-Pro),
    8(Thr-Ala-Ser-Val-Asp-Pro-Val-Ile-Asp-Leu),
    12(Asp-Pro-Val-Ile-Asp-Leu-Leu-Gln-Ala-Asp),
    15(Ile-Asp-Leu-Leu-Gln-Ala-Asp-Gly-Asn-Ala),
    20(Ala-Asp-Gly-Asn-Ala-Leu-Pro-Ser-Ala-Val),
    26(Pro-Ser-Ala-Val-Lys-Leu-Ala-Tyr-Ser-Pro),
    72(Leu-Asn-Ser-Thr-Val-Gln-Met-Pro-Ile-Ser),
    78(Met-Pro-Ile-Ser-Val-Ser-Trp-Gly-Gly-Gln),
    87(Gln-Val-Leu-Ser-Thr-Thr-Ala-Lys-Glu-Phe),
    126(Ala-Gly-Thr-Ala-Pro-Thr-Ala-Gly-Asn-Tyr),
    and 133(Gly-Asn-Tyr-Ser-Gly-Val-Val-Ser-Leu-Val); and synthetic peptides containing CFA/I pilus protein B-cell (antibody) epitopes (Starting Sequence # given)
  CFA/I pilus protein B-cell epitopes
    3 (Lys-Ana-Ile-Thr-Val-Thr-Ala-Ser-Val), 11 (Val-Asp-Pro-Val-Ile-Asp-Leu-Leu-Gln-Ala-Asp), 22(Gly-Asn-Ala-Leu-Pro-Ser-Ala-Val), 32 (Ala-Tyr-Ser-Pro-Ala-Ser-Lys-Thr-Phe-Lys-Thr-Phe-Glu-Ser-Tyr-Arg-Val), 32 (Ala-Tyr-Ser-Pro-Ala-Ser-Lys-Thr-Phe), 38(Lys-Thr-Phe-Glu-Ser-Tyr-Arg-Val), 66(Pro-Gln-Leu-Thr-Asp-Val-Leu-Asn-Ser), 93(Ala-Lys-Glu-Phe-Glu-Ala-Ala-Ala), 124(Lys-Thr-Ala-Gly-Thr-Ala-Pro-Thr), 127(Gly-Thr-Ala-Pro-Thr-Ala-Gly-Asn-Tyr-Ser), and 124(Lys-Thr-Ala-Gly-Thr-Ala-Pro-Thr-Ala-Gly-Asn-Tyr-Ser), and mixtures thereof.
  (12) synthetic peptides containing CFA/I pilus protein T-cell and B-cell (antibody) epitopes (Starting Sequence # given)
  CFA/I pilus protein T-cell epitopes
    3(Lys-Ana-Ile-Thr-Val-Thr-Ala-Ser-Val), 11 (Val-Asp-Pro-Val-Ile-Asp-Leu-Leu-Gln-Ala-Asp), 22(Gly-Asn-Ala-Leu-Pro-Ser-Ala-Val), 32 (Ala-Tyr-Ser-Pro-Ala-Ser-Lys-Thr-Phe-Lys-Thr-Phe-Glu-Ser-Tyr-Arg-Val), 32(Ala-Tyr-Ser-Pro-Ala-Ser-Lys-Thr-Phe), 38 (Lys-Thr-Phe-Glu-Ser-Tyr-Arg-Val), 66(Pro-Gln-Leu-Thr-Asp-Val-Leu-Asn-Set), 93(Ala-Lys-Glu-Phe-Glu-Ala-Ala-Ala), 124(Lys-Thr-Ala-Gly-Thr-Ala-Pro-Thr), 127(Gly-Thr-Ala-Pro-Thr-Ala-Gly-Asn-Tyr-Ser), and 124(Lys-Thr-Ala-Gly-Thr-Ala-Pro-Thr-Ala-Gly-Asn-Tyr-Ser); and synthetic peptides containing CFA/I pilus protein T-cell and B-cell (antibody) epitopes (Starting Sequence # given)
  CFA/I pilus protein B-cell epitopes
    3(Lys-Asn-Ile-Thr-Val-Thr-Ala-Ser-Bal-Asp-Pro), 8(Thr-Ala-Ser-Bal-Asp-Pro-Bal-Ile-Asp-Leu-Leu-Gln-Ala-Asp), 11 (Bal-Asp-Pro-Bal-Ile-Asp-Leu-Leu-Gln-Ala-Asp), 20(Ala-Asp-Gly-Asn-Ala-Leu-Pro-Ser-Ala-Val), 124(Lys-Thr-Ala-Gly-Thr-Ala- Pro-Thr-Ala-Gly-Asn-Tyr-Ser), and 126(Ala-Gly-Thr-Ala-Pro-Thr-Ala-Gly-Asn-Tyr-Ser), and mixtures thereof.

We contemplate that the peptides can be used in vaccine constructed for systemic administration.

VIII. EXAMPLES

The peptides in (8), (9), and (10) above can be made by classical solution phase synthesis, solid phase synthesis or recombinant DNA technology. These peptides can be incorporated in an oral vaccine to prevent infection by CFA/I beating enteropathogenic *E. coli*.

The herein offered examples provide methods for illustrating, without any implied limitation, the practice of this invention in the prevention of diseases caused by enteropathogenic organisms.

The profile of the representative experiments have been chosen to illustrate the effectiveness of the immunogenic polymeric matrix-antigen composites.

All temperatures not otherwise indicated are in degrees Celcius (°C.) and parts or percentages are given by weight.

IX. MATERIALS AND METHODS

Animals. New Zealand White male rabbits were purchased from Hazelton Research Products (Denver, PA), and were shown to be free of current RDEC-1 infection by culture of rectal swabs. Animals were 1–2 kg of body weight and lacked agglutinating anti-AF/R1 serum antibody at the time of the study.

Antigens. AF/R1 pili from *E. coli* RDEC-1 (015:H:K non-typable) were purified by an ammonium sulfate precipitation method. The final preparation migrated as a single band on SDS-polyacrylamide gel electrophoresis and was shown to be greater than 95% pure by scanning with laser densitometry when stained with coomassie blue. Briefly, equal molar parts of DL-lactide and glycolide were polymerized and then dissolved to incorporate AF/R1 into spherical particles. The microspheres contained 0.62% protein by weight and ranged in size from 1 to 12 micrometers. Both the microencapsulated and non-encapsulated AF/R1 were sterilized by gamma irradiation (0.3 megarads) before use.

Synthetic peptides (16 amino acids each) were selected by theoretical criteria from the amino acid sequence of AF/R1 as deduced from the nucleotide sequence. Three sets of software were used for the selections. Software designed to predict B cell epitopes based on hydrophilicity, flexibility, and other criteria was developed by the University of Wisconsin Genetics Computer Group. Software designed to predict T cell epitopes was based on the Rothbard method was written by Stephen Van Albert (The Walter Reed Army Institute of Research, Washington, D.C.). Software designed to predict T cell epitopes based on the Berzofsky method is published as the AMPHI program. The selected peptides were synthesized by using conventional Merrifield solid phase technology. AF/R1 40–55 (Thr-Asn-Ala-Cly-Thr-Asp-Ile-Gly-Ala-Asn-Lys-Ser-Phe-Thr-Leu-Lys) was chosen as a probable B cell epitope for two reasons: (a) due to its high hydrophilic and flexibility indices, and (b) because it was not predicted to be a T cell epitope by either the Rothbard or Berzofsky method. AF/R1 79–94 (Val-Asn-Gly-Ile-Gly-Asn-Leu-Ser-Gly-Lys-Ala-Ile-Asp-Ala-His-Val) was selected as a probable T cell eptiope because it contained areas predicted as a T cell epitope by both methods and because of its relatively low hydrophilic and flexibility indices. AF/R1 108–123 (Asp-Thr-Asn-Ala-Asp-Lys-Glu-Ile-Lys-Ala-Gly-Gin-Asn-Thr-Val-Asp) was selected as both a T and B cell epitope. AF/R1 40/47/79-86 was produced in continuous synthesis (Thr-Asn-Ala-Cly-Thr-Asp-Ile-Gly-Val-Asn-Gly-Ile-Gly-Asn-Leu-Ser) and represents a hybrid of the first eight amino acids from the predicted B cell epitope and the T cell epitope. The purity of each peptide was confirmed by C-8 reverse phase HPLC, and all peptides were desalted over a Sephadex G-10 Column before use. Using a standard ELISA method, all peptides were assayed for their ability to specifically bind anti-AF/R1 IgG antibody in hyperimmune serum from a rabbit which had received intramuscular injections of AF/R1 pili in Freund adjuvant. Only the peptide chosen as a probable B cell epitope (AF/R1 40–55) was recognized by the hyperimmune serum.

EXAMPLE 1

Immunization. Rabbits were primed twice with 50 micrograms of either microencapsulated or non-encapsulated AF/R1 by endoscopic intraduodenal inoculation seven days apart by the following technique. All animals were fasted overnight and sedated with an intramuscular injection of xylazine (10 mg) and Ketamine HCl (50 mg). An Olympus BF type P10 endoscope was advanced under direct visualization through the esophagus, stomach, and pylorus, and a 2 mm ERCP catheter was inserted through the biopsy channel and threaded 2-3 cm into the small intestine. Inoculums of pili or pili embedded in microspheres were injected through the catheter into the duodenum and the endoscope was withdrawn. Animals were monitored daily for signs of clilnical illness, weight gain, or colonization by RDEC-1.

EXAMPLE 2

Lymphocyte Proliferation. Seven days following the second priming, the rabbits were again sedated with a mixture of xylazine and katamine HCl, and blood was drawn for serum preparation by cardiac puncture. Animals were then euthanized with an overdose of pentothal and tissues including Peyer's patches from the small bowel, MLN, and spleen were removed. Single cell suspension were prepared and washed in Dulbeco's modified Eagle medium (Gibco Laboratories, Grand Island, N.Y.) which had been supplemented with penicillin (100 units/ml), streptomycin (100 micrograms/ml), L-glutamine (2 mM), and HEPES Buffer (10 mM) all obtained from Gibco Laboratories, as well as MEM non-essential amino acid solution (0.1 mM), MEM [50×] amino acids (2%), sodium bicarbonate (0.06%), and $5 \times 10^{-5}$ micrograms 2-ME all obtained from Sigma Chemical Company (St. Louis, Mo.) [cDMEM]. Erythrocytes in the spleen cell suspension were lysed using standard procedures in an ammonium chloride lysing buffer. Cell suspension were adjusted to $5 \times 10^6$ cells per ml in cDMEM, and autologous serum was added to yield a final concentration of 0.5%. Cells (0.1 ml) were placed in 96-well flat bottom culture plates (Costar, Cambridge, Mass.) along with 0.1 ml of various dilutions of antigen and were incubated at 37° C. in 5% $CO_2$. In other experiments, cultures were conducted in a 24-well plates. In these experiments, $5 \times 10^6$ cells were cultured with or without antigen in a 2 ml volume. After 4 days, 100 microliters aliquots of cells were transferred to 96-well plates for pulsing and harvesting. Previous experiments have demonstrated that optimal concentrations of antigen range from 150 ng/ml to 15 micrograms/ml in the 96-well plate assay and 1.5 ng/ml to 150 ng/ml in the 24-well plate assay. These were the concentrations employed in the current study. All cultures were pulsed with 1 Ci [$^3$H]thymidine (25 Ci/mmol, Amersham, Arlington Heights, Ill.) on day 4 of culture and were harvested for scintillation counting 6 hours later.

Statistics. All cultures were conducted in replicates of four, and standard deviations of the counts per minute (cpm) generally range from 5-15% of the average cpm. In experiments where comparison of individual animals and groups of animals is desirable, data is shown as a stimulation index (SI) to facilitate the comparison. SI were calculated by dividing the mean of cultures with antigen by the mean of cultures without antigen (media control). Statistical significance (p value) was determined by comparing the maximum response for each antigen to the media control using the Student's t test.

IX. RESULTS

Lymphocyte proliferation in response to protein and peptide antigens of AF/R1. To determine if lymphoid tissues from AF/R1 immune animals respond in vitro to the antigens of AF/R1, the immunity in a rabbit with preexisting high levels of anti-AF/R1 serum IgG was boosted twice by injection of 50 micrograms of purified AF/R1 pili i.p. seven days apart. A week after the final boost, in vitro lymphocyte proliferation of spleen and MLN cells demonstrated a remarkable response to AF/R1 pili (FIG. 13). In response to the synthetic peptides, there was a small, but significant proliferation of the spleen cells to all the AF/R1 peptides tested as compared to cell cultures without antigen (FIG. 14). Cells from the spleen and Peyer's patches of non-immune animals failed to respond to either AF/R1 or the synthetic peptides.

Microencapsulation of AF/R1 potentiates the mucosal cellular immune response. To evaluate the effect that microencapsulation of AF/R1 may have on the cellular mucosal immune response to that antigen, naive rabbits were primed twice with 50 micrograms of either microencapsulated or non-encapsulated AF/R1 by endoscopic intraduodenal inoculation seven days apart. All rabbits were monitored daily and showed no evidence of clinical illness or colonization by RDEC-1. One week following the last priming, the rabbits were sacrificed and lymphoid tissues were cultured in the presence of AF/R1 pili or peptide antigens. In rabbits which had received non-encapsulated AF/RI, Peyer's Patch cells demonstrated a low level but significant proliferation in vitro in response to AF/R1 pili (FIG. 5), but not to any of the AF/R1 synthetic peptides (FIG. *6a–6d*). However, in rabbits which had received microencapsulated AF/R1, Peyer's Patch cells demonstrated a markedly enhanced response not only to AF/R1 (FIG. 5), but now responded to the AF/R1 synthetic peptides 40–55 and 79–94 (FIG. *6a* and *6b*). In addition, one of two rabbits primed with microencapsulated AF/R1 (rabbit 135) responded to AF/R1 108–123, but not AF/R1 40–47/79–86 (FIG. *6c* and *6d*). In contrast, the other rabbit in the group (rabbit 134) responded to AF/R1 40–47/79–86, but not to AF/R1 108–123 (FIG. *6d* and *6c*).

Response of MLN cells to the antigens of AF/R1. Studies have shown that cells undergoing blastogenesis in the MLN also tend to home into mucosal areas, but experiments requiring in vitro lymphocyte proliferation of rabbit MLN cells are difficult to conduct and to interpret due to non-specific high background cpm in the media controls. Our studies have shown that this problem can be avoided by conducting the proliferative studies in 24-well plates, and then moving aliquots of cells into 96-well plates for pulsing with [$^3$H]thymidine as described in materials and methods. This method of culture was employed for the remainder of the studies. The MLN cells of all rabbits demonstrated a significant proliferation in vitro in response to AF/R1 pili regardless of whether they had been immunized with microencapsulated or non-encapsulated AF/R1· (FIG. 15). However, only the rabbits which had received microencapsulated AF/R1 were able to respond to the AF/R1 synthetic peptide 40–55 (FIG. 11). The MLN cells of rabbit 134 also responded to AF/R1 79–94 ($p<0.0001$), AF/R1 108–123 ($p<0.0001$), and AF/R1 40–47/79–86 ($p=0.0004$); however, none of the other rabbits demonstrated a MLN response to those three peptides (dam not shown).

Response of spleen cells to the antigens of AF/R1. Proliferative responses of spleen cells to AF/R1 were very weak in all animals tested (dam not shown). However, in results which paralleled the responses in MLN cells, there was a significant response to AF/R1 40–55 in rabbits which had been primed with microencapsulated AF/R1 (FIG. 12). There was no response to the other AF/R1 synthetic peptides by spleen cells in either group of animals. The weak response of spleen cells to AF/R1 provides further evidence that these animals were naive to AF/R1 before the study began, and indicates that the observed responses were not due to non-specific stimulative factors such as lipopolysaccharide.

XI, SUMMARY

We have shown that there is an enhanced in vitro proliferative response to both protein and its peptide antigens by rabbit Peyer's patch cells following intraduodenal inoculation of antigen which had been homogeneously dispersed into the polymeric matrix of biodegradable, biocompatible microspheres. The immunopotentiating effect of encapsulating purified AF/R1 pili as a mucosal delivery system may be explained by one or more of the following mechanisms: (a) Microencapsulation may help to protect the antigen from degradation by digestive enzymes in the intestinal lumen. (b) Microencapsulation has been found to effectively enhance the delivery of a high concentration of antigen specifically into the Peyer's patch. (c) Once inside the Peyer's patch, microencapsulation appears to facilitate the rapid phagocytosis of the antigen by macrophages, and the microspheres which are 5–10 micrometers become localized within the Peyer's patch. (d) Microencapsulation of the antigen may improve the efficiency of antigen presenttion by decreasing the amount of enzymatic degradation that takes place inside the macrophage before the epitopes are protected by combining with Class II major histocompatibility complex (MHC) molecules. (e) The slow, controlled-release of antigen may produce a depot effect that mimics the retention of antigen by the follicular dendritic cell. (f) If the antigen of interest is soluble, microencapsulation changes the antigen into a particulate form which appears to assist in producing an IgA B cell response by shifting the cellular immune response towards the $T_H$ and thereby not encouraging a response by the $T_S$. There is evidence that the GALT may be able to discriminate between microbial and non-microbial (food) antigens in part by the form of the antigen when it is first encountered, and thus bacterial antigens do not necessarily have special antigenic characteristics that make them different from food antigens, but they are antigenic because of the bacterial context in which they are presented. The particulate nature of microspheres may serve to mimic that context. It may be important to note that we also observed a significant response to AF/R1 in animals inoculated with non-encapsulated pili; thus, some of this antigen which was still in its native form was able to enter the Peyer's patch. This may be explained by the fact that AF/R1 is known to mediate the attachment of RDEC-1 to the Peyer's patch M-cell. If the antigen employed in this type of study was not able to attach to micrometer M-cells, one would expect to see an even greater difference in the responses of animals which had received microencapsulated versus non-encapsulated antigen.

The microspheres used in these experiments included a size range from 1 to 12 micrometers. The 1 to 5 micrometer particles have been shown to disseminate to the MLN and spleen within migrating macrophages; thus, the observed proliferative responses by cells from the MLN and spleen may reflect priming of MLN or splenic lymphocytes by antigen-presenting/accessory cells which have phagocytosed 1 to 5 micrometer antigen-laden microspheres in the Peyer's patch and then disseminated onto the MLN. Alternatively, these responses may be a result of the normal migration of antigen stimulated lymphocytes that occurs from the Peyer's patch to the MLN and on into the general circulation before homing to mucosal sites. Proliferative responses by MLN cells are of interest because it has been shown that cells undergoing blastogenesis in the MLN tend to migrate onto mucosal areas. However, studies involving in vitro lymphocyte proliferation of rabbit MLN cells can be very difficult to conduct and to interpret due to non-specific high background cpm in the media controls. By simultaneously conducting experiments using different protocols, we have found that this problem can be prevented by avoiding the use of fetal calf serum in the culture and by initially plating the cells in 24-well plates. Using this method, the blasting lymphocytes are easily transferred to a 96-well plate where they receive the [3H]thymidine, while fibroblasts and other adherent cells remain behind and thus do not inflate the background cpm.

The proliferative response to the peptide antigens was of particular interest in these studies. The rabbits that received non-encapsulated AF/R1 failed to respond to any of the peptides tested either at the level of the Peyer's patch, the MLN, or the spleen. In contrast, Peyer's patch cells from the animals that received microencapsulated AF/R1 responded to all the peptides tested with two exceptions: Rabbit 134 did not respond to AF/R1 108-123, and rabbit 135 did not respond to AF/R1 40-47/79-86. The reason for these non-responses is not clear, but it probably is not due to MHC restrictions as evidenced by the fact that rabbit 134 was able to respond to AF/R1 108-123 at the level of the MLN. The non-responses may be due to varing kinetics of sensitized T cell migration in different rabbits, or they may reflect differences in the efficiency of antigen presentation by cells from different lymphoid tissues of these animals. Of all the synthetic peptides tested, only AF/R1 40-55, (the one selected as a probable B cell epitope), was recognized by serum from an AF/R1 hyperimmune rabbit. In addition, this peptide was the only one that was uniformly recognized by Peyer's patch, MLN, and spleen cells from both rabbit. In addition, this peptide was the only one that was uniformly recognized by Peyer's patch, MLN, and spleen cells from both rabbits that were immunized with microencapsulated AF/R1. The recognition by anti-AF/R1 serum antibodies indicates that the amino acid sequence of this peptide includes an immunodominant B cell epitope. Thus AF/R1 40-55 may readily bind to antigen-specific B cells thereby leading to an efficient B cell presentation of this antigen to sensitized T cells. Even though AF/R1 40-55 was not selected as a probable T cell epitope by either the Rothbard or Berzofsky methods, the current study clearly indicates that this peptide can also stimulate a proliferative immune response. Although further studies are required to definitively show that the proliferating cells are indeed T cells, the responses observed in this study are most likely due to the blast transformation of cells from the lineage. Therefore, AF/R1 40-55 appears to contain a T cell epitope in addition to the immunodominant B cell epitope, and this area of the AF/R1 protein may thereby play an important role in the overall immune response and subsequent protection against RDEC-1.

The proliferative responses of spleen cells was low in all animals tested; however, we feel tht this may be simply a matter of the kinetics of cellular migration. The rabbits in this study were sacrificed only two weeks after their first exposure to antigen. This relatively short time period may not have provided sufficient time for cells that were produced by Peyer's patch and MLN blasts to have migrated as far as the spleen in sufficient numbers.

An ideal mucosal vaccine preparation would not only assist in the uptake and presentation of the immunogen of interst, but it would also be effective without requiring carder molecules or adjuvants which may complicate vaccine production or delay regulatory approval. The incorporation of antigen into microspheres appears to provide an ideal mucosal delivery system for oral vaccine immunogens because the observed immunopotentiating effect is achieved without the need for carriers of adjuvants. This ability may prove to be of great value, particularly to enhance the delivery of oral synthetic peptide vaccines to the GALT.

TABLE 1

| Linear B-Cell Epitopes of CFA/I in Monkeys | | |
|---|---|---|
| Sequence Position | Individuals Responding | Consensus Site |
| 1. 11–21 | 3 | VDPVIDLLQ |
| 2. 93–101 | 2 | AKEFEAAA |
| 3. 124–136 | 2 | GPAPT |
| 4. 66–74 | 2 | PQLTDVLN |
| 5. 22–29 | 2 | GNALPSAV |
| 6. 32–40 | 1 | KTF* |
| 7. 38–45 | 1 | |
| 8. 3–11 | 1 | |

*Overlap between epitope 6 and 7

TABLE 2

| Prediction of T cell epitopes within the CFA/I molecule[a] | | |
|---|---|---|
| Predicted Amphipathic Segments | | |
| 7 aa blocks | 11 aa blocks | Rothbard Criteria |
| 22–25 | 8–11 | 16 |
| 34–38 | 32–44 | 30 |
| 40–46 | 51–71 | 38 |
| 50–53 | 86–92 | 44 |

TABLE 2-continued

Prediction of T cell epitopes within the CFA/I molecule[a]

| Predicted Amphipathic Segments | | Rothbard Criteria |
|---|---|---|
| 7 aa blocks | 11 aa blocks | |
| 56–62 | 102–108 | 57 |
| 64–71 | 130–131 | 61 |
| 104–108 | 135–137 | 70 |
| 131–137 | | 116 |
| | | 124 |
| | | 127 |
| | | 137 |

[a]The sequence numbers of the first amino acid of the predicted T cell epitopes are shown. Software designed to predict T cell epitopes based on the Berzofsky method was published as the AMPHI program. It predicts amphipathic amino acid segments by evaluating 7 or 11 residues as a block and assigning a score to the middle residue of that block. Software designed to predict T cell epitopes based on the Rothbard method was written by Stephen Van Albert (The Walter Reed Army Institute of Research, Washington, D.C.).

TABLE 3

Amino acid sequence of immunodominant T cell epitopes[a]

| Residue Numbers | Amino Acids |
|---|---|
| 8–17 | Thr Ala Ser Val Asp Pro Val Ile Asp Leu |
| 40–49 | Phe Glu Ser Tyr Arg Val Met Thr Gln Val |
| 72–81 | Leu Asn Ser Thr Val Gln Met Pro Ile Ser |
| 134–143 | Asn Tyr Ser Gly Val Val Ser Leu Val Met |

[a]Of the 19 decapeptides that supported a significant proliferative response and contained a serine at either position 2, 3, or 4, nine has a serine specifically at position 3. Some of the most robust responses were to the peptides that contained a serine residue at the third position. The amino acid sequence of four such decapeptides which are believed to be immunodominant T cell epitopes is shown.

DEMONSTRATIVE EVIDENCE OF PROTECTIVE IMMUNITY

RDEC-1 is an eteroadherent diarrhea producing *E. Coli* in rabbit. Its attachment to the mucosa is by the adhesin (AF/R1 pili). The adhesin is an excellent vaccine candidate. It may intitiate a mucosal response but is susceptiple to digestion in the gut. The incorporation of AF/R 1 into biocompabible, nondigestible microspheres enhanced mucosal cellular immune respones to RDEC-1. We have demonstrated that immunization with AF/R1 Pili in microspheres protect rabbits against infection with RDEC-1.

Six rabbits received intra-duodenal immunization of AF/R1 microspheres (0.62% coreloading by weight) at 200 ug AF/R1 on day 0 then boosted with 100 ug AF/R1 in microspheres on days 7, 14, and 21 followed RDEC-1 challenge with $10^8$ organisms one week latter than observed for 1 week and then sacrificed, unimmunized rabbits were challenged with $10^8$ RDEC-1 only and observed 1 week than sacrified. Also, 2 rabbits were immunized only then were sacrificed 10 days latter. Only one of these animals had bile IgA antibodies to AF/R1. but both had specific sensitized T cells which released IL-4 upon challenge in the spleen, Peyer's patch and illeal lamina propria. All nine immunized animals developed diarrhea and weight loss which was significant at the $p<0.001$ level compared to the immunized animals which displayed no diarrhea and no weight loss. The immunized animals colonized the intestinal tract with RDEC-1 the same as the unimmunized animals. However, there was a striking difference regarding the adherence of RDEC-1 to the mucosa. No adherence was seen in cecum in the immunized animals compared to 4/7 in the unimmunized side animals. This difference was significant to the $p<0.01$ level. The RDEC-1 exposure although not producing disease in the immunized animals did effect a booster immunization as relected in the increase in anti-AF/R1 antibody containing cells in the muscosa similiar to the immunized rabbits. This study clearly demonstrated complete protection against RDEC-1 infection and strongly indicates similiar results should be expected with entertoxigenicity *E. coli* using the Colony Forming Antigens (CFA's) in microsphere vaccines.

SUMMARY STATEMENT OF PROTECTIVE IMMUNITY SHOWINGS

Figure 26:
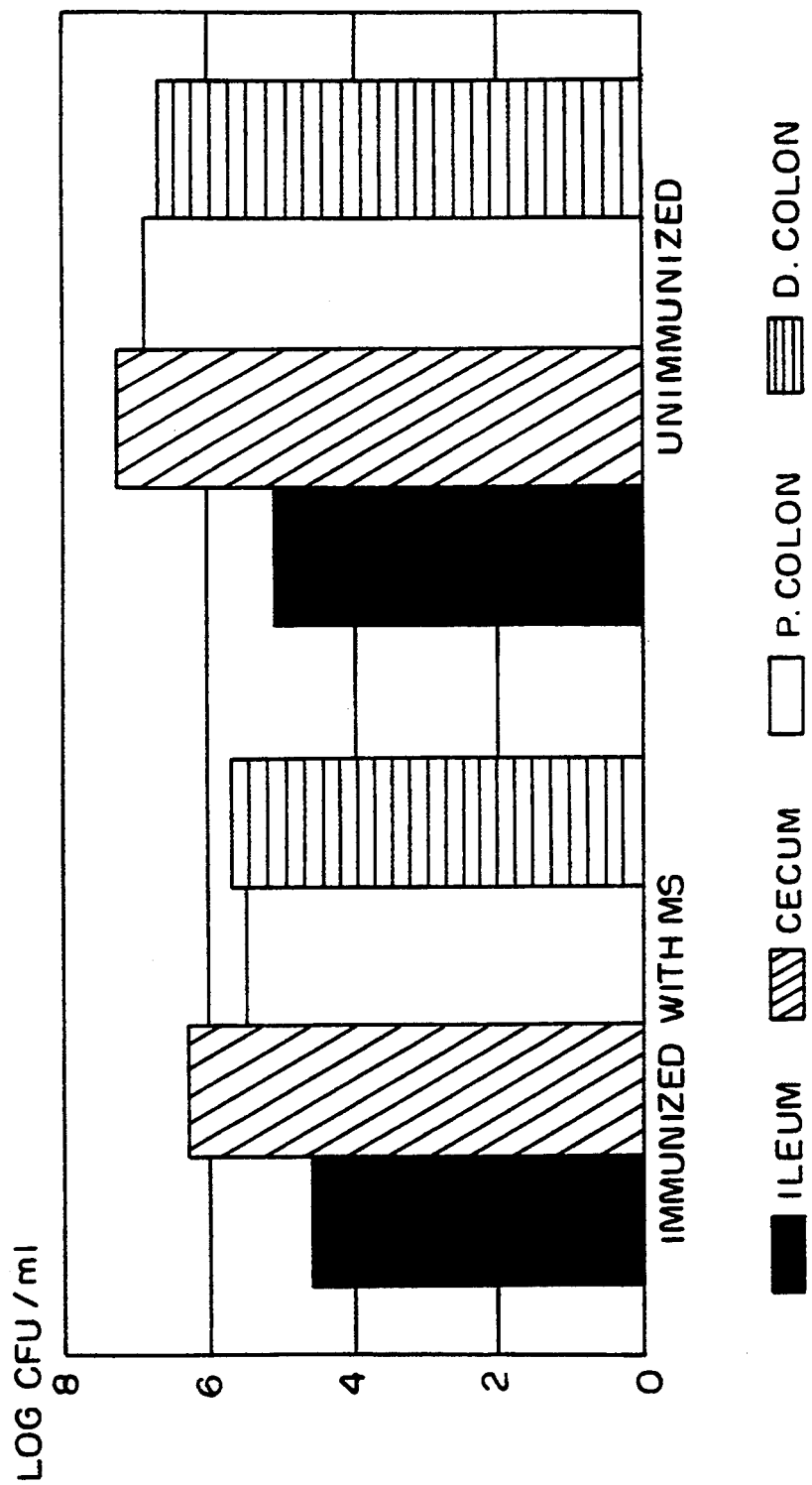
FIG. 26 shows that RDEC-1 colonization (log CFU/gm) in cecal fluids was similar in both groups (mean 6.3 vs 7.3; p=0.09).
Figure 27:
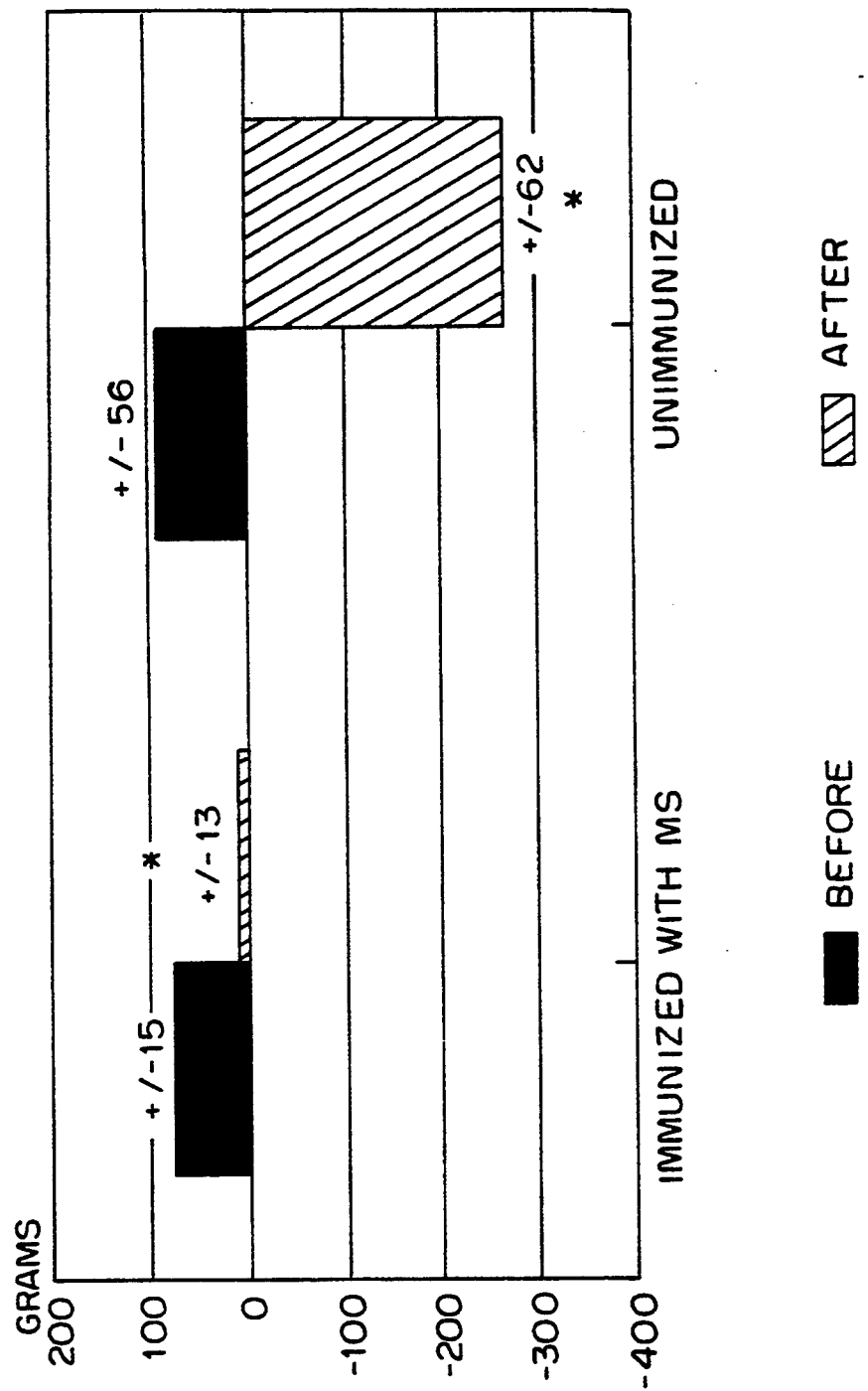
FIG. 27 shows that rabbits given AF/R1-MS remained well and 4/6 gained weight after challenge, whereas 9/9 unvaccinated rabbits lost weight after challenge (mean weight change +10 vs −270 grams p<0.001).
Figure 28:
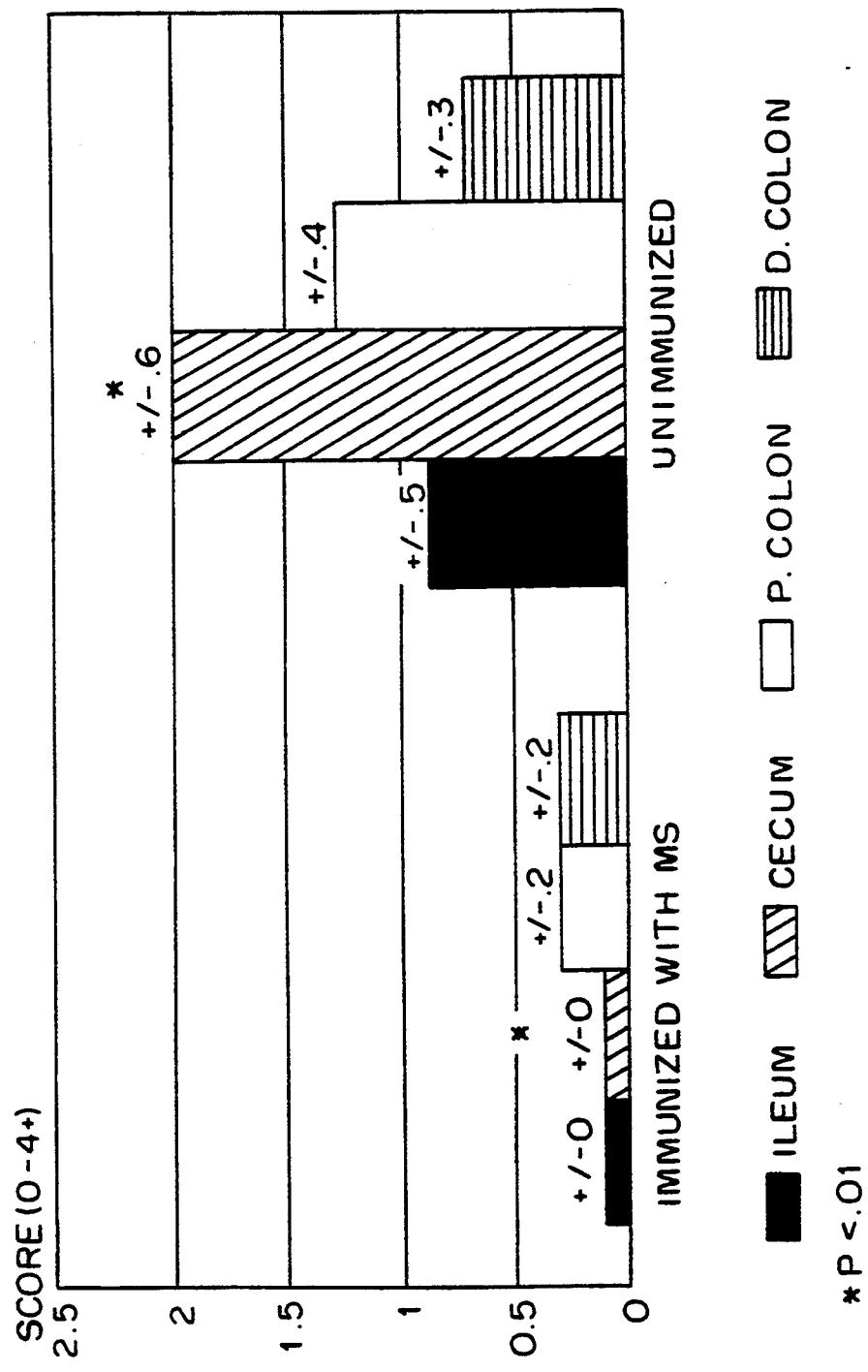
FIG. 28 shows that the mean score of RDEC-1 attachment to the cecal epithelium was zero in vaccinated, and 2+ in unvaccinated animals.

RDEC-1 infection of rabbits causes an enteroadherent *E. coli* diarrheal disease, and provides a model for the study of adherence-factor immunity. Pilus adhesions are vaccine candidates, but purified pili are subject to intestinal degradation. Previously we showed potentiation of the mucosal cellular immune response to the AF/R1 pilus of RDEC-1 by incorporation into biodegradable polylactide-coglycolide microspheres (AF/R1-MS). We now present efficacy testing of this vaccine. Six rabbits were primed with 200 ug and boosted with 100 ug of AF/R1-MS weekly ×3, then challenged at week 5 with $10^8$ CFU of RDEC-1 expressing AF/R1. Nine unvaccinated rabbits were also challenged. Two rabbits vaccinated with AF/R1-MS were sacrificed at week 5, without challenge, for measurement of anti-AF/R1 antibodies in bile (by ELISA) and anti-AF/R1 containing cells (ACC) in the intestinal lamina propria Coy immunohistochemistry). Attachment of RDEC-1 to intestinal epithelial cells was estimated (0.4+) by immunoperoxidase staining of histologic sections. Colonization of intestinal fluid was measured by culture of intestinal flushes. Results: Rabbits given AF/R1-MS remained well and 4/6 gained weight after challenge, whereas 9/9 unvaccinated rabbits lost weight after challenge (mean weight change +10 vs −270 gins $p<0.001$), (see FIG. 27). The mean score of RDEC-1 attachment to the cecal epithelium was 0 in vaccinated, and 2+ in unvaccinated animals (see FIG. 28). RDEC-1 colonizaiton (log CFU/gm) in cecal fluids was similar in both groups (mean 6.3 vs 7.3; $p=0.09$) (see FIG. 26). ACC were not seen in the lamina propria of vaccinated but unchallenged animals, but anti-pilus IgA antibody levels in bile were increased 1 S.D. over negative controls in 1 animal. Conclusions: Vaccination with AF/R1-MS was safe and protected rabbits against RDEC-1 disease. Protection was associated with interference with RDEC-1 adherence to the mucosal surface, but lumenal colonization was not prevented.

More recently, applicants have focused on areas of this invention related to an immunostimulating composition comprising encapsulating microspheres, which may contain a pharmaceutically-acceptable adjuvant, wherein said microspheres are comprised of (a) a biodegradable-biocompatible poly (DL-lactide-co-glycolide) as the bulk matrix, wherein the relative ratio between the amount of lactide and glycolide components are within the range of 52:48 to 0:100 and (b) an immunogenic substance comprising Colony Factor Antigen (CFA/II, hepatitis B surface antigen (HBsAg), or a physiologically similar antigen that serves to elicit the production of antibodies in mammalian subjects.

These areas of invention are referred to herein after as Phase II and Phase III, respectively, and are summarized as follows:

1. An immunostimulating composition comprising encapsulating-microspheres, which may contain a pharmaceutically-acceptable adjuvant, wherein said microspheres having a diameter between 1 nanometers (nm)

to 10 microns (um) are comprised of (a) a biodegradable-biocompatible poly (DL-lactide-co-glycolide) as the bulk matrix, wherein the relative ratio between the amount of lactide: and glycolide components are within the range of 52:48 to 0:100 and (b) an immunogenic substance comprising Colonization Factor Antigen, hepatitis B surface antigen (HBsAg), or a physiologically similar antigen that serves to elicit the production of antibodies in mammalian subjects.

2. An immunostimulating composition according to paragraph 1 wherein the amount of said immunogenic substance is within the range of 0.1 to 1.5% based on the volume of said bulk matrix.

3. An immunostimulating composition according to paragraph 2 wherein the relative ratio between the lactide and glycolide component is within the range of 48:52 to 52:48.

4. An immunostimulating composition according to paragraph 2 wherein the size of more than 50% of said microspheres is between 5 to 10 um in diameter by volume.

5. A vaccine comprising an immunostimulating composition of paragraph 4 and a sterile, pharmaceutically-acceptable carrier therefor.

6. A vaccine comprising an immunostimulating composition of paragraph 5 wherein said immunogenic substance is Colony Factor Antigen (CFA/II).

7. A vaccine comprising an immunostimulating composition of paragraph 5 wherein said immunogenic substance is hepatitis B surface antigen (HBsAg).

8. A method for the vaccination against bacterial infection comprising administering to a human, an antibactericidally effective amount of a composition of paragraph 6.

9. A method according to paragraph 7 wherein the bacterial infection is caused by a bacteria selected from the group consisting essentially of *Salmonella typhi, Shigella sonnei, Shigella flexneri, Shigella dysenteriae, Shigella boydii, Escheria coli, Vibrio cholera, yersinia, staphylococus, clostridium,* and *campylobacter.*

10. A method for the vaccination against viral infection comprising administering to a human an antivirally effective amount of a composition of paragraph 7.

11. A diagnostic assay for bacterial infections comprising a composition of paragraph 4.

12. A method of preparing an immunotherapeutic agent against infections caused by a bacteria comprising the step of immunizing a plasma donor with a vaccine according to paragraph 6 such that a hyperimmune globulin is produced which contains antibodies directed against the bacteria.

13. A method preparing an immunotherapeutic agent against infections caused by a virus comprising the step of immunizing a plasma donor with a vaccine according to paragraph 7 such that hyperimmune globulin is produced which contains antibodies directed against the hepatitis B virus.

14. An immunotherapy method comprising the step of administering to a subject an immunostimulatory amount of hyperimmune globulin prepared according to paragraph 12.

15. An immunotherapy method comprising the step of administering to a subject an immunostimulatory amount of hyperimmune globulin prepared according to paragraph 13.

16. A method for the protection against infection of a mammal (human or nonhuman animal) by enteropathogenic organisms or hepatitis B virus comprising administering to said mammal an immunogenic amount of an immunostimulating composition of paragraph 3.

17. A method according to paragraph 16 wherein the immunostimulating composition is administered orally.

18. A method according to paragraph 16 wherein the immunostimulating composition is administered parenterally.

PHASE II

In sum, the Colony Factor Antigen (CFA/II) from enterotoxigenic *E coli* (ETEC) prepared under GMP was successfully incorporated into biodegradable polymer microspheres (CFA/II BPM) under GMP and found to be safe and immunogenic when administered intra-duodenally to rabbits. CFA/II was incorporated into poly (D,L-lactide-co-glycolide) (PLGA) microspheres which were administered by direct endoscopy into the duodenum. Following vaccination, Peyer's patchcells responded by lymphocyte proliferation to in vitro challenge with CFA/II indicating the CFA/II BPM to be immunogenic when administered intra-intestinally. Also, B cells secreting specific anti CFA/II antibodies were found in spleens following vaccination. No pathological changes were found following total necropsies of 10 rabbits vaccinated with CFA/II BPM. As a potency test, high serum IgG antibody titers to CFA/II were produced following intra- muscular administration of CFA/II BPM to additional rabbits. The CFA/II BPM contained 63% between 5–10 um by volume particle size distribution; 1.17% protein content; 2.15% moisture; <0.01% acetonitrile; 1.6% heptane; 22 nonpathogenic bacteria and 3 fungi per 1 mgm protein dose; and passed the general safety test. We conclude that the CFA/II BPM oral vaccine is immunogenic and safe to begin a Phase I clinical safety study following IND approval.

INTRODUCTION

Enterotoxigenic *Escherichia coli* (ETEC) causes diarrheal disease with an estimated 650,000,000 cases anually in developing countries resulting in 500,000 deaths predominantly in the pediatric age groups. Currently there is no vaccine against ETEC induced diarrhea. The availability of an effective oral vaccine would be of great value to the people of South America, Africa and and Asia as well as the millions of people who travel to these high risk areas and account for half of the annual cases.

The first step in pathogenesis is adherence to the small intestine epithelial cells by protein fimbrial (pilus) adhesins called colonization factor antigen (CFA). Three major CFAs have been recognized, CFA/I, CFA/II and CFA/IV. (25)

Ten human volunteers who were immunized orally twice weekly for 4 weeks with CFA/II developed a poor antibody response and did not show any significant protection when challenged with pathogenic ETEC (26). This disappointing response was attributed to adverse effects of gastric acid, even at neutral pH, of fimbrial proteins (27). When the vaccine was administered by inoculation directly into the duodenum, 4 of 5 immunized volunteers developed a significant rise in secretory IgA with CFA/II antibody (26).

D and L-lactic acid and glycolic acid, as homo- and copolymers, are biodegradable and permit slow and continued release of antigen with a resultant adjuvant activity. These polymers have been shown to be safe in a variety of applications in human beings and in animals (28–32). Delivery of antigens via microspheres composed of biodegradable, biocompatible lactide/glycolide polymers (29–32) may enhance the mucosal response be protecting the antigen from digestion and targeting them to lymphoid cells in Peyer's patches (29–32). McQueen et al. (33) have shown that *E. coli* AF/R1 pili in PLGA microspheres, introduced intraduodenally in rabbits, protected them against diarrhea and weight loss when challenged with the parent strain rabbit diarrheagenic strain of *E. coli* (RDEC-1). Only one vaccinated rabbit of six lost weight and only one had soft pelleted stool. In contrast, all control unvaccinated animals became ill, lost weight, and shed soft pellets or unformed mucoid stool. Significant lymphocyte proliferation to AF/R1 from Peyer's patches and ordinary IgA anti AF/R1 antibody levels were seen.

In order to improve the CFA/II vaccine it was incorporated into PLGA microspheres under GMP in order to protect it from digestion and target it to the intestinal lymphoid system. The CFA/II BPM vaccine has undergone pre-clinical evaluation and has been found to be safe and immunogenic.

MATERIALS AND METHODS

Preparation of CFA/II Pilus Vaccine

Under Good Laboratory and Good Manufacturing Practices, *E. coli*, strain M424C1-06;816 producing CFA/II were cultured in 75–80 CFA agar plates (24×24 cm) for 24 hrs then harvested by scraping. The harvest was homogenized at slow speed for 30 minutes with over head drive unit and cup immersed in an ice bath. The homogenate was centrifuge at 4° C. at 16,500× g for 30 minutes. The supernatant saved and the pellet rehomogenized and centrifuged with the supernatants pooled. The supernatant pool was centrifuged at 50,000× g for 45 minutes. The supernatant treated with ammonium sulfate at 20% satuaration, stirred 30 minutes at 4° C. than stored at 4° C. for 16 hrs then centrifuged at 19,700× g for 30 minutes. The supernatant saved and treated with ammonium sulfate at 45% saturation, stirred 30 minutes at 4° C., stored at 4° C. for 66–72 hrs, then centrifuged at 19,700× g for 45 minutes. The pellet was resuspended in about 100 mls of PBS containing 0.5% formalin and held at 22° for 18 hrs then dialyzed for 45–50 hrs against PBS at 4° C. using a total of 12 liters in 2 liter amounts. The dialysis was terminated when the PBS contained less then 0.03% formalin using Nessler's reagent and fuchsin sulfuose acid reagent. The final product contained 1 mgm protein/ml PBS, was sterile and passed the general safety test.

Preparation of Desalted CFA/II Vaccine

Two ml of the CFA/II vaccine were placed into a Centricon 30 tube and centrifuged at 1700 rpm at 4°–6° C. (Beckman model GPR centrifuge equipped with GA-24fixed angle rotor) until all the buffer solution passed through the filter (about 90–120 minutes). Sterile water was added to each tube to disperse the CFA/II retained on the filter. The desalted antigen dispersions from all tube were pooled and then divided into five equal parts by weight so as to contain 20 mg of the CFA/II each. The desalted antigen dispersion was stored at −10° to −20° C.

Freeze Drying of the Desalted CFA/II Dispersion 80 mg of sucrose was added to each part of the CFA-/II dispersion. The resulting mixture was flash-frozen using a dry ice-acetone bath (100–150 ml od acetone and 50–100 g of dry ice). The frozen solution was freeze dried overnight using Repp Sublimator 16 freeze dryer at vacuum of 1 micrometer of mercury and a shelf temperature not exceeding 37° C.

CFA/II Biodegradable Polymer Microspheres
Particle Size Distribution

About 1 mgm of microspheres were dispersed in 2 ml of 1% Polysorbate 60° (Ruger Chemical Co. Inc. Irvington, N.J.) in water in a 5 ml capacity glass vial by sonication. This dispersion was observed under a calibrated optical microscope with 43× magification. Using a precalibrated eye-piece micrometer, the diameter of 150 randomly chosen microspheres, was determined and the microsphere size distribution was determined Scanning Electron Microscopic Analysis Microspheres were sprinkled or the surface of 10 mm stub covered with a non-conductive adhesive (Sticky-Tab, Ernest F. Fullem, Inc., Lutham, N.Y.) Samples were coated with gold/palladium in an automatic sputter-coating opparatus (Samsputter-2A, Tonsimis Research Corporation). The samples were examined with a Hitachi S-450 scanning electron microscope operated at 15–20 KV.

Preparation Of CFA/II Microspheres

Solvent extraction techique was used to encapsulate the freeze dried CFA/II into poly(lactide-co-glycolide)(Medisorb Techologies International, visocity 0.73 dl/g) microspheres in the 1–10 um size range to achieve theoretical antigen loading of 1% by weight. The freeze dried antigen-sugar & matrix was dispersed in an acetolnitrile solution of the polymer and then emulsified to achieve desired droplet size. Microspheres were solidified and recovered by using heptane as extracting solvent. The microsphere batches were pooled and vacuum dried to remove traces of solvent.

Protein Content The CFA/II microspheres were dissolved in 0.9% SDS in 0.1N NaOH for 18 hr with stirring then neutralized to pH 7 and assayed. The micro bicichoninic acid (BCA) method was utilized with both lactic acid and glycolic acid blanks and compared to bovine serum albumin (BSA) standard and results expressed as percent by weight.

Moisture Content

One hundred and fifty mgm of CFA/II microspheres were dissolved in 3 ml of acetonitrile by sonication for 3 hours. One ml sample was injected into a Karl Ficher titrimeter and triter reading observed was recorded and acetonitrile blank was substracted to determined percent water content.

Acetonitrile and Heptane Residuals

Ten mgm of CFA II microspheres were dissolved in 1 ml DMF then analysed using gas chromatography and comparing peak heights to external standards of either acetonrile or heptane diluted in DMF with 10 mgm of blank microspheres. The results are expressed as percent by weight.

Microbial Load

One hundred mgm of CFA/II microsphere(single dose) are suspended in 2 ml of sterile saline than poured into 2 blood agar plates (1 ml each). All colonies are counted and identified after 48 hours in culture at 37° C. and expressed as total number. Similiar amount of microspheres is in 0.25 ml aliquots poured onto 4 different fungal culture plates (Sabhiragar, casein peptone agar with chloramphenicol, brain heart infusion agar with chloramphenol and genimycin or chloramphenicol alone) and cultured at 30° for 5 weeks and the colonies counted & identified and expressed as total number.

CFA/II Release From Microsphere Study

Thirty mgm samples in triplicate were placed in 2 ml conical upright microcentrifuge tubes containing 1 ml of PBS at pH 7.4. The tubes were capped and kept immerized in a water bath maintained at 37° C. with constant agitation. The samples were withdrawn at 1, 3, 6, 8, 15 and 22 hour time intervals by centrifuging the sample tubes for 5 minutes at the maximum speed of bench top centrifuge. The release medium was collected through a 5 um nylor screen for CFA/II protein analysis using the micro BCA method and comparing results to BSA standard and expressing results as percent cumulative release of CFA/II.

General Safety Test

Two doses of one hundred mgm CFA/II microspheres were suspended by sonication for 5 minutes in 3.1 mls of sterile vaccine dilutent consisting of injectable saline containing 0.5% Polysorbate 60 ® N.F., 0.03 ml were injected intraperitoneally into each of 2 mice and 3 mls were administered by gastric lavage to each of 2 guinea pigs. The animals were weighed both before and at 7 days following the vaccine administration. All animals were observed daily for any signs of toxicity.

Rabbits 1.5–2 kilogram male specific pathogen free New Zealand white rabbits, obtained from closed colony maintained at the National Institute of Health, Bethesda, Md. They were selected for study if they did not have measurable serum antibodies at 1:2 dilution to CFA/II antigens by ELISA and were not colonized by *E. coil* as determined by culture of rectal swabs.

Intra-Muscular Immunization of Rabbits and ELISA

Two Rabbits were immunized with CFA/II microsphere vaccine at 25 ug protein in two different sites intra-muscularly on day 0. Sera were obtained from all animals before immunization on day o and days 7 and 14. The sera were tested by ELISA for IgG antibodies to CFA/II antigen and individual coli surface (CS) proteins CS3 and CS 1. ELISA plates were coated with 3 ug/ml of either CFA/II antigen, CS3 or CS1 protein (150 ul/well) and incubated with 150 ul/well of PBS with 0.1% BSA for four hours at room temperature. The PBS with 0.1% BSA is washed out with PBS and 100 ul/well of different dilutions of each rabbit serum in triplicate was added to the plates. The dilutions ranged from undiluted to 1:1,000,00. The plates were incubated with the sera for 3 hours at 37° C. The sera were washed out with PBS and then horse radish peroxidase-conjugated goat anti- rabbit IgG was added to the plates at a 1:1000 dilution (100 ul/well). The plates were incubated for 1 hour at room temperature with the peroxidase conjugate. The conjugates were washed out of the plates with PBS and 100 ul/well of an ABTS substrate solution (Kikegaard and Perry Laboratories) was added to each well in the plates. The plates were read using the ELISA reader(Dynatech Laboratories MR 580) at a wave length of 405 nm after 15 minutes. The results are measured and expressed as antibody titers.

Intra-duodenal Vaccination of Rabbits

Rabbits (N=5) were vaccinated with CFA/II microspheres containing either 25 or 50 ug of protein suspended in 1 ml of PBS containing 0.5% Polysorbate 60 ® on day 0 and 7 by sonication. The microspheres were injected through an Olympus BF type P10 bronchoscope into the duodenum of the rabbits following sedation with an intra muscular injection of ketamine HCl (50 mgm I.M.)(Ketaset, Fort Dodge Laboratories, Fort Dodge, Iowa) and Lylazine (10 mgm I.M.) (Rompom Malay Corporation, Shnanee, Kans.). The endoscope was advanced ready under direct vission into the stomach which was insufflated with a 50 ml bolus of room air via a catheter passed through the biospy channel. The catheter was advanced through the pylorus 3–4 cm into the duodemum and the microsphere suspension in 1 ml of PBS was injected, followed by a 9 ml flush of PBS and removal of the air bolus. The rabbits were scarified by chemical euthanasia at day 14.

Anti-CFA/II Stimulated Lymphocyted Transformation

The Peyer's Patchs were removed and cell suspension obtained by teasing and irigation with a 20 guage needle and syringe. The cells were placed in 2 ml of media at a concentration of $2.5\times10^6$ cells/ml for each well of a 24 well plate. These cells were challenged separately with BSA and the CFA/II antigen at doses of 500, 50 and 5 ng/ml in triplicate wells. The plates were incubated at 37° C. with 5% $CO_2$. On day 4 the cells were mixed while still inside the wells and 100 ul were transferred into each of 4 wells in a 96 well flat bottom microculture plate. Thus, the challenge at each antigen dose represented by 3 wells in the 24 well plate is now represented by 12 wells in the 96 well plate. After the cells have been transferred, each well is pulsed with 20 ul of 50 uCi/ml tritiated thymidine. These pulsed plates were incubated for 6 hrs then harvester with 96 Mach II Cell harvested (Tourtec, Inc.). The lymphocyte proliferation was determined by the tritriated thymidine incoporation measured in kilo counts per minute (Kcpm) using the 1205 Beta Plate Liquid scintillation counter (LKB, Wallac, Inc.). The results are expressed as mean Kcpm±SD and compared to media controls.

Anti-CFA/II Antibody Secreting B Cells

Spleen cells were obtained from immunized rabbits on day 14 following intra-duodenal immunization with CFA/II microsphere vaccine. The cells were placed in 96 well round bottom microculture plate at a final concentration of $6\times10^5$ cells/well and incubated for 0, 1, 2, 3, 4 and 5 days at 37° C. with 5 $CO_2$. 96 well flat bottom microculture plates were coated with 3 ug/ml of CFA-/II antigen overnight blocked with PBS with 0.05% Polysorbate 60 ®. On the harvest days, the cells were gently flushed out of the wells of the round bottom plates and transferred to the corresponding well in the antigen coated, 96 well flat bottom microculture plates to be tested for the presence of antibody secreting cells using ELISPOT technique. The plates were incubated with the cells overnight at 4° C. The cells were then washed out of the flat bottom plates with PBS, and 100 ul/well of horserudish-peroxidase conjugated, goat anti-rabbit total antibody (IgM, IgG, and IgA) at a 1:1000 dilution were added to the plates. The Plates were incubated for 1 hour at room temperature, at which time, the conjugate was washed out of the plates with PBS. 0.1 mgm of agarose was dissolved in 10 ml of PBS by boiling. After the agar solution cooled but not hardened, 6 mgm of 4-chloro-naphthol, 2 mls of methanol and 30 ul of hydrogen peroxide were added to make the substrate solution. The solution was placed into the flat bottom plates (100 ul/well) and the plates were held at 4° C. overnight so the agar could harden. The number of browish spots per 15 wells (total of $9\times10^6$ spleen cells) was counted and represents the number of antibody secreting cells per $9\times10^6$ spleen cells.

Pathological Evaluation

Rabbits were euthanized by parenteral overdose of sodium pentobarbital and were subjected to complete necropsy. Sample of tissue including small and large intestine with gut associated lymphoid tissue, spleen, mesenteric and mediastinal lymph nodes, lung, trachea, liver and kidney were fixed by immersion in 10% neutral buffered formalin. Tissues were routinely processed for light microscopy and embedded in paraffin. Five micron thick sections were stained with hematoxylin and eosin.

Statistical Analysis

The paired student t-test was used to determine p values.

RESULTS

Particle Size Distribution

The results of size frequency analysis of 150 randomly chosen microspheres are shown in (FIG. 29). The particle size distribution is plotted in % frequency against particle size in diameter (size) expressed in um. The average number fregency diameter is 4.6 um. The average volume frequency diameter is 4.6 um. The percent volume between diameters of 5–10 um is 63% and the percent volume less than 10 um diameter is 88%.

Scanning Electoron Microscopy

The microspheres are seen in (FIG. 30) which is a scanning electron photomicrograph. Nearly all the microspheres are less than 10 um as compared to the 5 um bar. Also the surfaces of the microsphere are smooth and demonstrate lack of pores.

Protein Content

The protein loads of the individual batches are the following: K62A8, 1.16%±0.10 SD; K63A8, 1.023%±0.17SD; K64A8, 1.232%±0.13 SD; and K65A8, 0.966%±0.128 SD. The mean average protein load is 1.16%±0.15 SD. The protein load of the CFA/II microsphere vaccine in the final dose vial is the following: Lot L74F2, 1.175%±0.17SD.

Moisture Content

The CFA/II microsphere vaccine (Lot 74F2) percent water content was found using the Karl Fischer titrimeter method to be 2.154% using triplicate samples.

Acetonitrile and Heptane Residuals

The acetonitrile residuals of the 4 individual CFA/II microsphere batches are the following: K62A8, <0.1%; K62A8, <0.1%, K64A8, <0.1%; and K65A8, <0.1%. The acetonitrile residual of the CFA/II microsphere vaccine in the final dose vial is the following: Lot L74F2, 0.07±0.05%. The heptane residual of the 4 individual CFA/II microsphere batches are the following:K62A8, 1.9%; K63A8, 1.4%; K64A8, 1.6% and K65A8, 1.6%. Following pooling in heptane and subsequent drying, the heptane residual of the CFA/II microsphere vaccine in the final dose vial is the following: Lot L74F2, 1.6±0.1%.

Microbial Load

One hundred milligrams (a single dose) of CFA/II microsphere vaccine (Lot L74F2) in the final dose vial was suspended in a 2 ml of sterile saline and 1 ml poured onto a blood agar culture plate ×2. Twenty two colonies grew after 48 hours of culture and 21 were identified as coagulase negative staphlycoccus and 1 as a micrococus species. All these bacteria are considered to be nonpathogenic to humans. An additional 100 mgms of CFA/II microsphere vaccine (Lot L74F2) were suspended in 2 ml of sterile saline and 0.25 ml poured onto four different fungal culture agars and cultered for 5 weeks. Three fungal colonies grew and each was identified as *A. glaucus*.

CFA Release From Microsphere Study

Three thirty mgm samples were incubated each in 1 ml of PBS, pH 7.4 at 37° C. for 0, 1, 3, 6, 8, 15 and 22 hours. The superanates were removed and replaced at these times. The protein content was determined for each supernate sample and the results are seen in (FIG. #31). The results are plotted as percent release of CFA/II against time in hours. An average of 8% of CFA/II is released at one hour rising to 20% at 8 hours then a slower release to 25% at 22 hours.

General Safety Test

Two one hundred milligrams(a single dose) of CFA/II microsphere vaccine in the final dose vials were suspended in 3.1 mls of the sterile diluent consisting of 0.85N saline prepared for injection plus Polysorbrate 60 ® at 0.5%. Two Swiss mice (16.5 gm) were injected intraperitoneally with 0.03 mls and two Hartley guinea pigs (350 gm) were administered by gastric lavage 3.0 mls.

None of these animals displayed any signs of toxicity for 7 days. The mice gained and average of 2.3 gms and the guinea pigs gained and average, of 43 grams. The CFA/II microsphere vacccine therefore passed the general safety test.

Serum IgG Antibody Responses

Two rabbits were immunized in two separate sites intra-muscularly with 25 ug of protein of CFA/II microsphere vaccine (Lot L74F2) in the final dose vial. Sera samples were obtained before and 7 and 14 days following immunization. The IgG antibody titers to CFA/II CSI and CS3 protein were determined using ELISA and the results seen in (FIG. 32). The results are expressed as mean antibody titers against the different antigens at 0, 7 and 14 days. High antibody titers greater than 1000 were seen at 7 days to both CS1 and CS3 protein which rose to greater than 10,000 by day 14. The individuals titers to CFA/II are seen in (FIG. 33). Rabbit 109 developed an antibody titer of 1,000 by day 7 rising to 3,000 by day 14. Rabbit 108 had a log higher rise at day 7 and 2 log higher rise at day 14 being $3 \times 10^4$ at day 7 going to $1 \times 10^5$ at day 14.

Anti-CFA/II Stimulated Lymphocyte Transformation

Five rabbits were immunized intra-duodenally with CFA/II microspheres containing either 25 ug of protein (human dose equivalent) or 50 ug of protein on days 0 and 7 and then sacrificied on day 14. The Peyer's patch lymphocytes were challenged in vitro with CFA/II antigen, BSA media and alone. The lymphocyte transformation was determined by tritriated thymidine incorporation. The results of the high dose immunization are seen in (FIG. 34). The results are expressed as Kcpm against antigen dose. No response to BSA or media control is seen in any of the five rabbits. All rabbits responded by lymphocyte transformation in a dose dependent manner to the CFA/II.

The highest dose responses were 3–10X's the media control are highly significant with a p value of <0.002. The results of the 5 rabbits receiving the low dose immunization are seen in (FIGS. 35). Rabbit #80 gave no response probably due to poor Peyer's patch cell population which did not respond were to Conconavallin A mitogenic stimulation either. The remaining 4 rabbits gave positive responses with the high CFA/II dose response being 2–8x media control and highly significant with p values of <0.009. Again no response were seen to BSA compared to the media controls.

Anti-CFA/II Antibody Secreting B-Cells

Five rabbits immunized intraduodenally with CFA/II microsphere containing 50 ug of CFA/II protein at days 0, 7 than scarified at day 14 were studied. The spleen cells were placed into microculture then ELISPOT forming B-Cells secreting specific anti CFA/II antibody determined at days 0, 1, 2, 3, 4 and 5. The results are seen in (FIG. 36) and expressed as # of antibody secreting cells per $9 \times 10^6$ spleen cell against culture days. Positive responses were seen in all 5 rabbits on days 2-5. Days of maximum responses occurred on day 3 for rabbits 65 and 66; day 4 for rabbit 85; amd day 5 for rabbits 83 and 86. The responses are highly significant being 7-115 times higher than the 1-2 cells seen on all days in 4 control rabbit (67, 69, 72, 89) (FIG. 37). Here is a composite graph expressing the mean counts$\pm$1SD for all days of culture.

Pathological Evaluation

A consistent finding in the spleens of all rabbits both the 25 and 50 ug protein dose groups was minimal to mild diffuse lymphocytic hyperplasia the periarteriolar lymphatic sheaths (T cell dependent areas). Two of five rabbits of the 50 ug dose group (#83 and #86) also had mild lymphocytic hyperplasia of splenic follicular (B cell dependent) areas. The three rabbits in an untreated control group had histologically normal spleens.

Reactive hyperplasia of mesenteric lymph nodes was often seen in vaccinated rabbits. Two of five rabbits in the 25 ug dose equivalent group (#83 and #86) also had minimal to mild lymphocytic hyperplasia of cortical follicular (B cell dependent) areas. The mesenteric lymph nodes of the other vaccinated rabbits and of the untreated control rabbits were within normal limits. Incidental or background lesions found in one or more rabbits of all three group were acute minimal to mild pnuemonia and foreign body microgranulomas of the cecal gut associated lymphoid tissue.

Disscussion

McQueen et al (33)has found that the AF/R1 adhesin of rabbit diarrheagenic *Escheria coli* (RDEC-1) incorporated into biodegrable microspheres could function as a safe and effective oral intestinal vaccine in the rabbit diarrhea model. The AF/R1 was incorporated into poly D,L-lactide-co-glycolide) microspheres and administered intraduodenally. Jarboe et al (34) reported that Peyer's patch cells obtained from rabbits immunized intra-duodenually with AF/R1 in microspheres responded with lymphocte proliferation upon in vitro challenge with AF/R1. This early response at 14 days gave a clear indication as to the immunogenicity of *E. coli* pili contained within the polymer microspheres.

In developing an effective oral vaccine against enterotoxigenic *E. coli*, CFA/II pili given as an oral vaccine was found to be ineffective. The CFA/II pilus proteins were found to be rapidly degraded when treated with 0.1 mHCl and pepsin conditions mimicking those contained in the stomach (27). The CFA/II was found to be immunogenic when given in high doses intraintestinally producing intestinal secretary IgA antibodies (26).

The CFA/II vaccine has now been incorporated into Poly(D,L lactide-co-glycolide) microspheres under Good Manufacturing Practices and tested under Good Laboratory Practices. The microspheres, are spherical, smooth surfaced and without pores. The majority (63% ) are between 5-10 um in diameter by volume. This size range has been suggested to promote localization within the Peyer's patch in mice and perhaps enhance local immunization (29-32). The protein content being 1.174% is close to 1% which was the goal of the vaccine formulation. One percent was chosen because 0.62% was the core loading of the AF/R1 microspheres which were effective. Also a small precentage perhaps 1-5% (35) is anticipated to be taken up from the intestine, a higher protein content would lead to considerable loss of protein.

The organic residuals are of course a concern. Heptane exposure would be 1.7 mgm per vaccine dose. This is compared to the occupational maximum allowable exposure of 1800 mgm/15 min. Therefore, the heptane contained with the CFA/II microsphere vaccine appears to be a safe level. The acetonitrile-is very low —0.1 mgm per vaccine dose. The human oral TDLO is 570 mgm/Kg (any non lethal toxicity). Therefore, the acetonitrile contained with the CFA/II microsphere vaccine appears to be at a safe level. The CFA/II vaccine was produced under sterile conditions. However, the process of incorporation of the desalted CFA/II vaccine into the polymer microsphere batches and subsequent pooling and loading final dose vials was done in a clean room as for any oral medication. It was expected and found that there was be a microbial load. The guide used was the World Health Organization (WHO) Requirements of Thyphoid Vaccine (Live Atttaruated, Ty 21 a oral). Two hundred non pathogenic bacteria are allowed as well as 20 fungi per dose. The CFA/II microsphere vaccine is well under these requirements having only 22 non-pathogenic bacteria and 3 fungi per dose.

The general safety test was also patterned after the WHO requiremets for the TY, 21a oral vaccine in that the CFA/II microsphere vaccine was give by gastric lavage to the guinea pigs. Both mice and both guinea pigs demonstrated no toxicity & gained weight over the 7 day test clearly indiciating the innoccuos nature of this vaccine by passing this safety test.

The CFA/II microsphere vaccine (Lot74F2) is immunogenic giving high titer serum IgG antibody responses as early as 7 days following intra muscular injection in rabbits. This test will be used as potency test for future lots of the CFA/II microsphere vaccine. Slighly higher antibody titers were seen towards the CS3 pilus protein and this may reflect that CS3 accounts for 90% of the protein in the CFA/II and CS1 10% (36).

The CFA/II microsphere vaccine was also immunogenic following intra-duodenal administration to rabbits. The highest lymphocyte proliferative responses from Peyer's patch cells were seen with the lower 25 ug dose. This is the human equivalent dose and suggests that higher doses of antigen in polymer microspheres may attenuate, this immunological reponse.

The antibody secreting B-cells demonstrated in the rabbit spleen at 14 days is a clear indication that B-cells have been immunized. They may represent resident B-cells immunized in the spleen or B-cells immunized at the level of the Peyer's patches and are migrating through the spleen to return to the intestinal mucosal lamina propria (1-3). The delay of several days before secreted antibody is detected suggests either manuration is required of the B-cells or that down regulation may be present initially and lost with time in culture.

Further evidence of immunization by the CFA/II microsphere vaccine given intra-duodenually is demonstrated by the lymphatic hyperplasia in the spleen seen to a greater extend in the rabbits receiving the lower dose 5/5 compared to 2/5 of the rabbits receiving the higher 50 ug protein dose. On the other hand, greater T-cell dependent area lymphoytic hyperplasia in the mesenteric lymph nodes were seen in rabbits receiving the higher 50 ug dose, 4/5 compared to 2/5. These changes are most likely due to the vaccine since similar changes were not seen in three untreated control rabbits. Also no abnormal pathological changes attributable to the vaccine were seen. The CFA/II BPM vaccine has undergone pre-clinical evaluation and has been found safe and immunogenic. This vaccine is ready for clinical Phase I safety testing following FDA's IND approval.

PHASE III

In sum, alum precipitation, vaccination regimen and controlled delivery by microencapsulation were studied to determine what criteria must be satisfied to provide a protective immune response to hepatitis B surface antigen (HBsAg) after a single injection of vaccine. In mouse studies, the 50% effective dose ($ED_{50}$) for the alum precipitated Heptavax B vaccine (Merck, Sharp and Dohme) was 3.8 ng when administered in a 3 injection regimen, but was 130 ng when one immunizing dose was used. Antigen release studies revealed that HBsAg is bound tightly to the alum, indicating that the antigen remains in situ until scavenged by phagocytic cells. the $ED_{50}$ with a 3 dose regimen of aqueous HBsAg was 180 ng, a opposed to over 2000 ng for daily injections of low doses for 90 days and 240 ng for a regimen that employed initially high doses that decreased geometrically at 3 day intervals over 90 days. The $ED_{50}$ was 220 ng for a single dose regimen of HBsAg microencapsulated in poly (DL-lactide-co-glycolide) in a form that was too large to be phagocytized and had an antigen release profile similar to that achieved with the geometrically decreasing regimen of doses. This indicates that single injection of microencapsulated immunogens can achieve similar effects in vivo to those achieved with multiple dose regimens. For HBsAg the effect to be achieved appears to be 3 pulses of particulate immunogens that can be scavenged by phagocytes.

INTRODUCTION

A major disadvantage of inactivated vaccines lies in their inability to confer lasting immunity. Due to rapid elimination from the body, multiple doses and boosters are usually required for continued protection[37]. Alum adjuvants, achieving their effects by mechanisms of antigen presentation and sustained antigen release[38], have been used successfully to increase the potency of several inactivated vaccines including those against tetanus, anthrax, and serum hepatitis[39,40]. Though useful, alum preparations are deficient in several aspects. Control over quantity and rate of antigen release is limited, often resulting in a continued requirement for immunization schedules consisting of multiple injections given over a period of several months to years. Alum adjuvants are also non-biodegradable and thus remain within the body, serving as a nidus for scar tissue formation[38] long after they have served their function.

Protracted, multiple immunization schedules are unacceptable during massive mobilization and deployment of troops. Changing global disease patterns and deployment of new biological warfare agents by enemy forces require flexibility in the number and types of vaccine antigen administered to soldiers departing for combat. Any immunization schedule requiring completion during engagement in non-linear combat would compromise this flexibility and place an unreasonable burden on our health care delivery system.

The main objective of this study was, therefore, to develop a biodegradable, controlled-release adjuvant system capable of eliminating the need for multistep vaccination schedules. This investigation was designed to: (1) determine in an animal model hepatitis B vaccine release rate characteristics desirable for single-step immunization, (2) incorporate those release rate characteristics into a one-step biodegradable poly(DL-lactide-co-glycolide)(DL-PLG) microencapsulated hepatitis B surface antigen (HBsAg) vaccine, and (3) conduct an in vivo trial comparing the effectiveness of this single-step vaccine against the conventional three-step hepatitis vaccine currently employed[41]. The results were intended to provide the foundation for further development of single step vaccines against hepatitis and other militarily significant diseases[42].

MATERIALS AND METHODS

Vaccine potency assay. Due to its availability, compatibility with cage mates, and potential application to the study of hepatitis B vaccine[43], the female Walter Reed (ICR) stain mouse was used. A hepatitis B vaccine potency assay for comparing the six-month immunization schedule currently in use[41] with that of a single-step immunization by sustained antigen release was established according to the following protocol: Specimens for baseline antibody titers were collected from twenty mice by exsanguination. Immediately prior to exsanguination, all mice employed in this and other exsanguination procedures in these studies were anesthetized with a 0.1 ml injection of V-Pento. Groups of 12 mice were then immunized according to a schedule consisting of either 0.25 ug, 0.025 ug, 2.5 ng, 0.25 ng, 2.5 pg, or 0.25 pg Heptavax B vaccine (HBV) administered in 50 microliter volumes subcutaneously (s.c.) at the beginning and end of the first, and end of the second month of the protocol. Antibody responses to the vaccine were monitored immediately before the third injection and approximately one month after the third injection. Specimens for antibody determination were collected by exsanguination of seven anesthetized mice from each group and assayed along with the baseline samples by the Abbott Ausab radioimmunoassay. Percent seroconversion verses micrograms vaccine employed with calculated by the method of Reed and Muench[43]. These data were employed to establish a mouse vaccine potency assay calibrated to detect differences between Heptavax B and other forms of hepatitis b vaccine.

In Vitro Antigen Release Rate from Heptavax B vaccine

Antigen release from aluminum hydroxide adjuvant in HBV was measured by pumping 2 cc per hour of 1:20,000 thimerosal in saline at 4° c across a 0.2 u pore diameter Acrodisc filter apparatus containing 20 ug of vaccine. The effluent, collected by a Gilford fraction collector, was assayed periodically over several weeks for protein by UV absorption at 280 nm on a Beckman model 25 double beam spectrophotometer, and for HBsAg by the Abbot Ausria II radioimmunoassay made quantitative by using HBsAg standards supplied by Merk, Sharp, and Dohme. Accuracy of the HBsAg standards were verified by Biuret protein determination and by UV absorbance at 215 nm and 225 nm[44]. Non-specific antigen retention on the Acrodisc filter was assessed by measuring percent recovery of a known quantity of HBsAg. Spontaneous degradation of vaccine antigen was monitored by comparing daily rations of antigen to total protein detected in the effluent.

Evaluation of HBsAg Stability

These studies were designed to characterize the stability of the aqueous antigen to the various physical conditions employed in the microencapsulation process. Conditions tested included lyophilization with reconstitution in distilled water, cyclohexane, methylene chloride, chloroform, methyl alcohol, acetone, iso-octane, hexane, acetone, pentane, or heptane; irradiation while lyophilized; and, exposure to elevated temperatures. Samples exposed to organic solvents were first lyophilized, reconstituted with the test solvent, evaporated to dryness under nitrogen at room temperature and reconstituted with distilled water. Test samples were compared against untreated controls by assaying serial dilutions of each with the Abbot Ausria II procedure and comparing the plots of counts per minute verses dilution.

Assessment of the Effect of Antigen Release Rate on Vaccine Potency

Three regimens simulating patterns of free HBsAg release that could be achieved by microencapsulation were contrasted with the three monthly dose regimen of Heptavax B for immunizing mice. To do so, 24 ICR mice were divided into groups and vaccinated as indicated below. Seven mice from each subgroup were exsanguinated at the end of the second and third months of the experiment. The sera were separated and assayed for specific antibody response to HBsAg by Abbot Ausab procedure.

HV regimen a: 14 mice/treatment receiving 3 s.c. injections of 250, 25, 2.5 or 0.25 ng doses of HBV a month apart.

HBsAg regimen a: 14 mice/treatment receiving 3 s.c. injections of 250, 25, 2.5 or 0.25 ng doses of aqueous HBsAg a month apart.

HBsAg regimen b: 14 mice/treatment receiving total doses of 750, 75, 7.5 or 0.75 ng of aqueous HBsAg over 3 months by s.c. injections of $ZX_Y$ng at 3 day intervals, where Z is the total dose, y is the injection number, and X is the fraction indicated on the graph in FIG. 1 minus the fraction for the previous injection.

HBsAg regimen c: 14 mice/treatment receiving daily s.c. injections of 8.33, 0.833, 0.0833 or 0.00833 ng of aqueous HBsAg for 3 months.

Microencapsulation in DL-PLG

Microencapsulated immunogens were fabricated by Southern Research Institute, Birmingham, Ala. DL-PLG polymers were synthesized from the cyclic diesters, DL lactide and glycolide, by using a ring-opening melt polymerization catalyzed by tetraphenyl tin[45]. The resulting polymer was dissolved i methylene chloride, filtered free of insoluble contaminants and precipitated in methanol. Lactide-co-glycolide mole ration of the product was determined by nuclear magnetic resonance spectroscopy. Encapsulation of HBsAg in DL:PLG polymer was achieved by an organic phase separation process[46]. Microcapsules of the desired size (approximately 100 micron diameter in these studies) were isolated from each batch by wet sieving with hexane through standard mesh stainless steel sieves and then dried for 24 hours in a vacuum chamber maintained at room temperature.

In Vitro Analysis of Encapsulated Antigens

Integrity of encapsulated antigen was assessed by comparing the antigen to total protein ratios present in microcapsule hydrolysates with those obtained from suspensions of pure unencapsulated antigen. Centrifuge tubes containing 1 ug of either microencapsulated or pure vaccine antigen in 1 ml saline were incubated at 4° c with shaking. Samples were collected at weekly intervals by interrupting the incubation, sedimenting the contents of the tubes by centrifugation and withdrawing the supernates. Sediments were resuspended in 200 microliters of saline and supernates were assayed for HBsAg by the Abbott Ausria II radioimmunoassay. The HBsAg standard described earlier in this report was used as the calibrator. Antigen destruction due to the encapsulation procedure was monitored by a comparison between the antigen assayed from the hydrolysate and from the untreated antigen control.

Assessment of the potency of DL:PLG microencapsulated HBsAg for immunizing ICR mice when used alone and in combination with Heptavax B vaccine. HBsAg loaded microcapsules that had been fabricated by Southern Research Institute to release the majority of their HBsAg load within 40 to 50 days were serially diluted in 10-fold steps by mixing the dry, loaded capsules with blank placebo capsules of similar size and composition. The resulting stock and diluted microcapsule preparations were placed onto lyophilizer when not in use in order to assure minimum spontaneous degradation prior to injection. On the day of injection, a predetermined weight of microcapsules or placebo-diluted microcapsules was added to each syringe. Immediately prior to injection either one or two ml of injection vehicle (2 wt % carboxymethyl cellulose and 1 wt & Tween 240 in water, Southern Research Institute) were drawn into the microcapsule-loaded syringes, mixed and injected. All mice were vaccinated s.c. as indicated below:

Group 1: 14 mice/treatment receiving 25, 25, 2.5, 0.25 or 0.925 ng HBV.

Group 2: 14 mice/treatment receiving 1000, 250, 25 or 2.5 ng aqueous HBsAg with Bovine Serum Albumin (BSA).

Group 3: 7 mice receiving 1600 ng microencapsulated HBsAg (HBsAg) plus 0.25 ng HBV and 14 mice/treatment receiving 160, 16, 1.6 or 0.16 ng HBsAg plus 0.25 ng HBV.

Group 4: 7 mice receiving 1600 ng HBsAg plus 2.5 ng HBV and 14 mice/treatment receiving 160, 16, 1.6 or 0.16 ng HBsAg plus 2.5 ng HBV.

Group 5. : 7 mice receiving 1600 ng HBsAg plus 25 ng HBV and 14 mice/treatment receiving 160, 16, 1.6 or 0.16 ng HBsAg plus 25 ng NBV.

Group 6 :7 mice receiving 2500 ng HBsAg and 14 mice-treatment receiving 250, 25, 2.5 or 0.25 ng HBsAg. Fifty-three days after receiving the above injections, the mice were anesthetized with an 0.1 cc injection of V-Pento and exsanguinated. Blood samples were allowed clot and the sera were separated by centrifugation. The serum samples were assayed for antibody to HBsAg by the Abbott Ausab procedure.

RESULTS

Heptavax B vaccine potency. As can be seen from Table 4, the total dose of vaccine which produced seroconversion in 50% of

TABLE 4

Potency of Heptavax B vaccine in ICR mice.

| No. Inj. | ng Heptavax B per Injection | | | | | | | $ED_{50}$ ng |
|---|---|---|---|---|---|---|---|---|
| | 250 | 25 | 2.5 | .25 | .025 | .0025 | .00025 | |
| 2 | 5/5 | 4/4 | 3/6 | 2/6 | 0/5 | 1/4 | 0/4 | 1.7 |
| 3 | 6/6 | 6/6 | 4/6 | 1/6 | 0/6 | 1/6 | 1/6 | 2/0 |

*Number positive seroconversions per number vaccinated.

The vaccinated mice ($ED_{50}$) for HBV was approximately 2 ng, whether the vaccine was given in 2 or 3 injections.

In vitro antigen release rate from HBV. HBsAg release from the 20 ug of Heptavax was not detected in any of the 21 fractions of saline collected from the Acrodisc polycarbonate filter over a 30 day period. The lower limit of detection for the Abbott Auria II assay employed was approximately 4.8 ng/ml. The Acrodisc filter used in the antigen release study was back-washed with 10 mls normal saline. Quantitation of the HBsAg present within this back-wash eluent revealed the presence of the original 40 ug of Heptavax vaccine which had been loaded into the filter at the start of the experiment. This is the concentration which one would expect to obtain if there had been no deterioration of the original 40 ug/ml HBsAg loaded onto the filter, none of the antigen eluted from the alum adjuvant, and none of the vaccine had adsorbed onto or passed through the filter.

Evaluation of antigen stability. Considerable effort was expended in assessing the effects of physical conditions on the antigenicity of HBsAg to insure that the conditions used for microencapsulation would not cause serious degradation of the immunogen. Since microencapsulation must be performed on dried materials which are suspended in organic solvents, the HBsAg, which was provided as a solution, had to be lyophilized. Initial attempts at lyophilizing HBsAg in normal saline resulted in a total loss of detectable antigen within samples. Dilution of the HBsAg sample 1:10 in distilled water prior to freezing resulted in reservation of nearly 100% of the antigen detectable in the original sample. Studies of antigen stability at elevated temperature revealed that HBsAg may be heated to 50° C. for up to one hour without appreciable loss of antigen. The studies involving exposure of lyophilized antigen to organic solvents indicated that iso-cane and hexane had minimal effects on antigenicity, but that 95% to 100% of antigenicity was lost upon exposure to either methylene chloride, chloroform, cyclohexane, or methyl alcohol. Moderate antigen loss occurred in the presence of acetone, pentane and heptane. As a result of these studies, hexane was chosen as the solvent for microencapsulation.

Assessment of the effect of antigen release rate on vaccine potency. The results (Table 5) indicated that immunogen formation (i.e., the alum adjuvant of Heptavax B) had far more

TABLE 5

| Effect of immunogen formulation and vaccination regimen on potency for immunizing ICR mice. | | | | | | |
|---|---|---|---|---|---|---|
| Immunogen | | ng Total Dose HBsAg | | | | $ED_{50}$ |
| Formulation | Regiment | 750 | 75 | 7.5 | .75 | ng |
| Heptavax B | a | 7/7* | 6/6 | 5/7 | 1/7 | 3.8 |
| Aqu. HBsAg | a | 4/6 | 3/7 | 0/7 | 0/6 | 180 |
| Aqu. HBsAg | b | 6/7 | 0/7 | 1/7 | 0/7 | 240 |
| Aqu. HBsAg | c | 1/7 | 0/7 | 0/7 | 0/7 | >2000 |

*Number positive seroconversions per number vaccinated.
a 3 injections of 1/3 total dose a month apart.
b Injections administered every three days for 90 days in decreasing dosages according to a logarithmic progression.
c Injections of 1/90 total dose daily for 90 days.

effect on potency than did the vaccination regimen, and that pulsing with large doses of immunogen was more effective than continuous administration of small doses.

HBsAg release from DL:PLG microcapsules. The microcapsules employed in this study were designed to disintegrate within three weeks after hydration. It is evident from the release curve (FIG. 2) that they performed as designed, releasing approximately 17% of their total load in an initial pulse and approximately 7% of the remaining available HBsAg over the first three weeks.

Assessment of the potency of DL:PLG microencapsulated HBsAg for immunizing ICR mice when used alone and in combination with Heptavax B vaccine. The results (Table 6) indicate that the microencapsulated HBsAg had approximately the same immunogenicity as did the Heptavax B. Neither immunogens were sufficiently potent to effect with a singly injection seroconversion rates similar to those achieved after three injections of Heptavax B (Table 4). Only the immunogen

TABLE 6

| Potencies of Heptavax B and microencapsulated HBsAg by single injection S.C. when administered alone and in combination to immunize ICR mice. | | | | | | | | |
|---|---|---|---|---|---|---|---|---|
| Var. Dose ng | Const. | ng Variable Dose | | | | | Var. Dose | Tot. Dose |
| Immunogen | Dose mHBsAg | 2500 | 250 | 25 | 2.5 | .25 | $ED_{50}$ ng | $ED_{50}$ ng |
| Heptavax B | 0 | 13/14* | 8/14 | 4/14 | 0/13 | | 130 | 130 |
| Heptavax B | 0.16 | | 11/13 | 4/14 | 1/14 | | 1.7 | 1.8 |
| Heptavax B | 1.6 | | 10/13 | 1/14 | 0/13 | | 100 | 100 |
| Heptavax B | 16 | | 3/14 | 1/14 | 1/14 | | >470 | >490 |
| Heptavax B | 160 | | 3/12 | 2/11 | 1/12 | | >370 | >530 |
| Heptavax B | 1600 | | 7/7 | 7/7 | 7/7 | | <0.8 | 1600 |
| Mic. HBsAg | 0 | 3/6 | 6/15 | 1/13 | 2/10 | 2/14 | 220 | 220 |

*Number positive seroconversions per number vaccinated.

combination of Heptavax B with 0.16 ng mHGsAg provided this level of seroconversion. At the $ED_{50}$ endpoint, the 0.16 ng dose of mHGsAg is approximately 10% of the total dose. Similarly, a small amount of Heptavax B appeared to enhance the immunogenicity of the microencapsulated immunogen, although the combination was clearly less immunogenic when the two formulations were present at equivalent concentrations.

DISCUSSION

The potential advantage of microcapsules lies in their ability to be programmed during fabrication into forms that have quite difference release profiles, including slow and steady release, multiple bursts of antigen over a period of time, or combinations of release forms. Sieving allows choice of microcapsule size, and the ability of DL-PLG to sequester antigen from the host's immune system until release occurs enhances control over exposure of the recipient's immune system to antigen over a sustained period of time. These characteristics provided the impetus for these studies as they indicate potential for achieving the effects of a multiple injection regimen by controlling release in vivo after a single injection.

The results of these studies are important for gaining an under standing of the fundamental differences between the manner in which alum and microcapsules interact with the immune system. The antigen release studies showed that alum firmly bound the antigen on its surface, whereas the microcapsules sequestered the antigen load within the interstices of an immunologically inert polymer. Release of antigen from microcapsules was spontaneous and gradual while antigen release from alum wa probably enzymatically mediated within host macrophages. Alum thus performed at least two useful functions as an adjuvant: by beating its entire load of antigen upon its surface, it provided a large single exposure of antigen to the host; and, by being readily phagocytized by host macrophages, it served as a means of targeting the antigen to the immune system.

In order for microcapsules to be efficacious as a vaccine delivery system, a means of incorporating the two properties common to alum adjuvant must be devised. These properties, which where discussed above, are targeting antigen to the immune system and delivering the antigen load in a single concentrated pulse at its target. A gradual, sustained release of free antigen, as was achieved with the 100 micron microcapsules used in these studies, could be expected to elicit an immune response similar to that seen with either regimen b or regimen c (Table 5), where multiple injections of small doses were employed. In fact, as shown in Table 3, the microencapsulated immunogen elicited a response similar to that achieved with regimen b. This is probably due to the fact that the microcapsules release approximately 10% of their antigenic load immediately after injection.

Microcapsules with extended release patterns tend to be large (>10 microns in diameter) and thus fail to be readily phagocytized. In order for the larger microcapsules with prolonged antigen release characteristics to be efficacious, the antigen eventually released from those microcapsules would have be in a form which targeted and concentrated it within the recipient's immune system. This might be effectively achieved by microencapsulation of antigen coated alum or by microencapsulating clusters of smaller (<10 microns) microcapsules.

Microcapsules under 10 microns in diameter tend to be readily phagocytized and also tend to under go rapid spontaneous degradation due to their high surface to volume ratio. These smaller microcapsules would be well suited for eliciting a primary response if their pulse of antigen release could be programmed to occur after phagocytosis.

LITERATURE CITED

1. Mooi, F. R., and F. K. de Graaf. 1985. Molecular biology of fimbriae of enterotoxigenic *Escherichia coli*. Curr. Top. Microbiol. Immunol. 118:119–138.

2. Evans, D. G., D. J. Jr. Evans, S. Clegg, and J. A. Pauley. 1979. Purification and characterization of the CFA/I antigen of enterotoxigenic *Escherichia coli*. Infect. Immun. 25:738–748.

3. Evans, D. G., D. J. Jr. Evans, W. S. Tjoa, and H. L. Dupont. 1978. Detection and characterization of colonization factor enterotoxigenic *Escherichia coli*. isolated from adults with diarrhea. Infect. Immun. 19:727–736.

4. McConnell, M. M., H. Chart, and B. Rowe. 1989. Antigenic hornology within human enterotoxigenic *Escherichia coli* fimbrial colonization factor antigens-CFA/I, coli-surface- associated antigens (Cs)1, Cs2, Cs4, and Cs17, FEMS Micro. Lett. 61: 105–108.

5. Cheney, C. P., and E. C. Boedeker. 1983. Adherence of an enterotoxigenic *Escherichia coli* strain, serotype 078:H11, to purified human intestinal brush borders. Infect. Immun. 39:1280–1284.

6. Miles, M. A., G. R. Wallace, and J. L. Clarke. 1989. Multiple peptide synthesis (Pepscan method) for the systematic analysis of B- and T-cell epitopes: application to parasite proteins. Parasitology Today 5:397–400.

7. Rothbard, J. B., and W. R. Taylor. 1988. A sequence pattern common to T cell epitopes. EMBO. J. 7:93–100.

8. DeLisi, C., and J. A. Berzofsky. 1985. T-cell antigenic sites tend to be amphipathic structures. Proc. Natl. Acad. Sci, USA 82:7048–7052.

9. Margalit, H., J. L. Spounge, J. L. Cornette, K. B. Cease, C. DeLisi, and J. A. Berzofsky. 1987. Prediction of Immunodominant helper T cell antigenic sites from the primary sequence. J. Immunol. 138:2213–2229.

10. Berzofsky, J. A. 1988. Structural basis of antigen recognition by T lymphocytes. J. Clin. Invest. 82:1811–1817.

11. Stille, C. J., L. J. Thomas, V. E. Reyes, and R. E. Humphreys. 1987. Hydrophobic strip-of-helix algorithm for selection of T cell-presented peptides. Mol. Immunol. 24:1021–1027.

12. Lozzi, L., M. Rustici, M. Corti, M. G. Cusi, P. E. Valensin, L. Bracci, A. Santucci, P. Soldani, A. Spreafico, and P. Neri. 1990. Structure of rebella E1 glycoprotein epitopes established by multiple peptide synthesis. Arch. Virol. 110:271–276.

13. Troalen, F., A. Razafindratsita, A. Puisieux, T. Voeltzel, C. Bohuon, D. Bellet, and J. M. Bidart. 1990. Structural probing of human lutropin using antibodies raised against synthetic peptides constructed by classical and multiple antigen pepetide system approaches. Mol. Immunol. 27:363–368.

14. Tan, X. H., M. Ratnam, S. M. Huang, P. L. Smith, and J. H. Freisheim. 1990. Mapping the antigenic epitopes of human dihydrofolate reductase by systematic synthesis of peptides on solid supports. J. Biol. Chem. 265:8022–8026.

15. Van der Zee, R., W. Van Eden, R. H. Meloen, A. Noordzij, and J. Van Embden. 1989. Efficient mapping and characterization of a T cell epitope by the simultaneous synthesis of multiple peptides. Eur. J. Immunol. 19:43–47.

16. Geysen, H. M., R. H. Meloen, and S. J. Barteling. 1984. Use of peptide synthesis to probe viral antigens for epitopes to a solution of a single amino acid. Proc. Natl. Acad. Sci. USA 81:3998–4002.

17. Isaacson, R. E. 1977. K99 surface antigen of *Escerichia coli*: Purification and partial characterization. Infect. Immun. 15:272–279.

18. Klemm, P. 1982. Primary structure of the CFA1 fimbrial protein from human enterotoxigenic *Escherichia coli* strains. Eur. 124:339–348.

19. Devereux, J., P. Haeberli, and O. Smithies. 1984. A comprehensive set of sequence analysis programs for the VAX. Nucleic Acids Res. 12:387-395.

20. Hall, R. H., D. J. Maneval, J. H. Collins, J. L. Theibert and M. M. Levine. (1989). Purification and analysis of colonization factor antigen I, coli surface antigen 1, and coli surface antigen 3 fimbriae from enterotoxigenic *Escherichia coli.* J. Bacteriol. 171, 6372-4.

21. Karjalainen, T. K., D. G. Evans, M. So and C. H. Lee. (1989). Molecurlar cloning and nucleotide sequence of the colonization factor antigen I gene of *Escherichia coli.* Infect Immun. 57, 1126-30.

22. Kraitzen, H. D., J. Wiltfang, M. Karas, V. Neuhoff, and N. Hilschmann. (1989) Gas-phase sequencing after.electroblotting on polyvinylidene difluoride membranes assigns correct molecular weights to myoglobin molecular weight markers. . Anal. Biochem. 183, 1-8.

23. Matsiduria, P. 1987. Sequence from picomole quantities of proteins electroblotted onto polyvinylidene diflouride membranes. J. Biol. Chem. 262, 10035-10038.

24. Schagger, H. and G. von Jagow. 1987. Tricine-sodium dodecyl sulfate-polyacrylamide gel electrophoresis for the separation of proteins in the range of 1 to 100 kKa. Anal. Biochem. 166, 368-379.

25. Kaper, J. B. and Levine, M. M. Progress towards a vaccine against enterotoxigenic *Esherichia coli* vaccine 1988, 6, 197-199.

26. Levine M., Morris, J. G. Losnosky, G., Boedeker E., and Rowe, B. Fimbriae (pili) adhesins as vaccine. In: *Molecular Biology of Microbial Pathogenicity. Protein-Cargohydrate Interactions in Biological System.* (Ed. Lark, D., et. al.) Academic Press, London, 1986, pp. 143-145.

27. Schmidt, M., Kelly E. P., Tseng, L.-Y., and Boedeker, E. C. Towards and oral *E. Coli* pilus vaccine for traveler's diarrhea: suspentibility of purified colonization factor antigen/II to proteolytic digestion. Gastroenterology 1985, 88, A1575.

28. Wise, D. L. Fellmann, T. D. Sanderson, J. E. and Wentworth, R. R. Lactic glycolic acid polymer. In: Drug carriers in biology and medicine (Ed. Gregoriades, G.) Academic Press, London, 1979: 237-270.

29. Eldridge, J. H. Gilley, R. M. Staas, J. K. Moldoveanu, Z., Meulbroek, J. A. and Tice, T. r. Biodegradable microspheres: vaccine delivery system for oral immunization. Curr. Top. Microbiol, Immunol. 1989, 146, 59-66.

30. Eldride, J. H. Hammond, C. J. Meubroek, J. A. Staas, J. K., Gilley, R. M., and Tice, T. R. Controlled vaccine release in the gut-associated lymphoid tissue. I. Orally administered biodegradable microsphere target the Peyer's patches. J. Controlled release 2989, 11, 205.

31. Eldridge, J. H. Staas, J. K., Meubroek J. A., McGhee, J. R., Tice, T. R. and Gilley, R. M. Biodegradable microsphere as a vaccine delivery system. Mol. Immunol, 1991, 28, 287-294.

32. Moldoveanu, Z. Staas, J. K. Gilley, R. M., Ray, R., Compans, R. W. Eldridge, J. H. Tice, T. R., and Mestecky, J. Immune Respone to influenae virus in orally and systemically immunized. Curr. Top. Microbiol. Immunol. 1989, 146, 91-99.

33. McQueen, C. E., Boedeker, E. C., Reid, R. H., Jarboe, D., Wolf, M., Le, M., and Brown, W. R. Pili in microsphere protect rabbits for diarrhea induced by *E. coli* strain RDEC-1. Vaccine (in press).

34. Jarboe, D., Reid, R., McQueen, C., and Boedeker, E., In vitro lymphocyte proliferation after sensitization or rabbit lymphoid tissue with encapsulated or non-encapsulated AF/R1 pilus adhesin of *E coli* strain RDED-1. Abstracts of the Annual Meeting of the American Society of Microbiology, May 1990, 1990, 121.

35. Ebel, J. P. A method for quantifying particle absorption from the samll intestine of the mouse. Pharm. Res. 1990, 7, 848-851.

36. Levine, M. M., Ristaino, P., Morley, G., Smyth, C., Knutton, S., Boedeker, E., Black, R., Young, C., Clements, M. L. Cheney, C., and Patnaik, R. Coli surface antigens 1 and 3 colonization: Morphology, purification, and immune reponses in humans. Infect, Immun, 1984, 44, 409-420.

37. Spector, S. A. 1981. Immunoprophylaxis and immunotherapy, pp 770-793. In: Medical Microbiology and Infectious Diseases. A. I. Braude (editor), W. B. Sauders Company, Philadelphia.

38. Jolles, P., and A. Paraf. 1973. Aluminum adjuvants in human sensitization. pp 106-108. In: Chemical basis if adjuvants, molecular biology, biochemistry, and biophysics, Volume 13. A. K. Kleinzeller, G. F. Springer, and H. G. Willman (editors), Springer-Verlag, Berlin.

39. Brackman, P. S., and F. R. Fekety, 1958. Industrial anthrax. Ann. N.Y. Acad. Sci. 70:575-584.

40. Maupas, P., A. Goudeau, P. Coursaget, J. Drucker, and P. Bagros. 1978. Hepatitis B vaccine efficacy in high risk settings, a two year study. Intervirol. 10:196-208.

41. Merck, Sharp, and Dohme. Heptavax-B Vaccine package insert. 6. Dean, J. A., and A. J. Ognibene. 1982. Hepatitis. pp. 419-441. In: Medical Department, United States Army Internal Medicine in vietnam, Vol II: General Medicine and Infectious Disease. A. J. Ognibene, O. Brrett (editors), Office of the Surgeon General and Center of Military History, Wash. D.C.

42. Gerety, R. J. 1979. Hews from the National Institute of Allergy and Infectious Diseases: Summary of an international workshop on Hepatitus B vaccines. J. Infect. Dis. 140:642-648.

43. Reed, J. J., Muench, H. 1939. A simple method of estimating fifty percent endpoints. Amer. J. Hyg. 27:493-497.

44. Bradford, M. 1976. A rapid an sensitive method for the quantitation of microgram quantities of protein utilizing the pracile of protein-dye binding. Anal. Biochem. 72:248-254.

45. Jackanicy, T. M., et al. 1983. Polylactic acid as a biodegradable carrier for contraceptive steroids. Contraception 8:227-234. 11. Kulkami, R. K., E. G. Morre, A. F. Hegyeli, and F. Leonard. 1971. Biodegradable poly (lactic acid) polymers. J. Biomed. Mater. Res. 5:169-181.

46. Cutright D. E., P. Bienvenido, J. Beasley, III, W. T. Larson, and W.R. Posey. 1974. Degrdation rates of polymers and copolymers and polyglycolic acids. Oral Surg. 37:142-152.

We claim:

1. An immunostimulating composition comprising encapsulation-microspheres, which may contain a pharmaceutically-acceptable adjuvant, wherein said microspheres having a diameter between 1 nanometers (nm) to 10 microns (um) are comprised of (a) a biodegradable-biocompatible poly (DL-lactide-co-glycolide) or polyglycolide as the bulk matrix, wherein the relative ratio between the amount of lactide; glycolide components are within the range of 52:48 to 0:100 and (b) an immunogenic substance comprising Colonization Factor Antigen and hepatitis B surface antigen that serves to elicit the production of antibodies and T-lymphocyte proliferation in animals.

2. An immunostimulating composition according to claim 1 wherein the amount of said immunogenic substance is within the range of 0.1 to 1.5% based on the volume of said bulk matrix.

3. An immunostimulating composition according to claim 2 wherein the relative ratio between the lactide and glycolide component is within the range of 48:52 to 58:42.

4. An immunostimulating composition according to claim 2 wherein the size of more than 50% of said microspheres is between 5 to 10 um in diameter by volume.

5. A vaccine comprising an immunostimulating composition of claim 4 and a sterile, pharmaceutically-acceptable carrier therefor.

6. A vaccine comprising an immunostimulating composition of claim 5 wherein said immunogenic substance is Colony Factor Antigen (CFA/II).

7. A vaccine comprising an immunostimulating composition of claim 5 wherein said immunogenic substance is hepatitis B surface antigen (HBsAg).

8. A method for the vaccination against bacterial infection comprising administering to a human, an antibactericidally effective amount of a composition of claim 6.

9. A method according to claim 8 wherein the bacterial infection is caused by a bacteria selected from the group consisting of *Salmonella typhi, Shigela sonnei, Shigella flexneri, Shigella dysenteriae, Shigella boydii, Escheria coli, Vibrio cholera, yersinia, staphylococus, clostridium, and campylobacter.*

10. A method for the vaccination against viral infection comprising administering to a human an antivirally effective amount of a composition of claim 7.

11. An immunostimulating composition comprising encapsulating-microspheres, which may contain a pharmaceutically-acceptable adjuvant, wherein said microspheres having a diameter between 1 nanometers (nm) to 10 microns (um) are comprised of (a) a glycolide polymer as a bulk matrix and (b) an immunogenic substance comprising Colonization Factor Antigen and hepatitis B surface antigen that serves to elicit the production of antibodies and T-lymphocyte proliferation in animals.

12. A method for the treatment of an animal in need thereof against infection by enteropathopathogenic organisms or hepatitis B virus comprising administering to said animal an immunogenic amount of an immunostimulating composition of claim 3.

13. A method according to claim 12 wherein the immunostimulating composition is administered orally.

14. A method according to claim 12 wherein the immunostimulating composition is administered parenterally.

* * * * *